United States Patent
Monahan et al.

(10) Patent No.: US 9,415,113 B2
(45) Date of Patent: Aug. 16, 2016

(54) TARGETING MONOMERS AND POLYMERS HAVING TARGETING BLOCKS

(75) Inventors: Sean D. Monahan, Lake Forest Park, WA (US); Paul H. Johnson, Snohomish, WA (US); Michael S. DeClue, Seattle, WA (US); Priyadarsi De, West Bengal (IN); Anna S. Gall, Woodinville, WA (US); Patrick S. Stayton, Seattle, WA (US); Allan S. Hoffman, Seattle, WA (US); Charbel Diab, Seattle, WA (US)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 617 days.

(21) Appl. No.: 13/510,279

(22) PCT Filed: Nov. 17, 2010

(86) PCT No.: PCT/US2010/056993
§ 371 (c)(1),
(2), (4) Date: Aug. 10, 2012

(87) PCT Pub. No.: WO2011/062965
PCT Pub. Date: May 26, 2011

(65) Prior Publication Data
US 2013/0011362 A1   Jan. 10, 2013

Related U.S. Application Data

(60) Provisional application No. 61/262,512, filed on Nov. 18, 2009, provisional application No. 61/262,516, filed on Nov. 18, 2009.

(51) Int. Cl.
*A61K 31/787* (2006.01)
*C07D 221/02* (2006.01)
*A61K 47/06* (2006.01)
*A61K 47/48* (2006.01)

(52) U.S. Cl.
CPC ..... *A61K 47/48176* (2013.01); *A61K 47/48107* (2013.01); *A61K 47/48146* (2013.01); *A61K 47/48238* (2013.01)

(58) Field of Classification Search
CPC ............ A61K 8/673; A61K 47/48107; A61K 47/48176
USPC ....................................... 424/78.23; 526/259
See application file for complete search history.

(56) References Cited

U.S. PATENT DOCUMENTS

| | | | |
|---|---|---|---|
| 4,699,784 A | 10/1987 | Shih | |
| 5,057,313 A | 10/1991 | Shih | |
| 5,827,819 A * | 10/1998 | Yatvin | A61K 31/00 424/450 |
| 6,359,054 B1 | 3/2002 | Lemieux | |
| 6,383,811 B2 | 5/2002 | Wolff | |
| 6,410,057 B1 | 6/2002 | Kweon-Choi | |
| 6,780,428 B2 | 8/2004 | Ranger | |
| 6,835,393 B2 | 12/2004 | Hoffman | |
| 6,919,091 B2 | 7/2005 | Trubetskoy | |
| 6,939,564 B2 | 9/2005 | Ranger | |
| 7,033,607 B2 | 4/2006 | Trubetskoy | |
| 7,094,810 B2 | 8/2006 | Sant | |
| 7,098,032 B2 | 8/2006 | Trubetskoy | |
| 7,217,776 B1 | 5/2007 | Mallapragada | |
| 7,374,778 B2 | 5/2008 | Hoffman | |
| 7,510,731 B2 | 3/2009 | Ranger | |
| 7,524,680 B2 | 4/2009 | Wolff | |
| 7,718,193 B2 | 5/2010 | Stayton | |
| 7,737,108 B1 | 6/2010 | Hoffman | |
| 8,367,113 B2 | 2/2013 | Gu | |
| 2001/0007666 A1 | 7/2001 | Hoffman | |
| 2002/0172171 A1 | 11/2002 | Martin | |
| 2003/0013133 A1 | 1/2003 | Kataoka | |
| 2003/0134420 A1 | 7/2003 | Lollo | |
| 2003/0191081 A1 | 10/2003 | Lemieux | |
| 2003/0211167 A1 | 11/2003 | Gustavsson | |
| 2004/0072784 A1 | 4/2004 | Sant | |
| 2004/0138095 A1 | 7/2004 | Soula | |
| 2004/0151775 A1 | 8/2004 | Rozema | |
| 2004/0162235 A1 | 8/2004 | Trubetskoy | |
| 2005/0220880 A1 | 10/2005 | Lewis | |
| 2005/0260276 A1 | 11/2005 | Yang | |
| 2006/0134221 A1 | 6/2006 | Geall | |
| 2006/0165810 A1 | 7/2006 | Discher | |
| 2006/0171980 A1 | 8/2006 | Helmus | |
| 2006/0235161 A1 | 10/2006 | Heller | |
| 2006/0240092 A1 | 10/2006 | Breitenkamp | |
| 2007/0003609 A1 | 1/2007 | Collin-Djangone | |
| 2007/0010632 A1 | 1/2007 | Kaplan | |
| 2007/0037891 A1 | 2/2007 | Esfand | |
| 2007/0059271 A1 | 3/2007 | Kataoka | |
| 2007/0110709 A1 | 5/2007 | Ranger | |
| 2007/0224241 A1 | 9/2007 | Stayton | |

(Continued)

FOREIGN PATENT DOCUMENTS

EP   0 321 233 A1   6/1989
EP   2 180 004 A1   4/2010

(Continued)

OTHER PUBLICATIONS

Correspond definition (http://www.oxforddictionaries.com/us/definition/american_english/correspond, accessed on Mar. 7, 2015, 2 pages).*

(Continued)

*Primary Examiner* — Alma Pipic
(74) *Attorney, Agent, or Firm* — Christensen O'Connor Johnson Kindness PLLC

(57) ABSTRACT

Provided herein are monomers incorporating folate or other targeting agent, polymers prepared therefrom, polymers prepared therefrom having a therapeutic agent covalently coupled thereto, as well as micelles and therapeutic compositions thereof.

13 Claims, No Drawings

(56) References Cited

U.S. PATENT DOCUMENTS

| | | |
|---|---|---|
| 2007/0299240 A1 | 12/2007 | Gopferich |
| 2008/0069902 A1 | 3/2008 | Zhao |
| 2008/0081075 A1 | 4/2008 | Hsiue |
| 2008/0171067 A1 | 7/2008 | Govindan |
| 2009/0036625 A1 | 2/2009 | Chang |
| 2010/0150952 A1 | 6/2010 | Stayton |

FOREIGN PATENT DOCUMENTS

| | | | |
|---|---|---|---|
| FR | 2 767 829 | A1 | 3/1999 |
| WO | 99/29303 | A1 | 6/1999 |
| WO | 03/087188 | A1 | 10/2003 |
| WO | 2005/108614 | A2 | 11/2005 |
| WO | 2006/016166 | A1 | 2/2006 |
| WO | 2007/008300 | A2 | 1/2007 |
| WO | 2007/109584 | A1 | 9/2007 |
| WO | 2008/004978 | A1 | 1/2008 |
| WO | 2008/022309 | A2 | 2/2008 |
| WO | 2008/071009 | A1 | 6/2008 |
| WO | 2008/085556 | A2 | 7/2008 |
| WO | 2008/120914 | A1 * | 10/2008 |
| WO | 2008/148174 | A1 | 12/2008 |
| WO | 2008/153940 | A1 | 12/2008 |
| WO | 2009/009025 | A1 | 1/2009 |
| WO | 2009/021728 | A2 | 2/2009 |
| WO | 2009/140421 | A2 | 11/2009 |
| WO | 2009/140423 | A2 | 11/2009 |
| WO | 2009/140427 | A2 | 11/2009 |
| WO | 2009/140429 | A2 | 11/2009 |
| WO | 2009/140432 | A2 | 11/2009 |
| WO | 2010/021770 | A1 | 2/2010 |
| WO | 2010/053596 | A1 | 5/2010 |
| WO | 2010/053597 | A2 | 5/2010 |
| WO | 2010/054266 | A2 | 5/2010 |
| WO | 2010/077678 | A2 | 7/2010 |

OTHER PUBLICATIONS

Cayman Chemical (https://www.caymanchem.com/app/template/Product.vm/catalog/13960, 5 pages, accessed Oct. 4, 2015).*

Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Cho, Y.W., et al.. "Polycation Gene Delivery Systems: Escape From Endosomes to Cytosol," Journal of Pharmacy and Pharmacology 55(6):721-734, Jun. 2003.

Convertine, A.J., et al., "Development of a Novel Endosomolytic Diblock Copolymer for siRNA Delivery," Journal of Controlled Release 133(3):221-229, Feb. 2009.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by Raft Polymerization," Chemical Communications 28(28):3245-3247, Jul. 2008.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Jeong, J.H., et al., "siRNA Conjugate Delivery Systems," Bioconjugate Chemistry 20(1):5-14, Jan. 2009.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared Via the RAFT Copolymerization Technique," Biomacromolecules 7(10):2736-2741, Oct. 2006.

Meyer, M., et al., "Synthesis and Biological Evaluation of a Bioresponsive and Endosomolytic siRNA-Polymer Conjugate," Molecular Pharmaceutics 6(3):752-762, May-Jun. 2009.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Oishi, M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

Peppas, N. A., "Is There a Future in Glucose-Sensitive, Responsive Insulin Delivery Systems?" Drug Delivery Science and Technology 14(4):247-256, Sep. 2004.

Read, M.L., et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.

Segura, T., and J.A. Hubbell, "Synthesis and In Vitro Characterization of an ABC Triblock Copolymer for siRNA Delivery," Bioconjugate Chemistry 18(3):736-745, May 2007.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.

Stayton, P.S., et al., "Intelligent Biohybrid Materials for Therapeutic and Imaging Agent Delivery," Proceedings of the IEEE 93(4):726-736, Apr. 2005.

Torchilin, V.P., "Micellar Nanocarriers: Pharmaceutical Perspectives," Pharmaceutical Research 24(1):1-16, Jan. 2007.

Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.

Yamamoto, S.-I., et al., "Temperature- and pH-Responsive Dense Copolymer Brushes Prepared by ATRP," Macromolecules 41(19):7013-7020, Oct. 2008.

Yessine, M.-A., et al., "Proton-Actuated Membrane-Destabilizing Polyion Complex Micelles," Bioconjugate Chemistry 18(3):1010-1014, May-Jun. 2007.

Extended European Search Report mailed Feb. 5, 2014, issued in corresponding European Application No. 09 825 146.5, filed May 13, 2009, 9 pages.

Cheung, C.Y., et al., "A pH-Sensitive Polymer That Enhances Cationic Lipid-Mediated Gene Transfer," Bioconjugate Chemistry 12(6):906-910, Oct. 2001.

(56) References Cited

OTHER PUBLICATIONS

Hood, J.D., et al., "Tumor Regression by Targeted Gene Delivery to the Neovasculature," Science, New Series 296 (5577):2404-2407, Jun. 2002.

Jeong, Y.-I., et al., "Cellular Recognition of Paclitaxel-Loaded Polymeric Nanoparticles Composed of Poly(y-benzyl L-glutamate) and Poly(ethylene glycol) Diblock Copolymer Endcapped With Galactose Moiety," International Journal of Pharmaceutics 296(2005):151-161, Apr. 2005.

Joralemon, M.J., et al., "Synthesis, Characterization, and Bioavailability of Mannosylated Shell Cross-Linked Nanoparticles," Biomacromolecules 5(3):903-913, May-Jun. 2004.

Kabanov, A.V., et al., "Pluronic Micelles as a Tool for Low-Molecular Compound Vector Delivery Into a Cell: Effect of *Staphylococcus-aureus* Enterotoxin B on Cell Loading With Micelle Incorporated Fluorescent Dye," Biochemistry International 26(6):1035-1042, May 1992.

Kyriakides, T.R., et al., "pH-Sensitive Polymers That Enhance Intracellular Drug Delivery in Vivo," Journal of Controlled Release 78(1-3):295-303, Jan. 2002.

Le Garrec, D., et al., "Micelles in Anticancer Drug Delivery," American Journal of Drug Delivery 2(1):15-42, Mar. 2004.

Lee, E.S., et al., "Super pH-Sensitive Multifunctional Polymeric Micelle," Nano Letters 5(2):325-329, Feb. 2005.

Nagasaki, Y. et al., "Sugar-Installed Block Copolymer Micelles: Their Preparation and Specific Interaction With Lectin Molecules," Biomacromolecules 2(4):1067-1070, Winter 2001.

Raso, V., "Intracellular Targeting Using Bispecific Antibodies," Methods in Molecular Medicine 25:37-49, Jan. 2000.

Sawant, R.M., et al., "'Smart'" Drug Delivery Systems: Double-Targeted pH-Responsive Pharmaceutical Nanocarriers, Bioconjugate Chemistry 17:943-949, Jun. 2006.

Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.

Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.

Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.

Yoo, H.S., and T.G. Park, "Folate Receptor Targeted Biodegradable Polymeric Doxorubicin Micelles," Journal of Controlled Release 96(2):273-283, Apr. 2004.

Fishbein, I., et al., "Local Delivery of Gene Vectors From Bare-Metal Stents by Use of a Biodegradable Synthetic Complex Inhibits In-Stent Restenosis in Rat Carotid Arteries," Circulation 117(16):2096-2103, Apr. 2008.

International Search Report and Written Opinion mailed Jun. 27, 2011, issued in corresponding International Application No. PCT/US2010/056993, filed Nov. 17, 2010, 7 pages.

Varghese, O.P., et al., "In Situ Cross-Linkable High Molecular Weight Hyaluronan—Bisphosphonate Conjugate for Localized Delivery and Cell-Specific Targeting: A Hydrogel Linked Prodrug Approach," Journal of the American Chemical Society 131(25):8781-8783, Jul. 2009.

\* cited by examiner

TARGETING MONOMERS AND POLYMERS HAVING TARGETING BLOCKS

CROSS-REFERENCE TO RELATED APPLICATIONS

This application claims the priority benefit of U.S. Provisional Patent Application No. 61/262,512, filed Nov. 18, 2009, and U.S. Provisional Patent Application No. 61/262,516, filed Nov. 18, 2009 each of which is incorporated herein by reference in its entirety.

STATEMENT OF JOINT RESEARCH AGREEMENT

The subject matter of the claimed invention was made as a result of activities undertaken within the scope of a joint research agreement, within the meaning of 35 U.S.C. §103 (c)(3) and 37C.F.R. §1.104(c)(4)(ii), by or on behalf of the University of Washington and PhaseRx, Inc., that was in effect on or before the claimed invention was made.

BACKGROUND OF THE INVENTION

In certain instances, it is beneficial to provide therapeutic agents, such as polynucleotides (e.g., oligonucleotides) to living cells. In some instances, delivery of such polynucleotides by means of a polymeric carrier to a living cell provides a therapeutic benefit.

SUMMARY OF THE INVENTION

Among the various aspects of the invention is a monomer corresponding to Formula M1

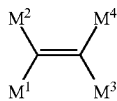

Formula M1 wherein $M^1$ and $M^2$ are independently selected from the group consisting of hydrogen, hydrocarbyl, substituted hydrocarbyl, heterocyclo, and substituted carbonyl, provided, however, $M^1$ and $M^2$ are not each selected from the group consisting of aryl, heteroaryl, and heterosubstituted carbonyl;

$M^3$ is hydrogen, hydrocarbyl, substituted hydrocarbyl, heterocyclo, or substituted carbonyl, and $M^4$ is substituted hydrocarbyl, substituted heterocyclo, or substituted carbonyl, provided, (i) $M^4$ contains as a terminal moiety, a targeting moiety selected from the group consisting of bisphosphonate, bisphosphonate analogs, biotin, PSMA inhibitors, peptides, folate and folate analogs, and (ii) $M^3$ and $M^4$ are not each selected from the group consisting of optionally substituted aryl, optionally substituted heteroaryl, and heterosubstituted carbonyl.

Another aspect of the present invention is a polymer comprising the residue of a monomer corresponding to Formula M1.

Other aspects of the invention will be, in part apparent, and in part pointed out, hereinafter.

ABBREVIATIONS AND DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

When introducing elements of the present invention or the preferred embodiment(s) thereof, the articles "a," "an," "the" and "said" are intended to mean that there are one or more of the elements. The terms "comprising", "including" and "having" are intended to be inclusive and mean that there may be additional elements other than the listed elements.

Aliphatic: unless otherwise indicated, "aliphatic" or "aliphatic group" means an optionally substituted, non-aromatic hydrocarbon moiety. The moiety may be, for example, linear, branched, or cyclic (e.g., mono- or polycyclic such as fused, bridging, or spiro-fused polycyclic), or a combination thereof. Unless otherwise specified, aliphatic groups contain 1-20 carbon atoms.

Alkyl: unless otherwise indicated, the alkyl groups described herein are preferably lower alkyl containing from one to eight carbon atoms in the principal chain and up to 20 carbon atoms. They may be linear, branched or cyclic and include methyl, ethyl, propyl, butyl, hexyl and the like.

Amino: unless otherwise indicated, the term "amino" as used herein alone or as part of another group denotes the moiety —$NR_1R_2$ wherein $R_1$ and $R_2$ are independently hydrogen, hydrocarbyl, substituted hydrocarbyl or heterocyclo.

Amide or Amido: unless otherwise indicated, the "amide" or "amido" moieties represent a group of the formula —$CONR_1R_2$ wherein $R_1$ and $R_2$ are as defined in connection with the term "amino." "Substituted amide," for example, refers to a group of formula —$CONR_1R_2$ wherein at least one of $R_1$ and $R_2$ are other than hydrogen. "Unsubstituted amido," for example, refers to a group of formula —$CONR_1R_2$, wherein $R_1$ and $R_2$ are both hydrogen.

Anionic Monomer, Anionic Monomeric Unit or Anionic Repeat Unit: unless otherwise indicated, an "anionic monomer," "anionic monomeric unit" or "anionic repeat unit" is a monomer or monomeric unit bearing a group that is present in an anionic charged state or in a non-charged state, but in the non-charged state is capable of becoming anionic charged, e.g., upon removal of an electrophile (e.g., a proton ($H^+$), for example in a pH dependent manner). In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, phosphates, and sulfonamides.

Anionic species: unless otherwise indicated, an "Anionic species" is a group, residue or molecule that is present in an anionic charged or non-charged state, but in the non charged state is capable of becoming anionic charged, e.g., upon removal of an electrophile (e.g., a proton ($H^+$), for example in a pH dependent manner). In certain instances, the group, residue or molecule is substantially negatively charged at an approximately physiological pH but undergoes protonation and becomes substantially neutral at a weakly acidic pH.

Aryl: unless otherwise indicated, the term "aryl" or "aryl group" or the abbreviation "Ar" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

Attached: unless otherwise indicated, two moieties or compounds are "attached" if they are held together by any interaction including, by way of example, one or more covalent bonds, one or more non-covalent interactions (e.g., ionic bonds, static forces, van der Waals interactions, combinations thereof, or the like), or a combination thereof.

Block Copolymer: unless otherwise indicated, a "block copolymer" comprises two or more homopolymer or copolymer subunits linked by covalent bonds. Block copolymers with two or three distinct blocks are called diblock copolymers and triblock copolymers, respectively. A schematic generalization of a diblock copolymer is represented by the formula $[A_aB_bC_c \ldots]_m-[X_xY_yZ_z \ldots]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: x-x-y-z-x-y-z-y-z-y-z-z-z . . . . A non-limiting, exemplary alternating random configuration may have the non-limiting form: x-y-x-z-y-x-y-z-y-x-z . . . , and an exemplary regular alternating configuration may have the non-limiting form: x-y-z-x-y-z-x-y-z . . . . An exemplary regular block configuration may have the following non-limiting configuration: . . . x-x-x-y-y-z-z-z-x-x-x . . . , while an exemplary random block configuration may have the non-limiting configuration: . . . x-x-x-z-z-x-x-y-y-y-z-z-z-x-x-z-z-z- . . . . In a gradient polymer, the content of one or more monomeric units increases or decreases in a gradient manner from the alphaend of the polymer to the omega-end. In none of the preceding generic examples is the particular juxtaposition of individual constitutional units or blocks or the number of constitutional units in a block or the number of blocks meant nor should they be construed as in any manner bearing on or limiting the actual structure of block copolymers forming a micelle described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

Cationic Monomer, Cationic Monomeric Unit or Cationic Repeat Unit: unless otherwise indicated, an "cationic monomer," "cationic monomeric unit" or "cationic repeat unit" is a monomer or a monomeric or repeat unit (the terms "monomeric unit" and "repeat unit" being used interchangeably) bearing a cation or a moiety capable of having a cationic charge upon addition of an electrophile (e.g., a proton (H+)).

Chargeable species, Chargeable Group, or Chargeable Monomeric Unit: unless otherwise indicated, a "chargeable species," "chargeable group" or "chargeable monomeric unit" is a species, group or monomeric unit in either a charged or non-charged state. In certain instances, a "chargeable monomeric unit" is one that can be converted to a charged state (either an anionic or cationic charged state) by the addition or removal of an electrophile (e.g., a proton ($H^+$), for example in a pH dependent manner). The use of any of the terms "chargeable species", "chargeable group", or "chargeable monomeric unit" includes the disclosure of any other of a "chargeable species", "chargeable group", or "chargeable monomeric unit" unless otherwise stated. A "chargeable species" that is "charged or chargeable to an anion" or "charged or chargeable to an anionic species" is a species or group that is either in an anionic charged state or non-charged state, but in the non-charged state is capable of being converted to an anionic charged state, e.g., by the removal of an electrophile, such as a proton ($H^+$). A "chargeable species" that is "charged or chargeable to a cation" or "charged or chargeable to a cationic species" is a species or group that is either in an cationic charged state or non-charged state, but in the non-charged state is capable of being converted to a cationic charged state, e.g., by the addition of an electrophile, such as a proton ($H^+$). "Chargeable monomeric units" described herein are used interchangeably with "chargeable monomeric residues".

Copolymer: unless otherwise indicated, the term "copolymer" signifies that the polymer is the result of polymerization of two or more different monomers.

Critical Micelle Concentration and CMC: unless otherwise indicated, the "critical micelle concentration" or "CMC" is the concentration at which a micelle self-assembles. The CMC can be determined by well known methods such as the uptake of a hydrophobic probe molecule (for example, a pyrene fluorescence assay).

Dicer Substrate: unless otherwise indicated, a "dicer substrate" is a substrate for the RNase III family member Dicer in cells, the substrate possessing at least about 25 base pair duplex RNA. Dicer substrates are cleaved to produce approximately 21 base pair duplex small interfering RNAs (siRNAs) that evoke an RNA interference effect resulting in gene silencing by mRNA knockdown.

Endosome Disruptive & Endosomolytic: unless otherwise indicated, a composition is "endosome disruptive," also sometimes referred to as "endosomolytic," if the effect of the composition upon the endosome is to increase the permeability of the endosomal membrane.

Heteroalkyl: unless otherwise indicated, the term "heteroalkyl" means an alkyl group wherein at least one of the backbone carbon atoms is replaced with a heteroatom.

Heteroaryl and Het: unless otherwise indicated, the term "heteroaryl" and the abbreviation "Het" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heteroatom: unless otherwise indicated, the term "heteroatom" means an atom other than hydrogen or carbon, such as an oxygen, sulfur, nitrogen, phosphorus, boron, arsenic, selenium or silicon atom.

Heterocyclo: unless otherwise indicated, the terms "heterocyclo" and "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heterohydrocarbyl: unless otherwise indicated, the term "heterohydrocarbyl" means a hydrocarbyl group wherein at least one of the chain carbon atoms is replaced with a heteroatom.

Hydrocarbon or Hydrocarbyl: unless otherwise indicated, the terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms Hydrophobic: unless otherwise indicated, the terms "hydrophobic" and "hydrophobicity" are terms of art describing a physical property of a composition measured by the free energy of transfer of the composition between a non-polar solvent and water (Hydrophobicity regained. Karplus P. A., *Protein Sci.*, 1997, 6: 1302-1307.). The hydrophobicity of a composition can be measured by its log P value, the logarithm of a partition coefficient (P), which is defined as the ratio of concentrations of a compound in the two phases of a mixture of two immiscible solvents, e.g., octanol and water. Experimental methods of determination of hydrophobicity as well as methods of computer-assisted calculation of log P values are known to those skilled in the art. Hydrophobic species of the present invention include but are not limited to aliphatic, heteroaliphatic, aryl, and heteroaryl groups.

Hydrophobic Core: unless otherwise indicated, a "hydrophobic core" comprises hydrophobic moieties. In certain instances, a "hydrophobic core" is substantially non-charged (e.g., the charge is substantially net neutral).

Hydrophobic Repeat Unit: unless otherwise indicated, a "hydrophobic repeat unit" or a "hydrophobic monomeric unit" is a repeat unit or monomeric unit of a polymer possessing a hydrophobic substituent.

Hydrophobic Species: unless otherwise indicated, the terms "hydrophobic species" and "hydrophobic-enhancing moiety" is a moiety such as a substituent, residue or a group which, when covalently attached to a molecule, such as a monomer or a polymer, increases the molecule's hydrophobicity.

Inhibition, Silencing, Attenuation or Knock-Down: unless otherwise indicated, the terms "inhibition," "silencing," and "attenuation" as used herein refer to a measurable reduction in expression of a target mRNA or the corresponding protein as compared with the expression of the target mRNA or the corresponding protein in the absence of a knockdown agent. "Knockdown," or the reduction in expression of the target mRNA or the corresponding protein, can be assessed by measuring the mRNA levels using techniques well known in the art such as quantitative polymerase chain reaction (qPCR) amplification, RNA solution hybridization, nuclease protection, northern blotting and hybridization, and gene expression monitoring with a microarray; and in the case of proteins by techniques well known in the art such as SDS-PAGE, antibody binding, western blot analysis, immunoprecipitation, radioimmunoassay or enzyme-linked immunosorbent assay (ELISA), fluorescence activated cell analysis and immunocytochemistry.

Inhibit gene expression: unless otherwise indicated, the phrase "inhibit gene expression" means to cause any measurable reduction in the amount of an expression product of the gene. The expression product can be an RNA transcribed from the gene (e.g., an mRNA) and/or a polypeptide translated from an mRNA transcribed from the gene. The level of expression may be determined using standard techniques for measuring mRNA or protein.

Membrane Destabilizing Polymer or Membrane Destabilizing Block: unless otherwise indicated, a "membrane destabilizing polymer" or a "membrane destabilizing block" can directly or indirectly elicit a change (e.g., a permeability change) in a cellular membrane structure (e.g., an endosomal membrane) so as to permit an agent (e.g., polynucleotide), in association with or independent of a micelle (or a constituent polymer thereof), to pass through such membrane structure, for example, to enter a cell or to exit a cellular vesicle (e.g., an endosome). A membrane destabilizing polymer can be (but is not necessarily) a membrane disruptive polymer. A membrane disruptive polymer can directly or indirectly elicit lysis of a cellular vesicle or otherwise disrupt a cellular membrane (e.g., as observed for a substantial fraction of a population of cellular membranes). Generally, membrane destabilizing or membrane disruptive properties of polymers or micelles can be assessed by various means. In one non-limiting approach, a change in a cellular membrane structure can be observed by assessment in assays that measure (directly or indirectly) release of an agent (e.g., polynucleotide) from cellular membranes (e.g., endosomal membranes), for example, by determining the presence or absence of such agent, or an activity of such agent, in an environment external to such membrane. Another non-limiting approach involves measuring red blood cell lysis (hemolysis), e.g., as a surrogate assay for a cellular membrane of interest. Such assays may be done at a single pH value or over a range of pH values.

Micelle: unless otherwise indicated, a "micelle" is a particle comprising a core and a hydrophilic shell, wherein the core is held together at least partially, predominantly or substantially through hydrophobic interactions. The micelle may be, for example, a multi-component, nanoparticle comprising at least two domains, the inner domain or core, and the outer domain or shell. Micelle particles described herein may have any suitable or desired diameter, e.g., of less than 1000 nanometers (nm). In general, the micelle should have dimensions small enough to allow their uptake by eukaryotic cells. Typically, the micelle has a longest lateral dimension, also known as the diameter, of 200 nm or less. In some embodiments, the micelle has a diameter of 100 nm or less. Smaller micelles, e.g. having diameters of about 10 nm to about 200 nm, about 20 nm to about 100 nm, or 50 nm or less, e.g., 5 nm-30 nm, are used in some embodiments. Micelle particle size can be determined in any manner, including, but not limited to, by gel permeation chromatography (GPC), dynamic light scattering (DLS), electron microscopy techniques (e.g., TEM), and other methods.

Non-Charged Repeat Units: unless otherwise indicated, a "non-charged repeat unit" is a repeat unit that is neither an anionic repeat unit nor a cationic repeat unit.

Nucleoside: unless otherwise indicated, the term "nucleoside" is used to describe a composition comprising a monosaccharide and a base. The monosaccharide includes but is not limited to pentose and hexose monosaccharides. The monosaccharide also includes monosaccharide mimetics and monosaccharides modified by substituting hydroxyl groups with halogens, methoxy, hydrogen or amino groups, or by esterification of additional hydroxyl groups.

Nucleotide: unless otherwise indicated, the term "nucleotide," in its broadest sense, refers to any compound and/or substance that is or can be incorporated into a polynucleotide (e.g., oligonucleotide) chain. In some embodiments, a nucleotide is a compound and/or substance that is or can be incorporated into a polynucleotide (e.g., oligonucleotide) chain via a phosphodiester linkage. In some embodiments, "nucleotide" refers to individual nucleic acid residues (e.g. nucleotides and/or nucleosides). In certain embodiments, "at least one nucleotide" refers to one or more nucleotides present; in various embodiments, the one or more nucleotides are discrete nucleotides, are non-covalently attached to one another, or are covalently attached to one another. As such, in certain instances, "at least one nucleotide" refers to one or more polynucleotide (e.g., oligonucleotide). In some embodiments, a polynucleotide is a polymer comprising two or more nucleotide monomeric units.

Oligonucleotide: unless otherwise indicated, the term "oligonucleotide" refers to a polymer comprising 7-200 nucleotide monomeric units. In some embodiments, "oligonucleotide" encompasses single and or/double stranded RNA as well as single and/or double-stranded DNA. Furthermore, the terms "nucleotide", "nucleic acid," "DNA," "RNA," and/or similar terms include nucleic acid analogs, i.e., analogs having a modified backbone, including but not limited to peptide nucleic acids (PNA), locked nucleic acids (LNA), phosphono-PNA, morpholino nucleic acids, or nucleic acids with modified phosphate groups (e.g., phosphorothioates, phosphonates, 5'-N-phosphoramidite linkages). Nucleotides can be purified from natural sources, produced using recombinant expression systems and optionally purified, chemically synthesized, etc. In some embodiments, a nucleotide is or comprises a natural nucleoside phosphate (e.g. adenosine, thymidine, guanosine, cytidine, uridine, deoxyadenosine, deoxythymidine, deoxyguanosine, and deoxycytidine phosphate). In some embodiments, the base includes any bases occurring naturally in various nucleic acids as well as other modifications which mimic or resemble such naturally occurring bases. Nonlimiting examples of modified or derivatized bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5 methyluracil, uracil-5-oxyacetic acid methylester, uracil-5-oxyacetic acid, 5-methyl-2-thiouracil, 3-(3-amino-3-N-2-carboxypropyl)uracil, 2-aminoadenine, pyrrolopyrimidine, and 2,6-diaminopurine. Nucleoside bases also include universal nucleobases such as difluorotolyl, nitroindolyl, nitropyrrolyl, or nitroimidazolyl. Nucleotides also include nucleotides which harbor a label or contain abasic, i.e., lacking a base, monomers. A nucleic acid sequence is presented in the 5' to 3' direction unless otherwise indicated. A nucleotide can bind to another nucleotide in a sequence-specific manner through hydrogen bonding via Watson-Crick base pairs. Such base pairs are said to be complementary to one another. An oligonucleotide can be single stranded, double-stranded or triple-stranded.

Oligonucleotide gene expression modulator: as used herein, an "oligonucleotide gene expression modulator" is an oligonucleotide agent capable of inducing a selective modulation of gene expression in a living cell by mechanisms including but not limited to an antisense mechanism or by way of an RNA interference (RNAi)-mediated pathway which may include (i) transcription inactivation; (ii) mRNA degradation or sequestration; (iii) transcriptional inhibition or attenuation or (iv) inhibition or attenuation of translation. Oligonucleotide gene expression modulators include, regulatory RNA (including virtually any regulatory RNA) such as, but not limited to, antisense oligonucleotides, miRNA, siRNA, RNAi, shRNA, aptamers and any analogs or precursors thereof.

Oligonucleotide Knockdown Agent: unless otherwise indicated, an "oligonucleotide knockdown agent" is an oligonucleotide species which can inhibit gene expression by targeting and binding an intracellular nucleic acid in a sequence-specific manner. Non-limiting examples of oligonucleotide knockdown agents include siRNA, miRNA, shRNA, dicer substrates, antisense oligonucleotides, decoy DNA or RNA, antigene oligonucleotides and any analogs and precursors thereof.

pH Dependent, Membrane-Destabilizing: unless otherwise indicated, a "pH dependent, membrane-destabilizing" group or block is a group or block that is at least partially, predominantly, or substantially hydrophobic and is membrane destabilizing in a pH dependent manner. In certain instances, a pH dependent membrane destabilizing polymer block is a hydrophobic polymeric segment of a block copolymer and/or comprises a plurality of hydrophobic species; and comprises a plurality of chargeable species. In some embodiments, the chargeable species is anionic. In some embodiments, the anionic chargeable species is anionic at about neutral pH. In further or alternative embodiments, the anionic chargeable species is non-charged at a lower, e.g., endosomal pH. In some embodiments, the membrane destabilizing chargeable hydrophobe comprises a plurality of cationic species. The pH dependent membrane-destabilizing chargeable hydrophobe comprises a non-peptidic and non-lipidic polymer backbone. For example, a pH dependent, membrane-destabilizing block may possess anionic repeat units the substituents of which are predominantly ionized (anions) at one pH, e.g., pH 7.4, and predominantly neutral at a lesser pH, e.g., pH 5.0 whereby the pH dependent, membrane-destabilizing group or block becomes increasingly hydrophobic as a function of the drop in pH from 7.4 to 5.0.

RNAi agent: unless otherwise indicated, the term "RNAi agent" refers to an oligonucleotide which can mediate inhibition of gene expression through an RNAi mechanism and includes, but is not limited to, siRNA, microRNA (miRNA), short hairpin RNA (shRNA), asymmetrical interfering RNA (aiRNA), dicer substrate and the precursors thereof.

RNA interference (RNAi): unless otherwise indicated, the term "RNA interference" or "RNAi" refers to sequence-specific inhibition of gene expression and/or reduction in target mRNA and protein levels mediated by an at least partially double-stranded RNA, which also comprises a portion that is substantially complementary to a target RNA.

Short hairpin RNA (shRNA): unless otherwise indicated, "short hairpin RNA" or "shRNA" refers to an oligonucleotide having at least two complementary portions hybridized or capable of hybridizing with each other to form a double-stranded (duplex) structure and at least one single-stranded portion.

Short interfering RNA (siRNA): unless otherwise indicated, "short interfering RNA" or "siRNA" refers to an RNAi agent that is approximately 15-50 base pairs in length and optionally further comprises zero to two single-stranded overhangs. One strand of the siRNA includes a portion that hybridizes with a target RNA in a complementary manner. In some embodiments, one or more mismatches between the siRNA and the targeted portion of the target RNA may exist. In some embodiments, siRNAs mediate inhibition of gene expression by causing degradation of target transcripts.

Substantially Non-Charged Block: unless otherwise indicated, the term "substantially non-charged block" means a polymeric block that has a neutral charge, or a near neutral charge. For example, less than about 10 mole % of the repeat units in a block will be anionic, cationic or zwitterionic repeat units in a substantially non-charged block. By way of further example, less than about 5 mole % of the repeat units in a block will be anionic, cationic or zwitterionic repeat units in a substantially non-charged block.

Substituted or Optionally Substituted: unless otherwise indicated, the term "substituted" and "optionally substituted" means that the referenced group is or may be substituted with one or more additional suitable group(s), which may be individually and independently selected from acetals, acyl, acyloxy, alkenoxy, alkoxy, alkylthio, alkynoxy, amido, amino, aryl, aryloxy, arylthio, carbonyl, carboxamido, carboxyl, cyano, esters, ethers, hydrocarbyl, substituted hydrocarbyl, heterohydrocarbyl, substituted heterohydroalkyl, cycloalkyl, halogen, heteroalicyclic, heteroaryl, hydroxy, isocyanato, isothiocyanato, ketals, keto, mercapto, nitro, perhaloalkyl, silyl, sulfonamido, sulfonyl, thiocarbonyl, thiocyanato, thiol, and/or the protected derivatives thereof.

Therapeutic agent: unless otherwise indicated, the phrase "therapeutic agent" refers to any agent that, when administered to a subject, organ, tissue, or cell has a therapeutic effect and/or elicits a desired biological and/or pharmacological effect.

Therapeutically effective amount: unless otherwise indicated, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Zwitterionic Monomer, Zwitterionic Monomeric Unit or Zwitterionic Repeat Unit: unless otherwise indicated, a "zwitterionic monomer," "zwitterionic monomeric unit" or "zwitterionic repeat unit" is a monomer or a monomeric or repeat unit (the terms "monomeric unit" and "repeat unit" being used interchangeably) bearing (i) a cation or a moiety capable of having a cationic charge upon addition of an electrophile (e.g., a proton (H+)) and (ii) an anion or a moiety capable of having an anionic charge upon removal of an electrophile (e.g., a proton (H+)).

DETAILED DESCRIPTION OF THE PREFERRED EMBODIMENTS

Monomers

One aspect of the present invention is a targeting monomer, i.e., a monomer comprising a targeting moiety, also referred to herein as a targeting agent, that may be used in wide a range of polymerization reactions. For example, in some embodiments, the targeting moiety recognizes a cell surface antigen or binds to a receptor on the surface of the target cell. In certain other embodiments, the monomer is incorporated, along with other monomeric residues that serve as a spacer unit affording groups of targeting moieties spatially positioned to maximize their binding to a multivalent receptor or target. Suitable targeting moieties include, by way of non-limiting example, peptides, such as an integrin-binding peptides (e.g., RGD-containing peptides), LOX-1 binding peptides, Epidermal Growth Factor (EGF) peptides, neurotensin peptides, NL4 binding peptides, and YIGSR laminin peptides, vitamins, e.g., folate or folate analogs, bisphosphonates or bisphosphonate analogs, PSMA inhibitors or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting moieties of the micelles provided herein include, but are not limited to, the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, and the asialoglycoprotein receptor.

In one preferred embodiment, the targeting monomer corresponds to Formula M1

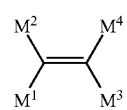

Formula M1 wherein $M^1$ and $M^2$ are independently selected from the group consisting of hydrogen, hydrocarbyl, substituted hydrocarbyl, heterocyclo, and substituted carbonyl, provided, however, $M^1$ and $M^2$ are not each selected from the group consisting of aryl, heteroaryl, and heterosubstituted carbonyl; $M^3$ is hydrogen, hydrocarbyl, substituted hydrocarbyl, heterocyclo, or substituted carbonyl, and $M^4$ is substituted hydrocarbyl, substituted heterocyclo, or substituted carbonyl, provided, (i) $M^4$ contains as a terminal moiety, a targeting moiety selected from the group consisting of bisphosphonate, bisphosphonate analogs, biotin, PSMA inhibitors, peptides, and vitamins (e.g., folate and folate analogs), and (ii) $M^3$ and $M^4$ are not each selected from the group consisting of optionally substituted aryl, optionally substituted heteroaryl, and heterosubstituted carbonyl. For example, in one such embodiment $M^3$ is hydrogen, methyl, ethyl, or propyl. By way of further example, in one such embodiment, $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)O$M^{40}$, —C(O)S$M^{40}$, —C(O)N$M^{40}M^{41}$, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)O$M^{40}$, —C(O)S$M^{40}$, or —C(O)N$M^{40}M^{41}$, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs).

In another preferred embodiment, the targeting monomer corresponds to Formula M1, $M^1$ and $M^2$ are independently selected from the group consisting of hydrogen, hydrocarbyl, substituted hydrocarbyl, heterocyclo, and substituted carbonyl, provided, however, $M^1$ and $M^2$ are not each selected from the group consisting of aryl, heteroaryl, and heterosubstituted carbonyl; $M^3$ is hydrogen, alkyl or substituted alkyl, and $M^4$ is substituted hydrocarbyl, substituted heterocyclo, or substituted carbonyl, provided, $M^4$ contains as a terminal moiety, a targeting moiety selected from the group consisting of bisphosphonate, bisphosphonate analogs, biotin, PSMA inhibitors, peptides, and vitamins (e.g., folate and folate analogs). For example, in one such embodiment $M^3$ is hydrogen, methyl, ethyl, or propyl. By way of further example, in one such embodiment, $M^4$ is —C(O)O$M^{40}$, —C(O)S$M^{40}$, —C(O)N$M^{40}$M41, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)O$M^{40}$, —C(O)S$M^{40}$, —C(O)N$M^{40}M^{41}$, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs).

In another preferred embodiment, the targeting monomer corresponds to Formula M1, one of $M^1$ and $M^2$ is hydrogen, the other of $M^1$ and $M^2$ is hydrogen hydrocarbyl, substituted hydrocarbyl, heterocyclo, or substituted carbonyl; $M^3$ is hydrogen, alkyl or substituted alkyl, and $M^4$ is substituted hydrocarbyl, substituted heterocyclo, or substituted carbonyl, provided, $M^4$ contains as a terminal moiety, a targeting moiety selected from the group consisting of bisphosphonate, bisphosphonate analogs, biotin, PSMA inhibitors, peptides, and vitamins (e.g., folate and folate analogs). For example, in one such embodiment $M^3$ is hydrogen, methyl, ethyl, or propyl. By way of further example, in one such embodiment, $M^4$ is —C(O)O$M^{40}$, —C(O)S$M^{40}$, —C(O)N$M^{40}M^{41}$, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)O$M^{40}$, —C(O)S$M^{40}$, —C(O)N$M^{40}M^{41}$, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)O$M^{40}$, —C(O)S$M^{40}$, or —C(O)N$M^{40}M^{41}$, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs).

In another preferred embodiment, the targeting monomer corresponds to Formula M2

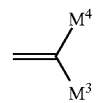

Formula M2 wherein $M^3$ is hydrogen, hydrocarbyl, substituted hydrocarbyl, heterocyclo, or substituted carbonyl, and $M^4$ is substituted hydrocarbyl, substituted heterocyclo, or substituted carbonyl, provided, (i) $M^4$ contains as a terminal moiety, a targeting moiety selected from the group consisting of bisphosphonate, bisphosphonate analogs, biotin, PSMA inhibitors, peptides, and vitamins (e.g., folate and folate analogs), and (ii) $M^3$ and $M^4$ are not each selected from the group consisting of optionally substituted aryl, optionally substituted heteroaryl, and heterosubstituted carbonyl. For example, in one such embodiment, $M^4$ is —C(O)O$M^{40}$, —C(O)S$M^{40}$, —C(O)N$M^{40}M^{41}$, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)O$M^{40}$, —C(O)S$M^{40}$, or —C(O)N$M^{40}M^{41}$, $M^{41}$ is hydrogen, hydrocarbyl, substituted hydrocarbyl, heterohydrocarbyl, substituted heterohydrocarbyl, or heterocyclo, and $M^{40}$ is a substituted hydrocarbyl or a substituted heterohydrocarbyl containing, as a terminal moiety, a targeting moiety selected from the group consisting of bisphosphonate, bisphosphonate analogs, biotin, PSMA inhibitors, peptides, and vitamins (e.g., folate and folate analogs).

In another preferred embodiment, the targeting monomer corresponds to Formula M2, $M^3$ is hydrogen, alkyl or substituted alkyl, and $M^4$ is substituted hydrocarbyl, substituted heterocyclo, or substituted carbonyl, provided, $M^4$ contains as a terminal moiety, a targeting moiety selected from the group consisting of bisphosphonate, bisphosphonate analogs, biotin, PSMA inhibitors, peptides, and vitamins (e.g., folate and folate analogs). For example, in one such embodiment, $M^3$ is hydrogen, methyl, ethyl, or propyl. By way of further example, in one such embodiment $M^3$ is hydrogen, methyl, ethyl, or propyl, $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —C(O)OM$^{40}$ or —C(O)NM$^{40}$M$^{41}$, $M^{41}$ is hydrogen, hydrocarbyl, substituted hydrocarbyl, heterohydrocarbyl, substituted heterohydrocarbyl, or heterocyclo, and $M^{40}$ contains as a terminal moiety, a targeting moiety selected from the group consisting of bisphosphonate, bisphosphonate analogs, biotin, PSMA inhibitors, peptides, and vitamins (e.g., folate and folate analogs). By way of further example, in one such embodiment $M^3$ is hydrogen, methyl, ethyl, or propyl, $M^4$ is —Ar-M$^{40}$ or -Het-M$^{40}$, Ar is arylene, Het is heteroarylene, and $M^{40}$ contains as a terminal moiety, a targeting moiety selected from the group consisting of bisphosphonate, bisphosphonate analogs, biotin, PSMA inhibitors, peptides, and vitamins (e.g., folate and folate analogs).

In one embodiment, the targeting monomer corresponds to Formula M1 or M2 $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains a peptide as a terminal targeting group. In one such embodiment, the peptide is a RGD peptide. In another such embodiment, the peptide is a LOX-1 binding peptide. In another such embodiment, the peptide is an Epidermal Growth Factor (EGF) peptide. In one such embodiment, the peptide is a neurotensin peptide. In one such embodiment, the peptide is a NL4 binding peptide. In one such embodiment, the peptide is a YIGSR laminin peptide. In an alternative embodiment, the monomer corresponds to Formula M1 or M2, $M^4$ is —C(O)OM$^{40}$, —C(O)SM$^{40}$, —C(O)NM$^{40}$M$^{41}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains a bisphosphonate or a bisphosphonate analog as a terminal group. In an alternative embodiment, the monomer corresponds to Formula M1 or M2, $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains biotin as a terminal group. In an alternative embodiment, the monomer corresponds to Formula M1 or M2, $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains a PSMA inhibitor as terminal targeting group. In an alternative embodiment, the monomer corresponds to Formula M1 or M2, $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains folate or a folate analog as a terminal targeting group. In an alternative embodiment, the monomer corresponds to Formula M1 or M2, $M^4$ is —C(O)OM$^{40}$, —C(O)SM$^{40}$, —C(O)NM$^{40}$M$^{41}$, —Ar-M$^{40}$ or -Het-M$^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains as a terminal moiety, a targeting moiety selected from the group consisting of

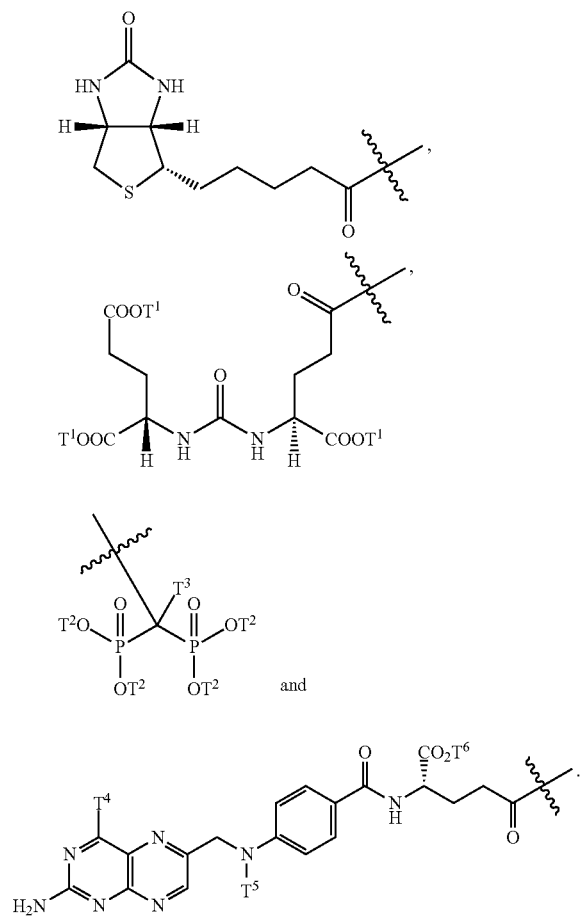

wherein the symbol, ⸻, designates the point of attachment of the targeting moiety to the remainder of $M^{40}$, $T^1$ is hydrogen, alkyl or substituted alkyl; each $T^2$ is independently hydrogen, alkyl, substituted alkyl or trialkylsilyl; $T^3$ is hydrogen, hydrocarbyl, substituted hydrocarbyl, heterohydrocarbyl, substituted heterohydrocarbyl, trialkylsilyl, amino, hydroxy, alkoxy, thiol, thio alkoxy, or halo; $T^4$ is hydroxy, optionally substituted alkoxy, or amino; $T^5$ is hydrogen or alkyl, and $T^6$ is hydrogen or optionally substituted alkyl.

Folate and folate analogs are among the preferred targeting groups. Accordingly, in one preferred embodiment, the targeting monomer corresponds to Formula M10

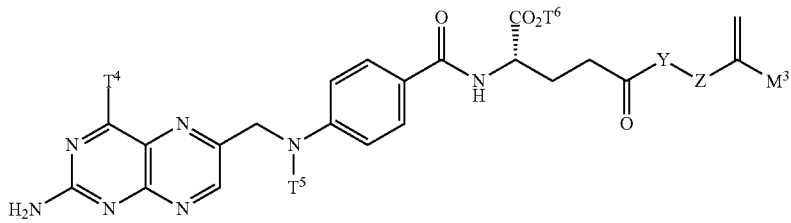

Formula M10 wherein Ar is arylene; Het is heteroarylene; $M^3$ is hydrogen, hydrocarbyl, substituted hydrocarbyl, heterocyclo, or substituted carbonyl; $M^{41}$ is hydrogen, hydrocarbyl, substituted hydrocarbyl, heterohydrocarbyl, substituted heterohydrocarbyl, or heterocyclo; $M^{49}$ is oxygen, sulfur, or —N($M^{50}$)-, $M^{50}$ is hydrogen, hydrocarbyl or substituted hydrocarbyl, Y is a bond or a linking group selected from the group consisting of hydrocarbylene, substituted hydrocarbylene, heterohydrocarbyl, and substituted heterohydrocarbyl; $T^4$ is hydroxy, optionally substituted alkoxy, or amino; $T^5$ is hydrogen or alkyl, $T^6$ is hydrogen, alkyl, substituted alkyl, heterohydrocarbyl, or substituted heterohydrocarbyl; and Z is —C(O)O—, —C(O)S—, —C(O)N($M^{41}$)-, —Ar-$M^{49}$- or Het-$M^{49}$-.

For example, in one such embodiment, $M^3$ is hydrogen, methyl, ethyl, or propyl and $T^4$ is hydroxy. By way of further example, in one such embodiment, $M^3$ is hydrogen, methyl, ethyl, or propyl, $T^4$ is hydroxy, and $T^5$ is hydrogen. By way of further example, in one such embodiment, $M^3$ is hydrogen, methyl, ethyl, or propyl, $T^4$ is hydroxy, and $T^5$ and $T^6$ are hydrogen, By way of further example, in one such embodiment, $M^3$ and $T^6$ are independently hydrogen, methyl, ethyl, or propyl, and Z is —C(O)O—, —C(O)S—, or —C(O)N($M^{41}$)-. By way of further example, in one such embodiment, Y is alkylene or (poly)alkylene oxide. By way of further example, in one such embodiment, $M^3$ and $T^6$ are independently hydrogen, methyl, ethyl, or propyl, Z is —C(O)O—, —C(O)S—, or —C(O)N($M^{41}$)- and Y is alkylene or (poly)alkylene oxide. By way of further example, in one such embodiment, $M^3$ and $T^6$ are independently hydrogen, methyl, ethyl, or propyl, Z is —C(O)O—, —C(O)S—, or —C(O)N($M^{41}$)- and Y is polyethyleneoxide. By way of further example, in one such embodiment, Z is —C(O)O— or —C(O)S— and the targeting monomer corresponds to Formula M11 or M12

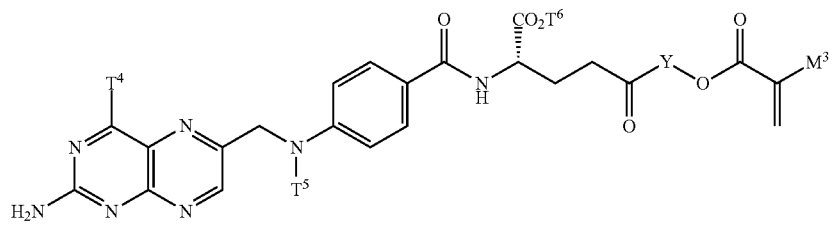

Formula M11

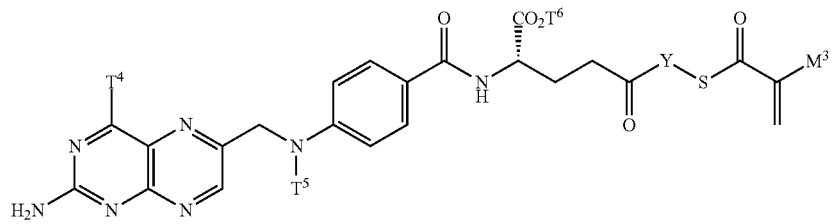

Formula M12 wherein $M^3$ is hydrogen, methyl, ethyl, or propyl, Y is a linking group selected from the group consisting of hydrocarbylene, substituted hydrocarbylene, heterohydrocarbyl, and substituted heterohydrocarbyl; $T^4$ is hydroxy, optionally substituted alkoxy, or amino; $T^5$ is hydrogen or alkyl, and $T^6$ is hydrogen or optionally substituted alkyl. By way of further example, in one such embodiment, Z is —C(O)N($M^{41}$), —Ar-$M^{49}$- or Het-$M^{49}$- and the targeting monomer corresponds to Formula M13, M14 or M15

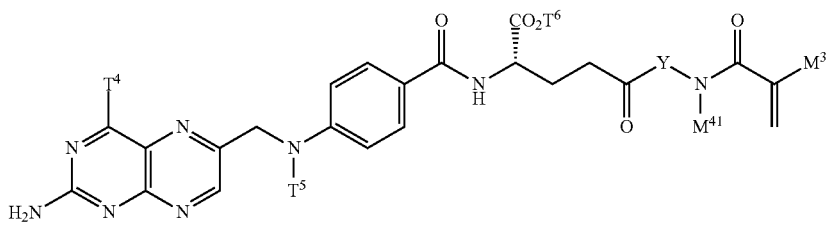

Formula M13

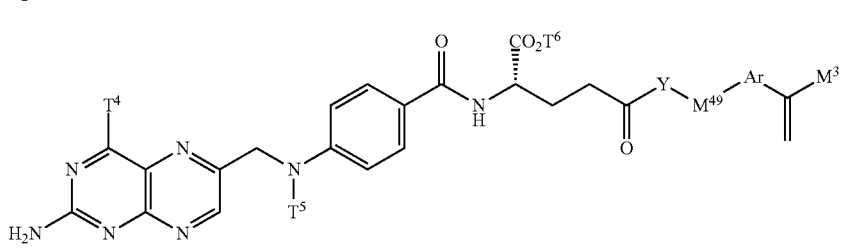

Formula M14

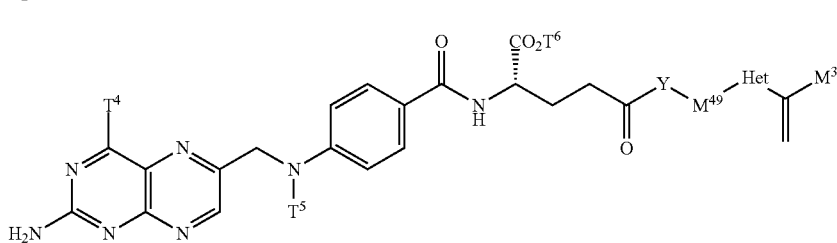

Formula M15 wherein M³ is hydrogen, methyl, ethyl, or propyl, M⁴⁹ is oxygen, sulfur, or —N(M⁵⁰)-, M⁵⁰ is hydrogen, hydrocarbyl or substituted hydrocarbyl, Y is a bond or a linking group selected from the group consisting of hydrocarbylene, substituted hydrocarbylene, heterohydrocarbyl, and substituted heterohydrocarbyl; T⁴ is hydroxy, optionally substituted alkoxy, or amino; T⁵ is hydrogen or alkyl, and T⁶ is hydrogen or optionally substituted alkyl. In each of the foregoing embodiments, Y may be, for example, a (poly)alkylene oxide unit such as (poly)ethylene oxide unit(s). Additionally, in one such embodiment, the targeting monomer corresponds to M11, M12, M13, M14 or M15, and T⁶ is hydrogen or alkyl. By way of further example, in one such embodiment, the targeting monomer corresponds to M11, M12, M13, M14 or M15, and T⁶ is hydrogen, methyl, ethyl, or propyl. By way of further example, in one such embodiment, the targeting monomer corresponds to M11, M12, M13, M14 or M15, T⁴ is hydroxy, and T⁵ is hydrogen. By way of further example, in one such embodiment, the targeting monomer corresponds to M11, M12, M13, M14 or M15, T⁴ is hydroxy and T⁵ and T⁶ are hydrogen.

In another preferred embodiment, the targeting monomer corresponds to Formula M16 wherein n is at least 1; M³ is hydrogen, hydrocarbyl, substituted hydrocarbyl, heterocyclo, or substituted carbonyl; and T⁶ is hydrogen, alkyl, substituted alkyl, heterohydrocarbyl, or substituted heterohydrocarbyl. For example, in one such embodiment, T⁶ is hydrogen or alkyl. By way of further example, in one such embodiment, M³ is hydrogen, methyl, ethyl, or propyl. By way of further example, in one such embodiment, M³ and T⁶ are independently hydrogen, methyl, ethyl, or propyl. By way of further example, in one embodiment, n is 1-10. In one specific embodiment, n is 2-8.

In another preferred embodiment, the targeting monomer corresponds to Formula M17

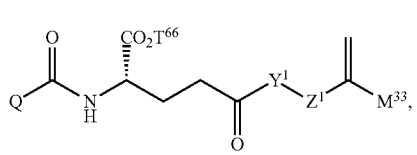

Formula M17 wherein M³³ is hydrogen, hydrocarbyl, substituted hydrocarbyl, heterocyclo, or substituted carbonyl; Y¹ is a bond or a

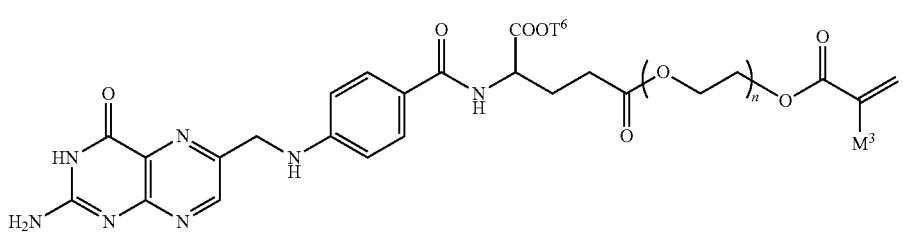

Formula M16 linking group selected from the group consisting of hydrocarbylene, substituted hydrocarbylene, heterohydrocarbyl, and substituted heterohydrocarbyl; $T^{66}$ is hydrogen, alkyl, substituted alkyl, heterohydrocarbyl, or substituted heterohydrocarbyl; and $Z^1$ is —C(O)O—, —C(O)S—, —C(O)N($M^{41}$)-, —Ar-$M^{49}$- or Het-$M^{49}$-; Ar is arylene; Het is heteroarylene; $M^{41}$ is hydrogen, hydrocarbyl, substituted hydrocarbyl, heterohydrocarbyl, substituted heterohydrocarbyl, or heterocyclo; $M^{49}$ is oxygen, sulfur, or —N($M^{50}$)-; $M^{50}$ is hydrogen, hydrocarbyl or substituted hydrocarbyl; the symbol, ⌇ designates the point of attachment; and Q is selected from:

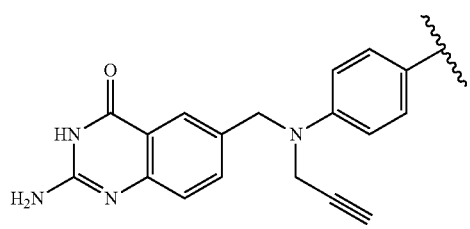

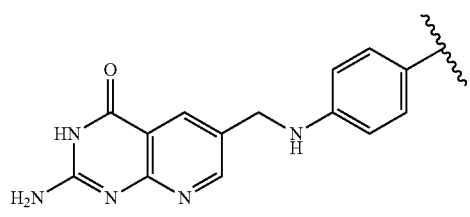

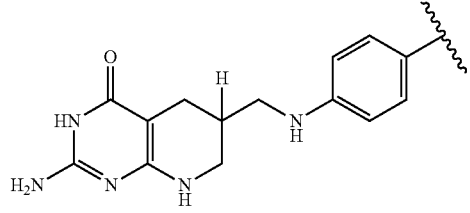

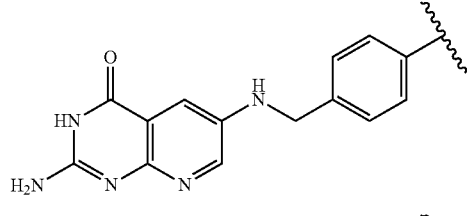

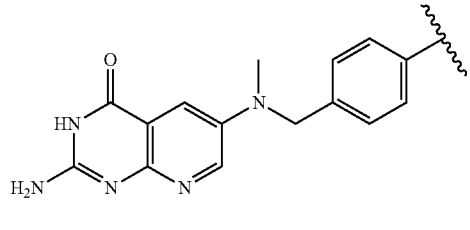

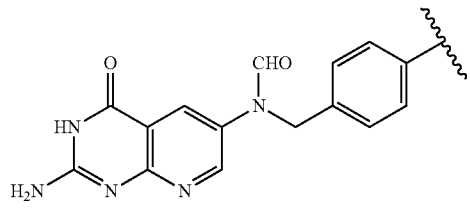

-continued

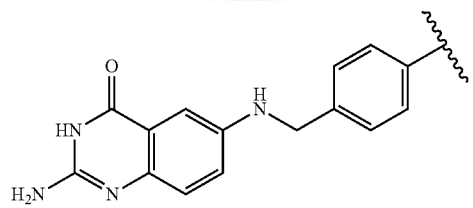

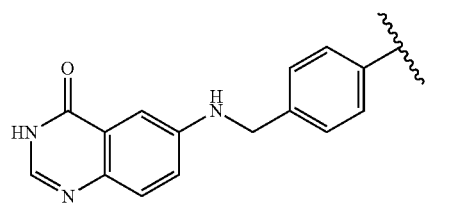

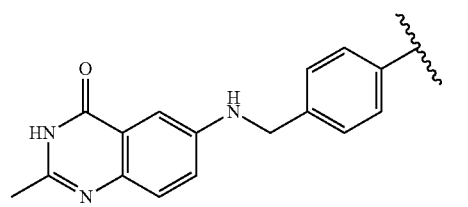

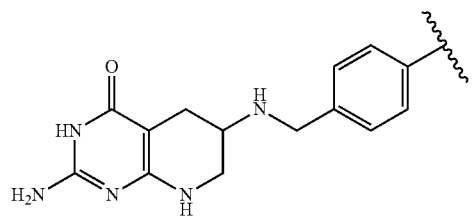

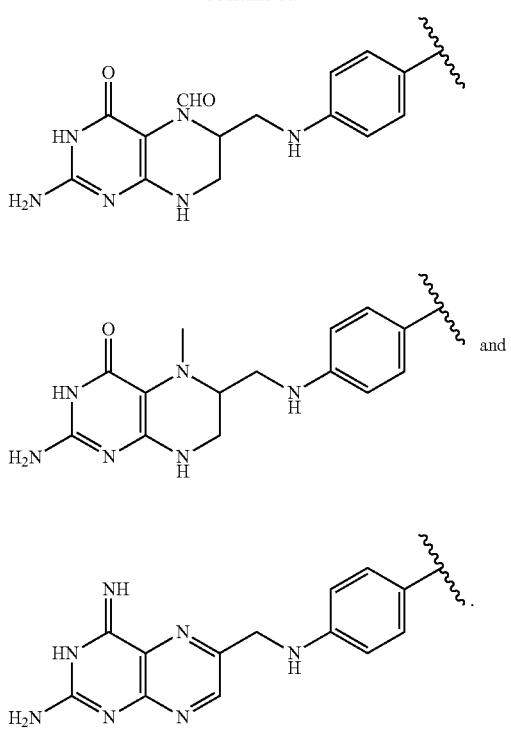

By means of tautomerization, folate (and its analogs) may convert from one isomer to another. Formulae M10-M15 depict one of the tautomers of folate and its analogs, and Formula M16 depicts another. Each of these Formulae, therefore, shall be understood to disclose each such isomer.

Examples of useful PSMA inhibitors include, but are not limited to, the following compounds:

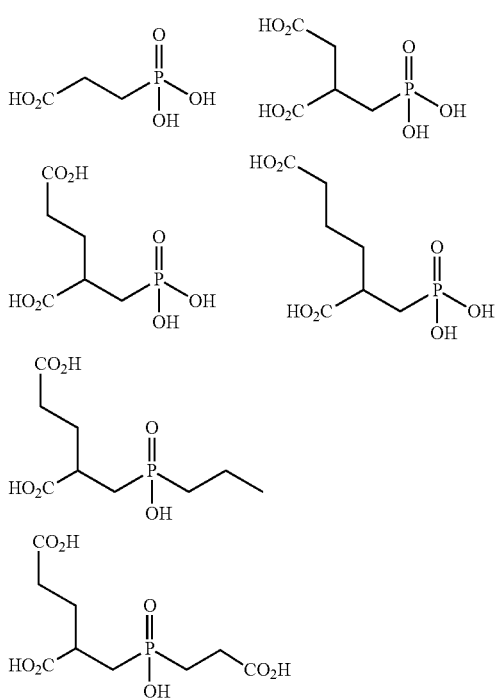

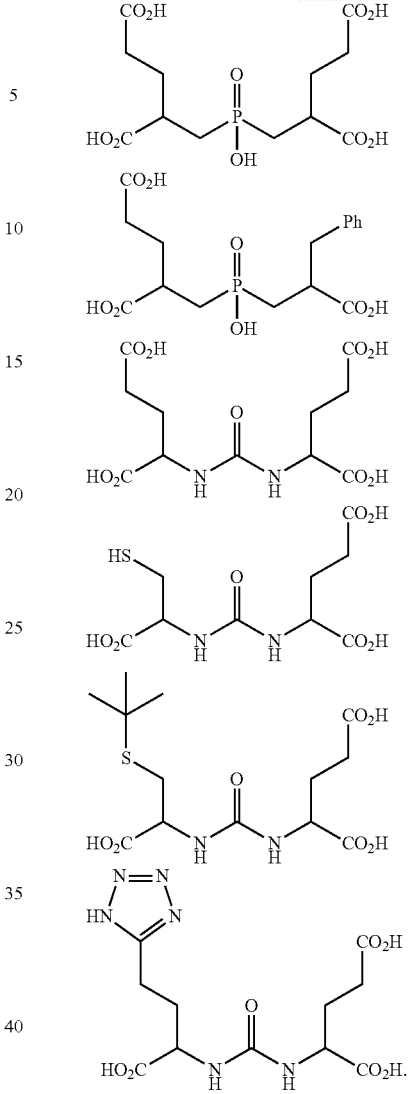

Polymers

In certain embodiments, a targeting monomer of the present invention is polymerized, optionally along with other monomers to form a (co)polymer. Thus, for example, a targeting monomer may be polymerized to form a homopolymer. Alternatively, it may be polymerized to form a block copolymer. For example, the block copolymer may be a monoblock, diblock, triblock, tetrablock or other multiblock copolymer comprising compositionally distinct blocks.

Advantageously, when the polymer is a multiblock copolymer, each of the blocks may possess somewhat different characteristics or provide a somewhat different function to the polymer. For example, in one embodiment, the polymer is a multiblock polymer comprising a targeting block (containing the residue of a targeting monomer of the present invention), optionally one or more (additional) hydrophilic polymeric blocks, and optionally one or more (additional) hydrophobic blocks. For example, the polymer may have a therapeutic agent attached (covalently or non-covalently) to a block thereof (hydrophilic or hydrophobic) and the polymer may comprise a hydrophobic membrane destabilizing block. Advantageously, such polymers may be used to form micelles and/or deliver therapeutic agents.

In a preferred embodiment, the targeting block (containing a targeting monomer of the present invention) is a hydrophilic block and the multiblock copolymer comprises at least one additional compositionally distinct hydrophilic block. The additional hydrophilic block(s) may be used, for instance, to contribute water solubility to the copolymer, to aid in micelle formation, to enhance the targeting of the copolymer to a cellular or other biological target, to shield a therapeutic agent that is associated with the copolymer, or a combination of two or more thereof. Optionally, the polymer may contain a second, compositionally distinct hydrophilic block, that complements the targeting block and the other hydrophilic block by providing a property or function not provided by the targeting or other hydrophilic block; for example, the second hydrophilic block may be used to provide means for attaching a therapeutic agent, contribute water solubility to the copolymer, aid in micelle formation, further target the copolymer to a cellular or other biological target, shield a therapeutic agent that is associated with the copolymer, or a combination of two or more thereof. Alternatively, or additionally, the polymer may comprise, a hydrophobic block to decrease the water solubility of the copolymer, aid in micelle formation, carry a therapeutic agent, destabilize a cellular membrane or other biological target, or a combination of two or more thereof. The copolymer may optionally possess further additional polymeric blocks that amplify the function of the copolymers of the present invention, or which introduce other functionalities or properties to the copolymer.

Regardless of the number of blocks, it is generally preferred that the number average molecular weight of the polymeric blocks, in combination, be about 5,000 to about 100,000 daltons. Additionally, in one embodiment, the Zeta potential of a polymeric solution containing a block polymer of the present invention (without an associated therapeutic agent such as a polynucleotide) is between ±6 mV (millivolt). In one preferred embodiment, the Zeta potential of the polymeric solution (without an associated therapeutic agent such as a polynucleotide) is between ±5 mV. In one preferred embodiment, the Zeta potential of the polymeric solution (without an associated therapeutic agent such as a polynucleotide) is between ±2 mV.

In one preferred embodiment, a targeting monomer of the present invention is copolymerized with other compositionally distinct monomers to form a copolymer block of a monoblock or multiblock polymer. For example, in one embodiment, the monomer is incorporated into a diblock polymer, the diblock polymer comprising a targeting block (containing residues of a targeting monomer corresponding to Formula M1) and a membrane destabilizing hydrophobic polymer block. In another embodiment, the monomer is incorporated into a triblock polymer wherein the targeting monomer is incorporated into a first, targeting block, the second block is a carrier block to which a polynucleotide or other therapeutic agent is or may be attached, and the third block is a hydrophobic block. In each of these embodiments, it is generally preferred that the targeting block be a hydrophilic block.

When the polymer comprises at least two compositionally distinct polymer blocks, the blocks may be covalently coupled via a polymeric or non-polymeric linking moiety. For example, when the polymer comprises a hydrophilic block in addition to the hydrophobic block, the hydrophilic block may be coupled to the hydrophobic block by a series of amino acid residues, saccharide residues, nucleic acid residues, etc., to introduce a cleavage point or other functionality between the respective blocks. By way of further example, the blocks may be covalently coupled by a cleavable moiety such as a disulfide, a hydrazide, an ester, an acetal, or a phosphodiester linking moiety. In general, it is presently preferred that the hydrophilic block, when present, be immediately adjacent to the hydrophobic block.

In general, when the polymer is a multiblock polymer, it is preferred that at least one of the polymer block(s) be a copolymer block and, still more preferred that at least one of polymer block(s) be a random copolymer block. Thus, for example, it is generally preferred that a hydrophobic block be a random copolymer comprising two or more compositionally distinct monomeric residues. When the polymer additionally comprises a hydrophilic block, the hydrophilic block or the hydrophobic block may be a random copolymer block comprising two or more compositionally distinct monomeric residues; in this embodiment, the hydrophilic block, the hydrophobic block or both of the hydrophobic and hydrophilic blocks may be a random copolymer block comprising two or more compositionally distinct monomeric residues. Additionally, when the polymer comprises at least two compositionally distinct hydrophilic blocks, the hydrophobic block or at least one of the hydrophilic blocks may be a random copolymer block comprising two or more compositionally distinct monomeric residues; in this embodiment, at least one of the hydrophilic blocks, the hydrophobic block or each of the hydrophobic and hydrophilic blocks may be a random copolymer block comprising two or more compositionally distinct monomeric residues. Additionally, when the polymer comprises at least two compositionally distinct hydrophobic blocks, at least one of the hydrophobic blocks may be a random copolymer block comprising two or more compositionally distinct monomeric residues. Additionally, when the polymer comprises at least two compositionally distinct hydrophobic blocks and a hydrophilic block, at least one of the hydrophobic blocks or the hydrophilic block may be a random copolymer block comprising two or more compositionally distinct monomeric residues. In some embodiments, the first (and/or second) hydrophilic block may be a homopolymer block(s). For example, in one embodiment, the polymer comprises a first hydrophilic block, the first hydrophilic block is a homopolymer and the first hydrophobic block is a random copolymer block. By way of further example, in one embodiment, the polymer comprises first and second hydrophilic blocks, the first and second hydrophilic blocks are compositionally distinct homopolymers and the hydrophobic block is a random copolymer. By way of further example, in one embodiment, the polymer comprises first and second hydrophilic blocks, one of the first and second hydrophilic blocks is a homopolymer and the other hydrophilic block and the hydrophobic block are random copolymer blocks. By way of yet further example, in one embodiment, each of the polymer blocks, hydrophilic or hydrophobic are compositionally distinct random copolymers.

The hydrophobic block and, optionally, other polymeric blocks, when present, comprise chain atoms and pendant groups covalently coupled to the chain atoms. Preferably, the chain atoms are carbon or a combination of (i) carbon and (ii) sulfur and/or oxygen atoms. Thus, for example, the repeat units of the hydrophobic polymer block, and optionally one or more other polymeric blocks, when present, are independently selected from the group consisting of substituted alkylene, substituted alkylene glycol, and substituted alkylene thioglycol repeat units, and combinations thereof. In one preferred embodiment, the chain atoms of the hydrophobic polymer block, and optionally one or more other polymeric blocks, when present, are carbon. In another embodiment, the polymer comprises a hydrophobic block and a hydrophilic block and the chain atoms of the hydrophobic and hydrophilic blocks are independently carbon or a combination of carbon, oxygen and sulfur atoms. Independent of the selection of the chain atoms, the pendant groups are preferably selected from the group consisting of hydrogen, hydrocarbyl, substituted hydrocarbyl, substituted carbonyl and heterocyclo.

In a preferred embodiment, the hydrophobic block of the polymer of the present invention is prepared by a method other than by stepwise coupling approaches involving a sequence of multiple individual reactions (e.g., such as known in the art for peptide synthesis or for oligonucleotide synthesis). For example, in one embodiment, the hydrophobic block is formed by chain-growth polymerization, sometimes referred to as addition polymerization. By way of further example, in one embodiment, the polymer comprises at least one other polymer block in addition to the hydrophobic block and at least two of the polymer blocks are formed by chain-growth polymerization. By way of further example, in one embodiment, each of the polymer blocks is formed by chain-growth polymerization.

Although each of the blocks may contain repeat units linked by amide bonds, formed for example, by the condensation reaction of amino acids or by the condensation reaction of species other than amino acids (e.g., diamines and dicarboxylic acids), it is generally preferred that the substantial majority of the residues constituting the hydrophobic block and the hydrophilic block (when present) not be peptidic. Stated differently, it is generally preferred that the substantial majority of the residues of the hydrophobic block and the hydrophilic block, when present, be other than amino acid residues linked by peptide bonds. For example, in one embodiment at least 90% of the residues constituting the hydrophilic block are other than amino acid residues linked by peptide bonds. By way of further example, in one embodiment the polymer comprises a second hydrophobic polymer block and at least 90% of the residues constituting the second hydrophobic block are other than amino acid residues linked by peptide bonds. By way of further example, in one embodiment the polymer comprises a hydrophilic block and at least 90% of the residues constituting the hydrophilic block are other than amino acid residues linked by peptide bonds. By way of further example, in one embodiment it is preferred that at least 90% of the residues constituting each of the blocks be other than amino acid residues linked by peptide bonds. Preferably, each block is a substantially non peptidic polymer (consists of a polymer other than an amino acid polymer).

In contrast, for clarity, notwithstanding and without prejudice to the foregoing, the targeting moieties and/or other biomolecular agents of the inventions can be an amino acid polymer (e.g., a peptide) or a nucleic acid polymer (e.g., an oligonucleotide) or a polysaccharide. In one preferred embodiment, peptides, saccharides, or nucleic acid residues are attached, as pendant groups, to the repeat units to increase water solubility, to provide shielding, to provide targeting, or as therapeutic agents. When attached as pendant groups, however, the peptides, saccharides, and nucleic acids do not provide peptide, glycosidic or phosphodiester bonds along the backbone of the polymer block which they would do if incorporated as repeat units.

Conveniently, the polymers or polymer blocks may be prepared from readily polymerizable monomers. For example, in one embodiment, the repeat units are residues of ethylenically unsaturated monomer(s). In another, the hydrophobic block and other blocks, when present, comprise repeat units independently derived from optionally substituted acrylic acid monomers, optionally substituted vinyl aryl monomers, optionally substituted acrylamide monomers, optionally substituted acrylate monomers and combinations thereof.

Hydrophobic Blocks

In general, the hydrophobic block, when present, may optionally comprise, as a pendant group, a therapeutic agent such as a polynucleotide. The therapeutic agent may be a pendant group on the monomer prior to the polymerization and incorporation of the monomeric residue as a repeat unit. Alternatively, the monomer may contain a conjugatable pendant group that may be derivatized to covalently couple the therapeutic agent post-polymerization. In some instances, a conjugatable pendant group is a moiety bearing one or more reactive groups that can be used for post-polymerization introduction of additional functionalities via known in the art chemistries (such as the techniques described in Hermanson, G. T., Bioconjugate Techniques, 2nd ed. (Pierce Biotechnology, Thermo Fisher Scientific, Rockford, Ill.). Academic Press (an imprint of Elsevier): London, Amsterdam, Burlington, San Diego. 2008. 1202 pp.), for example, "click" chemistry (for example of "click" reactions, see Wu, P.; Fokin, V. V. Catalytic Azide-Alkyne Cycloaddition: Reactivity and Applications. Aldrichim. Acta, 2007, 40, 7-17). In certain embodiments, conjugatable side chains provided herein comprise one or more of any suitable electrophilic or nucleophilic functional group, such as but not limited to N-hydroxysuccinimide (NHS)ester, HOBt (1-hydroxybenzotriazole) ester, p-nitrophenyl ester, tetrafluorophenyl ester, pentafluorophenyl ester, pyridyl disulfide group, maleimide, aldehyde, ketone, anhydride, thiol, amine, hydroxyl, alkyl halide, or the like.

Alternatively, or additionally, the hydrophobic block may also comprise repeat units having pendant groups selected from the group consisting of hydrophobic species, cationic species, anionic species, zwitterionic species and non-charged hydrophilic species. In general, different repeat units in the hydrophobic block may independently comprise one or more of these species. For example, some repeat units may comprise only hydrophobic species. Other repeat units may comprise only cationic species. Other repeat units may comprise only zwitterionic species. Other repeat units may comprise only anionic species. Still others may comprise an anionic species and a hydrophobic species on the same, individual repeat unit. Still others may comprise a cationic species and a hydrophobic species on the same, individual repeat unit.

In one embodiment, the hydrophobic block comprises a population of repeat units having pendant hydrophobic species (used interchangeably herein with "hydrophobicity enhancers"). Exemplary hydrophobic species include optionally-substituted alkyl, alkaryl such as aryl-alkyl, alkyl-aryl, and alkyl-aryl-alkyl, heteroalkyl, aryl, and heteroaryl. In specific embodiments, the hydrophobic species is optionally substituted alkyl, alkaryl, or aryl. In some embodiments, hydrophobic block comprises a population of monomeric residues having pendant hydrophobic species selected from $(C_2-C_8)$alkyl, $(C_2-C_8)$alkenyl, $(C_2-C_8)$alkynyl, aryl, and heteroaryl, each of which may be optionally substituted. In certain embodiments, the population of monomeric residues can be derived from polymerization of $(C_2-C_8)$alkyl ethacrylate, a $(C_2-C_8)$alkyl methacrylate, or a $(C_2-C_8)$alkyl acrylate (each of which may be optionally substituted).

In a preferred embodiment, the hydrophobic block comprises anionic repeat units having a population of pendant anions that vary in number in a pH dependant manner. In general, the population of pendant anions is greater at pH 7.4 than at pH 5. In general, it is preferred that at least 90% of the population of these pH-sensitive anionic repeat units are non-charged at about pH 5. For example, in one such preferred embodiment, at least 99% of the population of these pH-sensitive anionic repeat units are non-charged at about pH 5. By way of further example, in one such embodiment the anionic repeat units comprise pendant groups that are in the form of carboxyl anions at pH 7.4 and carboxylic acids at pH 5.

It is also preferred that the hydrophobic block comprise a substantial number of anionic repeat units having a population of pendant anions that vary in number in a pH dependant manner. For example, in one embodiment, the hydrophobic block comprises at least 10 such residues. In another embodiment, it comprises as least 20 such residues. In another embodiment, it comprises at least 50 such residues. In another embodiment, it comprises at least 100 such residues. In such embodiments, the hydrophobic block will typically comprise about 10 to about 500 anionic residues.

In some preferred embodiments, the hydrophobic block comprises a population of anionic hydrophobic monomeric residues, i.e., monomeric residues comprising both hydrophobic species (e.g., a $C_2$-$C_8$ alkyl substituent) and species charged or chargeable to an anion. In each of such aforementioned embodiments, the hydrophobic block can be considered hydrophobic in the aggregate.

In general, therefore, the hydrophobic block may contain anionic repeat units, cationic repeat units, zwitterionic repeat units, a combination of two or more charged repeat units (e.g., anionic and cationic repeat units, anionic and zwitterionic repeat units, cationic and zwitterionic repeat units, or anionic, cationic and zwitterionic repeat units), substantially non-charged repeat units, or a combination thereof, provided that its overall character is hydrophobic. Stated differently, the hydrophobic block may contain any of a wide range of repeat units, hydrophobic or even hydrophilic, provided that the sum of the contributions of the repeat units comprised by the hydrophobic block provide a block having an overall hydrophobic character. When the repeat units contain ionizable groups, the contribution of an individual repeat unit to the overall hydrophilicity of the block of which it is a constituent may vary as a function of its pKa relative to the pH of the environment in which it is found. For example, propyl acrylic acid repeat units, —$CH_2C(CH_2CH_2CH_3)(COOH)$—, are predominantly ionized at pH 7 but not at pH 5 and thus, the hydrophobic contribution of propyl acrylic acid repeat units to a block is significantly greater at pH 5 than at pH 7. In general, therefore, it is preferred that the sum of the contributions of the repeat units constituting the hydrophobic block be such that the overall character of the block is hydrophobic at pH's that are less than physiological pH. For example, in one embodiment, the sum of the contributions is such that the overall character of the block is hydrophobic at a pH of about 5.0. By way of further example, in one embodiment, the sum of the contributions is such that the overall character of the block is hydrophobic at a pH of about 5.5. By way of further example, in one embodiment, the sum of the contributions is such that the overall character of the block is hydrophobic at a pH of about 6.0. By way of further example, in one embodiment, the sum of the contributions is such that the overall character of the block is hydrophobic at a pH of about 6.8. By way of further example, in one embodiment, the sum of the contributions of the repeat units is such that the overall character of the hydrophobic block is hydrophobic at a pH within the range of about 6.2 to 6.8.

In certain embodiments, a hydrophobic block described herein comprises monomeric residues resulting from the polymerization or copolymerization of a monomer comprising a hydrophobic species. Monomers comprising a hydrophobic species include, by way of non-limiting example, optionally substituted, ($C_2$-$C_8$)alkyl-ethacrylate, a ($C_2$-$C_8$) alkyl-methacrylate, a ($C_2$-$C_8$)alkyl-acrylate, styrene, ($C_2$-$C_8$) alkyl-vinyl, or the like. In certain embodiments, monomers comprising a hydrophobic species include, by way of non-limiting example, monomers of Formula VI:

(VI)

wherein:

$R^1$ and $R^2$ are each independently hydrogen, halogen, optionally substituted $C_1$-$C_6$ alkyl, optionally substituted alkenyl, optionally substituted alkynyl, optionally substituted cycloalkyl, optionally substituted aryl, or optionally substituted heteroaryl;

$R^3$ is hydrogen, halogen, optionally substituted $C_1$-$C_6$ alkyl, or —$C(=O)R^5$;

$R^4$ is hydrogen, halogen, optionally substituted $C_1$-$C_6$ alkyl;

$R^5$ is optionally substituted $C_1$-$C_6$ alkyl, —$SR^6$, —$OR^6$, or —$NR^7R^8$;

$R^6$ is hydrogen, optionally substituted $C_1$-$C_6$ alkyl, optionally substituted alkenyl, optionally substituted alkynyl, optionally substituted cycloalkyl, optionally substituted aryl, or optionally substituted heteroaryl;

$R^7$ and $R^8$ are each independently hydrogen, optionally substituted alkyl, optionally substituted heteroalkyl, optionally substituted cycloalkyl, optionally substituted aryl; or $R^7$ and $R^8$ together with the nitrogen to which they are attached form an optionally substituted heterocycle.

In certain embodiments, in addition to a hydrophobic species, a hydrophobic block described herein further comprises an anionic species. In specific embodiments, the anionic species is anionic at about neutral pH. In specific embodiments, the hydrophobic block comprises a first monomer residue comprising a hydrophobic species and a second monomer residue comprising an anionic species.

In certain embodiments, a hydrophobic block described herein comprises a polymer block comprising a plurality of hydrophobic monomeric residues and a plurality of anionic monomeric residues. In some embodiments, a hydrophobic block described herein comprises a polymer block comprising a plurality of chargeable residues. In some embodiments, monomeric residues that are anionic, (1) are anionic at about neutral pH, a pH greater than about 7.2, or any pH greater than about 7.4, and (2) are non-charged at a pH of less than about 6, less than about 5.8, less than about 5.7, less than about 5.6, less than about 5.5, less than about 5.4, less than about 5.2, less than about 5.0, or less than about 4.5. In some embodiments, the monomeric residues have a pKa anywhere between about 4.5 and about 8.0, anywhere between about 5.5 and about 7.5, or anywhere between about 6.0 and about 7.0. In certain embodiments, monomers that when polymerized provide the anionic monomeric residues have a pKa anywhere between about 4.5 and about 8.0, anywhere between about 5.5 and about 7.5, or anywhere between about 6.0 and about 7.0.

In specific embodiments, anionic species which may be found on anionic monomeric residues described herein include, by way of non-limiting example, carboxylic acid, sulfonamide, boronic acid, sulfonic acid, sulfinic acid, sulfuric acid, phosphoric acid, phosphinic acid, and phosphorous acid groups, or the conjugate bases or anions thereof. In some embodiments, the anionic monomeric residue is a residue of ($C_1$-$C_8$)alkylacrylic acid, or acrylic acid. In certain embodiments monomers such as maleic-anhydride, (Scott M. Henry, Mohamed E. H. El-Sayed, Christopher M. Pirie, Allan S. Hoffman, and Patrick S. Stayton, pH-Responsive Poly(styrene-alt-maleic anhydride) Alkylamide Copolymers for Intracellular Drug Delivery. *Biomacromolecules* 2006, 7, 2407-2414) are used for introduction of anionic species by post-polymerization hydrolysis of the maleic anhydride monomeric units.

In certain embodiments, in addition to a hydrophobic species, a hydrophobic block described herein further comprises a cationic species. In some embodiments, in addition to a hydrophobic species and an anionic species, a hydrophobic block described herein further comprises a cationic species. In certain embodiments, in addition to a hydrophobic monomeric residue, a hydrophobic block described herein further comprises a cationic monomeric residue. In some embodiments, in addition to a hydrophobic monomeric residue and an anionic monomeric residue, a hydrophobic block described herein further comprises a cationic monomeric residue. In some embodiments, species and/or monomeric residues that are cationic are cationic at about neutral pH.

In some embodiments, a cationic monomeric residues described herein has a pKa ranging anywhere between about 6.0 and about 10.0, typically between about 6.2 and about 9.5, and in some embodiments between about 6.5 and about 8.5. Upon incorporation of the monomer into the polymer block, the pKa of the residue tends to decrease relative to the unpolymerized monomer; in general, therefore, the pKa of the incorporated repeat units will be between about 6.0 and 10.0, typically between about 6.2 and 9.0, and in some embodiments, between about 6.5 and 8.0

In certain embodiments, the hydrophobic block comprises a monomeric species comprising an acyclic amine (e.g., an amine, an alkyl amine, a dialkyl amine, or the like), an acyclic imine (e.g., an imine, an alkyl imine, or the like), a cyclic amine (e.g., piperidine), a nitrogen containing heterocycle (e.g., pyridine or quinoline), or the like. In specific embodiments, a cationic species utilized herein includes a protonated acyclic amine (e.g., an amine, an alkyl amine, a dialkyl amine, or the like), an acyclic imine (e.g., an imine, an alkyl imine, or the like), a cyclic amine (e.g., piperidine), a nitrogen containing heterocycle (e.g., pyridine or quinoline), or the like.

Non-limiting examples of acyclic amines include methylamine, dimethylamine, ethylamine, diethylamine, propylamine, isopropylamine, diisopropylamine, diisopropylethylamine, n-butylamine, sec-butylamine, tert-butylamine, pentylamine, neo-pentylamine, iso-pentylamine, hexanamine or the like. Non-limiting examples of acyclic imines include methylimine, ethylimine, propylimine, isopropylimine, n-butylimine, sec-butylimine, pentylimine, neo-pentylimine, iso-pentylimine, hexylimine or the like. Non-limiting examples of cyclic amines include cyclopropylamine, cyclobutylamine, cyclopentylamine, cyclohexylamine, cycloheptylamine, piperidine, pyrazine, pyrrolidine, homopiperidine, azabicylcoheptane, diazabicycloundecane, or the like. Non-limiting examples of cyclic imines include cyclopropylimine, cyclobutylimine, cyclopentylimine, cyclohexylimine, cycloheptylimine, or the like. Non-limiting examples of nitrogen containing heteroaryls include imidazolyl, pyrrolyl, pyridyl, indolyl, or the like.

In some embodiments, a hydrophobic block of a polymer described herein comprises a plurality of monomeric residues of optionally substituted, amino($C_1$-$C_6$)alkyl-ethacrylate, amino($C_1$-$C_6$)alkyl-methacrylate, amino($C_1$-$C_6$)alkyl-acrylate, (N—($C_1$-$C_6$)alkyl-amino($C_1$-$C_6$)alkyl-ethacrylate, N—($C_1$-$C_6$)alkyl-amino($C_1$-$C_6$)alkyl-methacrylate, N—($C_1$-$C_6$)alkyl-amino($C_1$-$C_6$)alkyl-acrylate, (N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or a combination thereof. In specific embodiments, such monomeric residues constitute a cationic monomeric residue at neutral pH as described herein.

In certain embodiments, a hydrophobic block described herein comprises a plurality of anionic monomeric residues, a plurality of cationic monomeric residues, and a plurality of hydrophobic monomeric residues.

In certain specific embodiments, at about neutral pH (e.g., at about pH 7.4), the hydrophobic block has a substantially neutral overall charge. In still more specific embodiments, a substantially neutral overall charge of the hydrophobic block means that at least 60%, at least 70%, at least 80%, at least 90%, at least 95%, or at least 98% of the charge of either of the cationic monomeric residues or the anionic monomeric residues are neutralized by the charge of the of the other of the cationic monomeric residues or the anionic monomeric residues. In other words, in various embodiments, the ratio of the number of monomeric units in the hydrophobic block that are cationic at about neutral pH to the number of monomeric units in the hydrophobic block that are anionic at about neutral pH is between about 3:5 and about 5:3, about 7:10 and about 10:7, about 4:5 and about 5:4, about 9:10 and about 10:9, about 95:100 and about 100:95, or about 98:100 and about 100:98. Determination of charge ratios can be achieved in any suitable manner, e.g., by calculating the amount of charged species using the pKa and/or pKb values thereof.

In some embodiments, at about neutral pH (e.g., at about pH 7.4), the hydrophobic block comprises anionic species and cationic species in a ratio of about 10:1 to about 1:10, about 5:1 to about 1:5, about 4:1 to about 1:4, about 1:0 to about 1:4 (anionic species:cationic species). In a preferred embodiment, at about neutral pH (e.g., at about pH 7.4), the hydrophobic block comprises anionic species and cationic species in a ratio of about 1:1 (anionic species:cationic species). In some embodiments, at about neutral pH (e.g., at about pH 7.4), the hydrophobic block comprises anionic monomeric residues and cationic monomeric residues in a ratio of about 1:0 to about 1:4 (anionic monomeric residues: cationic monomeric residues). In a preferred embodiment, at about neutral pH (e.g., at about pH 7.4), the hydrophobic block comprises anionic monomeric residues and cationic monomeric residues in a ratio of about 1:1 (anionic monomeric residues:cationic monomeric residues).

In certain embodiments, at about neutral pH (e.g., at about pH 7.4), the hydrophobic block comprises hydrophobic monomeric residues, cationic monomeric residues, and anionic monomeric residues. In specific embodiments, the ratio of hydrophobic monomeric residues to charged monomeric residues (cationic monomeric residues plus anionic monomeric residues), is about 1:5 to about 5:1, or about 1:3 to about 3:1, or about 1:2 to about 3:1, or about 1:1, or about 1:2, or about 2:1.

In certain embodiments, a hydrophobic block, as described herein comprises a plurality of first monomeric residues derived from a first polymerizable monomer having a protonatable anionic species and a hydrophobic species, and optionally a plurality of second monomeric residues derived from a second polymerizable monomer having a deprotonatable cation species.

In one preferred embodiment, the hydrophobic block comprises repeat units corresponding to Formula 1

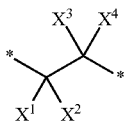

Formula 1 wherein * designates the point of attachment of the repeat unit of Formula 1 to other repeat units; each $X^1$ and $X^2$ is independently selected from the group consisting of hydrogen, hydrocarbyl, substituted hydrocarbyl, heterocyclo, and substituted carbonyl, provided, however, $X^1$ and $X^2$ are not, in the same repeat unit, selected from the group consisting of aryl, heteroaryl, heterosubstituted carbonyl, and combinations thereof; each $X^3$ is independently hydrogen, alkyl or substituted alkyl, and each $X^4$ is independently heterosubstituted carbonyl, aryl, or heteroaryl. For example, in one such embodiment the hydrophobic block comprises repeat units corresponding to Formula 1 and $X^1$ and $X^2$ are each hydrogen. In another such example, the hydrophobic block comprises repeat units corresponding to Formula 1, $X^1$ and $X^2$ are each hydrogen and $X^3$ is hydrogen or alkyl. In a further example, the hydrophobic block comprises repeat units corresponding to Formula 1, $X^1$ and $X^2$ are each hydrogen, $X^3$ is hydrogen or alkyl, and each $X^4$ is independently heterosubstituted carbonyl. In a further example, the hydrophilic block comprises repeat units corresponding to Formula 1, $X^4$ is —C(O)O$X^{40}$, —C(O)S$X^{40}$, or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In a further example, the hydrophobic block comprises repeat units corresponding to Formula 1, $X^4$ is —C(O)O$X^{45}$, —C(O)S$X^{45}$, or —C(O)N$X^{41}X^{45}$, and $X^{41}$ and $X^{45}$ are independently hydrogen, hydrocarbyl, substituted hydrocarbyl, heterohydrocarbyl, or heterocyclo. In a further example, the hydrophobic block comprises repeat units corresponding to Formula 1, $X^4$ is —C(O)O$X^{45}$ or —C(O)N$X^{41}X^{45}$, and $X^{41}$ and $X^{45}$ are independently hydrocarbyl, heterohydrocarbyl, or heterocyclo. In a further example, the hydrophobic block comprises repeat units corresponding to Formula 1, $X^1$ and $X^2$ are each hydrogen, $X^3$ is hydrogen or alkyl, $X^4$ is —C(O)O$X^{45}$, and $X^{45}$ is hydrogen, hydrocarbyl, substituted hydrocarbyl, heterohydrocarbyl, substituted heterohydrocarbyl, or heterocyclo. In a further example, the hydrophobic block comprises repeat units corresponding to Formula 1, $X^1$ and $X^2$ are each hydrogen, $X^3$ is hydrogen or alkyl, $X^4$ is —C(O)O$X^{45}$, $X^{45}$ is a disulfide substituted alkyl moiety (for example, pyridyl disulfide substituted ethyl). In a further example, the hydrophobic block comprises repeat units corresponding to Formula 1, $X^1$ and $X^2$ are each hydrogen, $X^3$ is hydrogen or alkyl, $X^4$ is —C(O)N$X^{41}X^{45}$, $X^{41}$ is hydrogen, and $X^{45}$ is alkyl or substituted alkyl.

In one alternative embodiment, the hydrophobic block is a random copolymer comprising at least two compositionally distinct repeat units, each of which corresponds to Formula 1. For example, the hydrophobic block may be a random copolymer comprising (i) a first repeat unit corresponding to Formula 1 in which $X^4$ is —C(O)O$X^{45}$ and (ii) a second repeat unit corresponding to Formula 1 in which $X^4$ is —C(O)N$X^{41}X^{45}$. Advantageously, when the hydrophobic block is a random copolymer comprising at least two compositionally distinct repeat units, one of the repeat units may provide a functional group for attaching a therapeutic agent such as a nucleic acid. Thus, for example, the hydrophobic block may comprise (i) a first repeat unit corresponding to Formula 1 wherein $X^4$ is —C(O)O$X^{45}$, —C(O)S$X^{45}$, or —C(O)N$X^{41}X^{45}$ and a therapeutic agent such as a nucleic acid is attached to the hydrophobic block via $X^{45}$ or $X^{45}$ comprises a functional group for attaching the therapeutic agent, and (ii) a compositionally distinct repeat unit corresponding to Formula 1. For example, $X^{45}$ may be an alkyl group substituted by N-hydroxysuccinimide (NHS)ester, HOBt (1-hydroxybenzotriazole) ester, p-nitrophenyl ester, tetrafluorophenyl ester, pentafluorophenyl ester, pyridyl disulfide group, maleimide, aldehyde, ketone, anhydride, thiol, amine, hydroxyl, alkyl halide, or the like.

In one preferred embodiment, the hydrophobic block comprises repeat units corresponding to Formula 1A

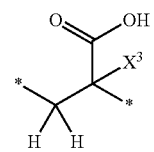

Formula 1A wherein * designates the point of attachment of the repeat unit of Formula 1A to other repeat units; and $X^3$ is alkyl. Exemplary alkyls include methyl, ethyl, propyl and butyl. Typically, $X^3$ is ethyl or propyl. In a preferred embodiment, $X^3$ is propyl. It is also preferred that the hydrophobic block comprise a substantial number of anionic repeat units corresponding to Formula 1A. For example, in one embodiment, the hydrophobic block comprises at least 10 such residues. In another embodiment, it comprises as least 20 such residues. In another embodiment, it comprises at least 50 such residues. In another embodiment, it comprises at least 100 such residues. In such embodiments, the hydrophobic block will typically comprise about 10 to about 500 anionic residues.

In one preferred embodiment, the hydrophobic block comprises repeat units corresponding to Formula 1E

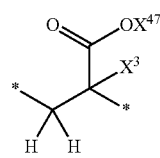

Formula 1E wherein * designates the point of attachment of the repeat unit of Formula 1E to other repeat units; and $X^3$ and $X^{47}$ are independently alkyl. Exemplary alkyls include methyl, ethyl, propyl and butyl. Typically, $X^3$ is methyl, ethyl or propyl and $X^{47}$ is independently methyl, ethyl, propyl or butyl. In one preferred embodiment, $X^3$ is methyl and $X^{47}$ is butyl.

In one preferred embodiment, the hydrophobic block comprises repeat units corresponding to Formula 1C

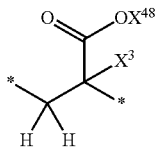

Formula 1C wherein * designates the point of attachment of the repeat unit of Formula 1C to other repeat units; $X^3$ is alkyl, and $X^{48}$ is amino-substituted alkyl. Exemplary alkyls include methyl, ethyl, propyl and butyl. Typically, $X^3$ is ethyl or propyl and $X^{48}$ is N,N-dialkylaminoalkyl, e.g., N,N-dimethylaminoethyl.

In one embodiment, the hydrophobic block comprises repeat units corresponding to Formula 1-CON

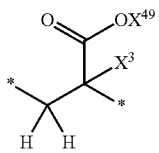

Formula 1-CON wherein * designates the point of attachment of the repeat unit of Formula 1-CON to other repeat units; $X^3$ is hydrogen or alkyl, and $X^{49}$ is substituted hydrocarbyl, heterohydrocarbyl, or heterocyclo. In one embodiment, $X^{49}$ comprises a conjugatable group. For example, $X^{49}$ may be an alkyl group substituted by N-hydroxysuccinimide (NHS)ester, HOBt (1-hydroxybenzotriazole) ester, p-nitrophenyl ester, tetrafluorophenyl ester, pentafluorophenyl ester, pyridyl disulfide group, maleimide, aldehyde, ketone, anhydride, thiol, amine, hydroxyl, alkyl halide, or other conjugatable group. In an alternative embodiment, $X^{49}$ may be a conjugatable group selected from succinimidyl, benzotriazyl, p-nitrophenyl, tetrafluorophenyl, or pentafluorophenyl.

In one embodiment, the hydrophobic block is a random copolymer comprising (i) repeat units corresponding to Formula 1A and Formula 1E, (ii) repeat units corresponding to Formula 1A and 1C, (iii) repeat units corresponding to Formula 1A, 1C and 1E, (iv) repeat units corresponding to Formula 1-CON and Formula 1A, (v) repeat units corresponding to Formula 1-CON, Formula 1A and Formula 1C, (vi) repeat units corresponding to Formula 1-CON, Formula 1A and Formula 1E, and (vii) repeat units corresponding to Formula 1-CON, Formula 1A and 1C, and (viii) repeat units corresponding to Formula 1-CON, Formula 1A, 1C and 1E. When the hydrophobic block comprises repeat units corresponding to Formula 1-CON, they will typically not constitute more than about 20% of the repeat units in the hydrophobic block. More typically, repeat units corresponding to Formula 1-CON, will not constitute more than about 15% of the repeat units in the hydrophobic block. In some embodiments, repeat units corresponding to Formula 1-CON, will constitute about 5% to about 10% of the repeat units in the hydrophobic block. In general, when the hydrophobic block is a random copolymer comprising repeat units corresponding to Formula 1A and Formula 1E (with or without repeat units corresponding to Formula 1C), the ratio of the number of repeat units corresponding to Formula 1A to the number of repeat units corresponding to Formula 1E in the third block is between about 20:1 and 1:4, respectively. For example, it is generally preferred that the ratio of the number of repeat units corresponding to Formula 1A to the number of repeat units corresponding to Formula 1E in the third block be between about 3:1 and 1:3, respectively. Additionally, it is generally preferred that the number of repeat units corresponding to Formula 1A exceed the number of repeat units corresponding to Formula 1C.

In one embodiment, the hydrophobic block comprises repeat units corresponding to Formula 1A, 1E, 1C and 1-CON wherein each $X^3$ is independently hydrogen or alkyl, $X^{47}$ is alkyl, $X^{48}$ is amino-substituted alkyl, and $X^{49}$ comprises a conjugatable group. For example, $X^{49}$ may be an alkyl group substituted by N-hydroxysuccinimide (NHS)ester, HOBt (1-hydroxybenzotriazole) ester, p-nitrophenyl ester, tetrafluorophenyl ester, pentafluorophenyl ester, pyridyl disulfide group, maleimide, aldehyde, ketone, anhydride, thiol, amine, hydroxyl, alkyl halide, or other conjugatable group. Exemplary alkyls include methyl, ethyl, propyl and butyl. Typically, $X^3$ is methyl, ethyl or propyl, $X^{48}$ is N,N-dialkylaminoalkyl, and $X^{49}$ is alkyl substituted by pyridyl disulfide. Thus, for example, in one embodiment, the hydrophobic block comprises repeat units corresponding to Formulae 1A, 1C, 1E, 1-CON and the relative mole ratio of these repeat units is about 25:25:40:10, respectively. In another exemplary embodiment, the hydrophobic block comprises repeat units corresponding to Formulae 1A, 1C, 1E, 1-CON and the relative mole ratio of these repeat units is about 25:25:45:5, respectively. In another exemplary embodiment, the hydrophobic block comprises repeat units corresponding to Formulae 1A, 1C, 1E, 1-CON and the relative mole ratio of these repeat units is about 20:20:50:10, respectively. In one preferred embodiment, the hydrophobic block comprises, as repeat units, the residues of 2-propylacrylic acid, N,N-dimethylaminoethyl methacrylate, butyl methacrylate, and pyridyldisulfide methacrylate ester. In certain preferred embodiments, the hydrophobic block comprises, as repeat units, the residues of 2-propylacrylic acid (a Formula 1A constituent), N,N-dimethylaminoethyl methacrylate (a Formula 1C constituent), butyl methacrylate (a Formula 1E constituent), and pyridyldisulfide methacrylate ester (a Formula 1-CON constituent) in any of the ratios disclosed herein for Formulae 1A, 1C, 1E, and 1-CON, respectively.

In general, the hydrophobic block comprises a plurality of repeat units, i.e., at least two. In certain embodiments, a hydrophobic block of a polymer described herein has a number average molecular weight of about 1,000 Dalton to about 200,000 Dalton, about 1,000 Dalton to about 100,000 Dalton, about 1,000 Dalton to about 100,000 Dalton, about 5,000 Dalton to about 50,000 Dalton, about 10,000 Dalton to about 50,000 Dalton, about 15,000 Dalton to about 35,000 Dalton, or about 20,000 Dalton to about 30,000 Dalton.

Targeting Block

As previously noted, the polymer optionally comprises at least one targeting block containing a residue of the targeting monomer of the present invention. In general, it is preferred that the targeting block be a hydrophilic block. In addition, it is generally preferred that the targeting block be a copolymer block, containing residues of the targeting monomer of the present invention, and the residues of one or more monomers described elsewhere herein. For example, it is generally preferred that a minority of the monomeric residues constituting the targeting block be residues of the targeting monomer and that the majority of the monomeric residues "dilute" the concentration of the targeting monomer, provide a means for attaching a therapeutic agent, increase the hydrophilicity of the block, and/or provide other functionality. For some targeting moieties such as folate, folate analogs, and biotin that are relatively hydrophobic, it is generally preferred that the targeting block be a random copolymer block and that no more than about 20% of the repeat units of the targeting block be the residue of a targeting monomer containing such moieties. In one specific embodiment, it is preferred that the targeting block be a random copolymer block and that no more than about 10% of the repeat units of the targeting block be the residue of a targeting monomer having folate, a folate analog, or biotin as a targeting moiety. For other targeting moieties, such as peptides, bisphosphonates, bisphosphonate analogs, and PSMA inhibitors, substantially greater percentages may be desired.

Additionally, in certain embodiments, the polymer will be a diblock polymer comprising a targeting block and a hydrophobic block. In other embodiments, the polymer will be a multiblock polymer comprising (i) a targeting block, (ii) a carrier block (hydrophilic or hydrophobic) that is attached to a therapeutic agent or possesses a functional group enabling the attachment of a therapeutic agent such as a polynucleotide, and (iii) a hydrophobic block. In certain embodiments, the polymer may comprise, in addition to the targeting block, one or more compositionally distinct hydrophilic blocks; and/or one or more compositionally distinct hydrophobic blocks.

In general, it is preferred that the targeting block comprise residues of a targeting monomer of the present invention and that the block have a number average molecular weight of about 1,000 daltons to about 25,000 daltons. In some embodiments, the targeting block will have a number average molecular weight of about 5,000 daltons to about 20,000 daltons. In some embodiments, the targeting block will have a number average molecular weight of about 5,000 daltons to about 15,000 daltons. In some embodiments, the targeting block will have a number average molecular weight of about 10,000 daltons.

Hydrophilic Block

As previously noted, the polymer comprises a targeting block containing residues of the targeting monomer of the present invention. In general, it is preferred that the targeting block be a hydrophilic block. In such embodiments, the targeting block will contain residues of the targeting monomer and, preferably, other monomers contributing to the overall hydrophilic character of the block. In addition, the polymer may contain one or more additional hydrophilic blocks. It should be understood, therefore, that the features and compositional components described herein in connection with hydrophilic blocks, apply to targeting blocks as well as non-targeting hydrophilic blocks.

In certain embodiments, therefore, the polymer will be a diblock polymer comprising a targeting/hydrophilic block and a hydrophobic block. In other embodiments, the polymer will be a multiblock polymer comprising two or more compositionally distinct hydrophilic blocks; in such instances, one of the hydrophilic blocks may be a targeting block (comprising the residue of a monomer corresponding to Formula 1r hydrophilic block may be shielding or a carrier block (for carrying a therapeutic agent). It should be understood, therefore, that when the polymer comprises two or more hydrophilic blocks, each of the hydrophilic blocks may be independently selected from hydrophilic blocks described herein, and that (at least) one of the blocks comprises residues of the monomers of the present invention in addition to any of the other monomers described herein.

In some embodiments, the polymer comprises at least one hydrophilic block comprising a plurality of charged species (i.e., is polycationic, polyanionic, or both), and/or is associated with a molecule that comprises a plurality of charged species (e.g., a polynucleotide or polypeptide). In specific embodiments, the polymer comprises at least one hydrophilic block comprising a population of species that are charged at about neutral pH (i.e., is polycationic, polyanionic, or both at about neutral pH). In certain embodiments, at least one of the hydrophilic blocks is a shielding block. In specific embodiments, the shielding block is non-charged, e.g., at about neutral pH.

Hydrophilic block(s) may be used to contribute a range of properties or functions to the copolymer of the present invention. For example, the number and composition of the constituent units of the hydrophilic block(s) may be selected to impart the desired degree of water solubility/dispersability to the copolymer. Alternatively, or additionally, in those embodiments in which the polymers of the present invention are incorporated into micelles, the number and composition of the constituent units of the hydrophilic block(s) may be selected to provide micelles having a desired size, critical micelle concentration or other property. Independent of micelle formation, the number and composition of the constituent units of the hydrophilic block(s) may be selected to target the polymer to a cellular or other biological target. Alternatively, or additionally, the number and composition of the constituent units of the hydrophilic block(s) may be selected to shield a therapeutic agent that is associated with the copolymer.

Depending upon the desired properties and functionality, the hydrophilic block(s) may be a homopolymer block or a copolymer block. In those embodiments in which it is a copolymer block, it is preferably a random copolymer block. For example, the hydrophilic block(s) may be copolymer block(s) comprising two or more compositionally distinct monomeric residues. By way of further example, the hydrophilic block(s) may be copolymer block(s) comprising charged repeat units (i.e., cationic repeat units, anionic repeat units, zwitterionic repeat units or a combination thereof), non-charged repeat units, or a combination thereof. In one specific embodiment, the hydrophilic block(s) comprise(s) charged repeat units. In another specific embodiment, the hydrophilic block(s) comprise(s) cationic repeat units. In yet another embodiment, the hydrophilic block comprise(s) cationic repeat units and non-charged repeat units. In yet another embodiment, the hydrophilic block(s) comprise(s) zwitterionic repeat units and non-charged repeat units. In yet another embodiment, the hydrophilic block(s) comprise(s) exclusively non-charged repeat units and the block is non-charged at neutral pH. Furthermore, in those embodiments in which the hydrophilic block(s) comprise(s) cationic repeat units, the hydrophilic block(s) may comprise a combination of two or more compositionally distinct cationic repeat units; in those embodiments in which the hydrophilic block(s) comprise(s) anionic repeat units, the hydrophilic block may comprise a combination of two or more compositionally distinct anionic repeat units; in those embodiments in which the hydrophilic block(s) comprise(s) zwitterionic repeat units, the hydrophilic block may comprise a combination of two or more compositionally distinct zwitterionic repeat units; and in those embodiments in which the hydrophilic block(s) comprise(s) non-charged repeat units, the hydrophilic block(s) may comprise a combination of two or more compositionally distinct non-charged repeat units.

In general, the hydrophilic block(s) may contain anionic repeat units, cationic repeat units, zwitterionic repeat units, a combination of two or more charged repeat units (e.g., anionic and cationic repeat units, anionic and zwitterionic repeat units, cationic and zwitterionic repeat units, or anionic, cationic and zwitterionic repeat units), substantially non-charged repeat units, or a combination thereof, provided that its overall character is hydrophilic. Stated differently, the hydrophilic block(s) may contain any of a wide range of repeat units, hydrophilic or even hydrophobic, provided that the sum of the contributions of the repeat units comprised by the first hydrophilic block provide a block having an overall hydrophilic character. When the repeat units contain ionizable groups, the contribution of an individual repeat unit to the overall hydrophilicity of the block of which it is a constituent may vary as a function of its pKa relative to the pH of the environment in which it is found. For example, propyl acrylic acid repeat units, —$CH_2C(CH_2CH_2CH_3)(COOH)$—, are predominantly ionized at pH 7 but not at pH 5 and thus, the hydrophobic contribution of propyl acrylic acid repeat units to a block is significantly greater at pH 5 than at pH 7. In general, therefore, when the first hydrophilic block comprises ionizable cationic repeat units or ionizable anionic repeat units, it is preferred that the sum of the contributions of the repeat units constituting the first hydrophilic block be such that the overall character of the block is hydrophilic at physiological pH. For example, in one embodiment, it is preferred that the hydrophilic block(s) be hydrophilic over the range of pH from pH 5.0 to pH 7.5.

In some embodiments, the hydrophilic block is a substantially non-charged block. In specific embodiments, the hydrophilic block is substantially non-charged and shields a charged second block and/or a charged therapeutic agent associated with the hydrophobic block. For example, the hydrophilic block may be a polysaccharide block.

In some other embodiments, the hydrophilic block is a polyzwitterionic (i.e., comprising a plurality of both cationic and anionic species or monomeric residues at about neutral pH), polyanionic block (i.e., comprising a plurality of anionic monomeric residues at about neutral pH), or polycationic block (i.e., comprising a plurality of cationic monomeric residues at about neutral pH). In either of these embodiments, the hydrophilic block may comprise at least one conjugatable or functionizable monomeric residue that may be used, for example, to link a targeting group, a water-solubilizing group, or other functional group to the polymer block, post-polymerization.

In one preferred embodiment, the hydrophilic block is a hydrophilic polymer block suitable for (capable of/effective for) steric shielding of the polynucleotide. In this embodiment, the hydrophilic block comprises a plurality of monomeric residues having a shielding species, and the shielding species is effective for steric shielding of a polynucleotide associated with the polymer or a micelle comprising the polymer. For example, the shielding species may be effective for enhancing the stability of the polynucleotide against enzymatic digestion in plasma. Additionally, or alternatively, the shielding species may be effective for reducing toxicity of a polymer or micelle described (e.g., by shielding a charged second hydrophilic block and reducing the effective surface charge of a polymer or micelle). Additionally, or alternatively, the shielding species is effective for maintaining desirable surface properties of a micelle comprising the polymer. Additionally, or alternatively, the shielding species may be effective for increasing the circulation time in or decreasing its clearance rate by the kidneys.

Depending upon the desired properties, the shielding species of a polymer or micelle may be selected from a range of moieties. For example, the shielding species may be an alcohol, a phenol, a thiol, a polyoxylated alkyl (e.g., polyethylene glycol, polypropylene glycol, or the like), an ether, a thioether, or the like. In some embodiments, the hydrophilic block comprises a plurality of monomeric residues having a pendant group comprising a shielding oligomer (e.g., polyethylene glycol, polypropylene glycol, or the like). In specific embodiments, the shielding species of a polymer or micelle described herein is a polyoxylated alkyl with the structure of Formula II:

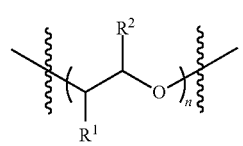

(II)

wherein each $R^1$ and $R^2$ are each independently selected from the group consisting of hydrogen, halogen, and optionally substituted $C_1$-$C_3$ alkyl, and n is an integer. In a preferred embodiment, the number of repeat units, n, will provide a shielding species having a molecular weight of about 40 to about 2000 daltons. In specific embodiments, n will be about 2-20; for example, n may be about 3-10 and, depending upon the polymer, about 4-5, about 8-9, or the like. In some embodiments, the shielding species corresponds to Formula II and has a molecular weight of about 40 to about 2000 dalton, or about 100 to about 2000 dalton.

In some embodiments, the hydrophilic block is a copolymer comprising monomeric residues corresponding to Formula Ia, and other monomeric residues. In preferred embodiments, the other monomeric residues are non-charged. In some embodiments, the other monomeric residues are non-hydrophobic. In certain embodiments, the other monomeric residues do not significantly affect the overall hydrophilicity of the hydrophilic block.

In one preferred embodiment, the hydrophilic block comprises repeat units corresponding to Formula 1

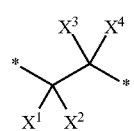

Formula 1 wherein * designates the point of attachment of the repeat unit of Formula 1 to other repeat units; each $X^1$ and $X^2$ is independently selected from the group consisting of hydrogen, hydrocarbyl, substituted hydrocarbyl, heterocyclo, and substituted carbonyl, provided, however, $X^1$ and $X^2$ are not, in the same repeat unit, selected from the group consisting of aryl, heteroaryl, heterosubstituted carbonyl, and combinations thereof; each $X^3$ is independently hydrogen, alkyl or substituted alkyl, and each $X^4$ is independently heterosubstituted carbonyl, aryl, or heteroaryl. For example, in one such embodiment, the hydrophilic block comprises repeat units corresponding to Formula 1 and $X^1$ and $X^2$ are each hydrogen. In another such example, the hydrophilic block comprises repeat units corresponding to Formula 1, $X^1$ and $X^2$ are each hydrogen and $X^3$ is hydrogen or alkyl. In a further example, the hydrophilic block comprises repeat units corresponding to Formula 1, $X^1$ and $X^2$ are each hydrogen, $X^3$ is hydrogen or alkyl, and each $X^4$ is independently heterosubstituted carbonyl. In a further example, the hydrophilic block comprises repeat units corresponding to Formula 1, $X^4$ is —$C(O)OX^{40}$, —$C(O)SX^{40}$, or —$C(O)NX^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In a further example, the hydrophilic block comprises repeat units corresponding to Formula 1, $X^4$ is —C(O)O$X^{40}$ or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In a further example, the hydrophilic block comprises repeat units corresponding to Formula 1, $X^1$ and $X^2$ are each hydrogen, $X^3$ is hydrogen or alkyl, $X^4$ is —C(O)O$X^{40}$, and $X^{40}$ is hydrogen, hydrocarbyl, substituted hydrocarbyl, heterohydrocarbyl, substituted heterohydrocarbyl, or heterocyclo. In a further example, the hydrophilic block comprises repeat units corresponding to Formula 1, $X^1$ and $X^2$ are each hydrogen, $X^3$ is hydrogen or alkyl, $X^4$ is —C(O)O$X^{40}$, $X^{40}$ is —(CH$_2$CH$_2$O)$_t$$X^{400}$, t is a positive integer, and $X^{400}$ is alkyl, substituted alkyl, or heterocyclo. In a further example, the hydrophilic block comprises repeat units corresponding to Formula 1, $X^1$ and $X^2$ are each hydrogen, $X^3$ is hydrogen or alkyl, $X^4$ is —C(O)O$X^{40}$, $X^{40}$ is —(CH$_2$CH$_2$O)$_t$$X^{400}$, t is a positive integer, and $X^{400}$ comprises a targeting moiety. In a further example, the hydrophilic block comprises repeat units corresponding to Formula 1 and the repeat units corresponding to Formula 1 constitute a majority of the total number of repeat units in the hydrophilic block. In a further example, the hydrophilic block comprises repeat units corresponding to Formula 1 and the repeat units corresponding to Formula 1 constitute at least 75% of the total number of repeat units in the hydrophilic block. In a further example, the hydrophilic block comprises repeat units corresponding to Formula 1 and the repeat units corresponding to Formula 1 constitute at least 90% of the total number of repeat units in the hydrophilic block.

In one alternative embodiment, the hydrophilic block is a random copolymer comprising at least two compositionally distinct repeat units, at least one of which corresponds to Formula 1. In another alternative embodiment, the hydrophilic block is a random copolymer comprising at least two compositionally distinct repeat units, each of which corresponds to Formula 1. For example, the hydrophilic block may be a random copolymer comprising (i) a first repeat unit corresponding to Formula 1 in which $X^4$ is —C(O)OH and (ii) a compositionally distinct second repeat unit corresponding to Formula 1. In a further example, the hydrophilic block is a random copolymer comprising at least two compositionally distinct repeat units, each of which corresponds to Formula 1, and the repeat units corresponding to Formula 1 constitute a majority of the total number of repeat units in the hydrophilic block. In a further example, the hydrophilic block is a random copolymer comprising at least two compositionally distinct repeat units, each of which corresponds to Formula 1, and the repeat units corresponding to Formula 1 constitute at least 90% of the total number of repeat units in the hydrophilic block.

In another preferred embodiment, the hydrophilic block comprises repeat units corresponding to Formula 1ETS Formula 1ETS

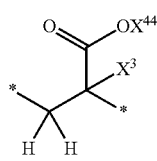

wherein * designates the point of attachment of the repeat unit of Formula 1ETS to other repeat units, $X^3$ is alkyl, and $X^{44}$ is a targeting or shielding moiety. For example, $X^{44}$ may be a polyol, a vitamin, a peptide, or other moiety that has a binding affinity for a cellular or biological target. For example, in one such embodiment the hydrophilic block comprises repeat units corresponding to Formula 1ETS and $X^{44}$ is a polyol. In a further example, the hydrophilic block comprises repeat units corresponding to Formula 1ETS and the repeat units corresponding to Formula 1ETS may constitute at least 2% of the total number of repeat units in the hydrophilic block. In a further example, the hydrophilic block comprises repeat units corresponding to Formula 1ETS and the repeat units corresponding to Formula 1ETS may constitute at least 5% of the total number of repeat units in the hydrophilic block. In a further example, the hydrophilic block is a random copolymer comprising at least two repeat units, one corresponding to Formula 1ETS and the other being a compositionally distinct repeat unit corresponding to Formula 1. In a further example, the hydrophilic block is a random copolymer comprising at least two repeat units, one corresponding to Formula 1ETS and another corresponding to Formula 1 wherein $X^4$ is —COOH.

In certain embodiments, the hydrophilic block comprises a plurality of monomeric residues obtained by the polymerization or copolymerization of a monomer of Formula IIIb:

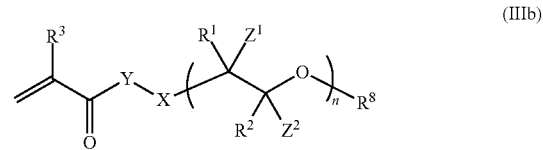

(IIIb)

wherein:

n is an integer ranging from 2 to 20;

X is —(CR$^1$R$^2$)$_m$— wherein m is 0-10, and wherein one or more (CR$^1$R$^2$) unit is optionally substituted with —NR$^1$R$^2$, —OR$^1$ or —SR$^1$, Y is —O—, —NR$^4$— or —(CR$^1$R$^2$)—, each R$^1$, R$^2$, R$^3$, Z$^1$ and Z$^2$ are independently selected from the group consisting of hydrogen, halogen, and optionally substituted C$_1$-C$_3$ alkyl, R$^4$ is selected from the group consisting of hydrogen, and optionally substituted C$_1$-C$_6$ alkyl, R$^8$ is hydrogen or (CR$^1$R$^2$)$_m$R$^9$, wherein m is 0-10, and wherein one or more (CR$^1$R$^2$) unit is optionally substituted with —NR$^1$R$^2$, —OR$^1$ or —SR$^1$, and R$^9$ is hydrogen, halogen, optionally substituted C$_1$-C$_3$ alkyl, polyol, vitamin, peptide, small molecule having a molecular weight of 200-1200 Daltons, or a conjugatable group.

In certain embodiments, the hydrophilic block comprises a plurality of monomeric residues obtained by the polymerization or copolymerization of a monomer of Formula IIIc:

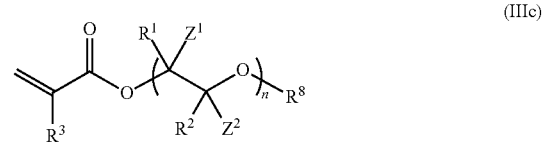

(IIIc)

wherein:

n is an integer ranging from 2 to 20;

X is —$(CR^1R^2)_m$— wherein m is 0-10, and wherein one or more $(CR^1R^2)$ unit is optionally substituted with —$NR^1R^2$, —$OR^1$ or —$SR^1$, Y is —O—, —$NR^4$— or —$(CR^1R^2)$—, each $R^1$, $R^2$, $R^3$, $Z^1$ and $Z^2$ are independently selected from the group consisting of hydrogen, halogen, and optionally substituted $C_1$-$C_3$ alkyl, $R^4$ is selected from the group consisting of hydrogen, and optionally substituted $C_1$-$C_6$ alkyl, $R^8$ is hydrogen or $(CR^1R^2)_mR^9$, wherein m is 0-10, and wherein one or more $(CR^1R^2)$ unit is optionally substituted with —$NR^1R^2$, —$OR^1$ or —$SR^1$, and $R^9$ is hydrogen, halogen, optionally substituted $C_1$-$C_3$ alkyl, polyol, vitamin, peptide, small molecule having a molecular weight of 200-1200 Daltons, or a conjugatable group.

For example, in one embodiment, the hydrophilic block comprises a plurality of monomeric residues corresponding to Formula IIIc, $R^1$, $R^2$, $Z^1$ and $Z^2$ are hydrogen, $R^3$ is hydrogen or $C_1$-$C_3$ alkyl, n is 2-20 and $R^9$ is a polyol, vitamin, peptide, or small molecule having a molecular weight of 200-1200 Daltons.

In certain embodiments, the hydrophilic block comprises a plurality of monomeric residues obtained by the polymerization or copolymerization of a monomer of Formula III:

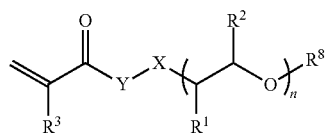

(III)

wherein:

X is $(CR^1R^2)_m$, wherein m is 0-10, and wherein one or more $(CR^1R^2)$ unit is optionally substituted with $NR^1R^2$, $OR^1$ or $SR^1$, Y is O, $NR^4$, or $CR^1R^2$, each $R^1$, $R^2$, $R^3$ and $R^9$ are independently selected from the group consisting of hydrogen, halogen, optionally substituted $C_1$-$C_3$ alkyl, or a targeting group, such as but not limited to galactose, N-acetyl galactosamine, folate, RGD peptide, $R^4$ is selected from the group consisting of hydrogen, and optionally substituted $C_1$-$C_6$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In specific embodiments, the hydrophilic block comprises a plurality of monomeric residues obtained by the polymerization or copolymerization of a monomer of Formula IIIa:

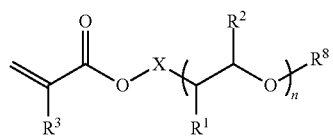

(IIIa)

wherein:

X is $(CR^1R^2)_m$, wherein m is 0-10, and wherein one or more $(CR^1R^2)$ unit is optionally substituted with $NR^1R^2$, $OR^1$ or $SR^1$, each $R^1$, $R^2$, $R^3$ and $R^9$ are independently selected from the group consisting of hydrogen, halogen, and optionally substituted $C_1$-$C_3$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In one embodiment, the hydrophilic block comprises a plurality of monomeric residues corresponding to Formula IIIa and $R^3$ is methyl (i.e., the monomer of Formula III is a PEGMA).

In certain embodiments, the hydrophilic block comprises a plurality of monomeric residues obtained by the polymerization or copolymerization of a monomer of Formula IV:

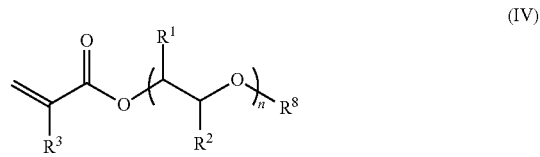

(IV)

wherein:

each $R^1$, $R^2$ and $R^3$ are independently selected from the group consisting of hydrogen, halogen, and optionally substituted $C_1$-$C_3$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In one embodiment, the hydrophilic block comprises a plurality of monomeric residues corresponding to Formula IV, $R^3$ is methyl and n is 2-20.

In general, the hydrophilic block comprises a plurality of repeat units, i.e., at least two. In some embodiments, a hydrophilic block of a polymer described herein has a number average molecular weight of about 1,000 Dalton to about 50,000 Dalton, about 2,000 Dalton to about 30,000 Dalton, about 5,000 Dalton to about 20,000 Dalton, or about 7,000 Dalton to about 15,000 Dalton. In specific embodiments, the hydrophilic block is of about 7,000 Dalton, 8,000 Dalton, 9,000 Dalton, 10,000 Dalton, 11,000 Dalton, 12,000 Dalton, 13,000 Dalton, 14,000 Dalton, or 15,000 Dalton.

Polymerization

Although the monomers of the present invention may be copolymerized with any of a range of comonomers, it is generally preferred that the other comonomers be ethylenically unsaturated monomers. In more specific embodiments, ethylenically unsaturated monomers include, by way of non-limiting example, acrylic monomers, a vinylic monomer, and the like having at least one carbon double or triple bond. Non-limiting examples of ethylenically unsaturated monomers include an alkyl (alkyl)acrylate, a methacrylate, an acrylate, an alkylacrylamide, a methacrylamide, an acrylamide, a styrene, an allylamine, an allylammonium, a diallylamine, a diallylammonium, an N-vinyl formamide, a vinyl ether, a vinyl sulfonate, an acrylic acid, a sulfobetaine, a carboxybetaine, a phosphobetaine, or maleic anhydride In some embodiments, the ethylenically unsaturated monomer is an acrylic monomer selected from an optionally substituted acrylic acid, an optionally substituted acrylamide, and an optionally substituted acrylate. In certain embodiments, the ethylenically unsaturated monomer is selected from optionally $C_1$-$C_8$ alkyl-substituted acrylic acid, an optionally $C_1$-$C_8$ alkyl-substituted acrylamide, and an optionally $C_1$-$C_8$ alkyl-substituted acrylate. Non-limiting examples of comonomers include: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylpyridine, vinylimidazole, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, functionalized versions of these comonomers are optionally used. A functionalized comonomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Bronsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the polymers are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) ("Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001)).

In certain embodiments, Reversible Addition-Fragmentation chain Transfer or RAFT is used in synthesizing ethylenic backbone polymers of this invention. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In most instances, this cycle of addition to the C=S bond followed by fragmentation of the ensuing radical continues until all monomer has been consumed or the reaction is quenched. Generally, the low concentration of active radicals at any particular time limits normal termination reactions.

In some embodiments, polymers of the present invention have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, the polymers (e.g., membrane destabilizing polymers) provided herein have a polydispersity index (PDI) of less than 2.0, or less than 1.8, or less than 1.6, or less than 1.5, or less than 1.4, or less than 1.3, or less than 1.2. In some embodiments, the polymer is a block copolymer (e.g., membrane destabilizing block copolymers) comprising a hydrophilic block and a hydrophobic block and having a polydispersity index (PDI) of less than 2.0, or less than 1.8, or less than 1.6, or less than 1.5, or less than 1.4, or less than 1.3, or less than 1.2.

Polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

In certain embodiments, poly(DMAEMA) and other polymeric entities used herein (e.g., copolymers or copolymer blocks of BMA, DMAEMA and PAA) are prepared in any suitable manner. In one embodiment, poly(DMAEMA/PEGMA) is prepared by co-polymerizing DMAEMA and PEGMA in the presence of the RAFT CTA, ECT, and a radical initiator. In some embodiments, a block, poly(DMAEMA/PEGMA) macroCTA is used to prepare a series of diblock, triblock or other multiblock copolymers where the hydrophobic block contains BMA, DMAEMA and PAA. In other specific embodiments, the orientation of the blocks on the diblock, triblock or other multiblock polymer is reversed, such that upon self-assembly, the ω end of the polymer is exposed on the hydrophilic segment of the micelle. In various embodiments, this is achieved in any suitable manner, including a number of ways synthetically. For example, in some embodiments, the synthesis of the block copolymers described herein begins with the preparation of the PAA/BMA/DMAEMA core-forming hydrophobic block, and the shell-forming hydrophilic, charged block is added in the second synthetic step by subjecting the resulting PAA/BMA/DMAEMA macroCTA to a second RAFT polymerization step. Alternate approaches include reducing the PAA/BMA/DMAEMA macroCTA to form a thiol end and then covalently attaching a pre-formed hydrophilic, charged polymer to the formed thiol. This synthetic approach provides a method for introduction of a reactive group on the omega-end of the polymeric chain exposed to the surface of micelle thus providing alternate approaches to chemical conjugation to the micelle.

In some embodiments, block copolymers are synthesized by chemical conjugation of several polymer blocks that are prepared by separate polymerization processes.

Block Ratios

In certain embodiments, the polymer of the present invention is a block copolymer comprising a hydrophilic and a hydrophobic block. In this embodiment, the block copolymer has a ratio of a number-average molecular weight (with the number average molecular weight of the first block, i.e., hydrophilic block, represented by $M_n^{1st}$, the number average molecular weight of the hydrophobic block represented by $M_n^{2nd}$, of $M_n^{1st}:M_n^{2nd}$) of about 2:1 to about 1:9. In some embodiments, $(M_n^{1st}):(M_n^{2nd})$ is about 1:1 to about 1:3.

Micelle

In certain embodiments, micelles are formed from a plurality of polymers comprising a hydrophilic block and a hydrophobic block as described elsewhere herein. In certain embodiments, a micelle described herein comprises a plurality of block copolymers, the micelle comprising a core and a shell. In specific embodiments, the core of the micelle comprises the hydrophobic blocks of the plurality of block copolymers and the shell comprises the hydrophilic blocks of the block copolymers. Moreover, in more specific embodiments, the shell comprises an inner layer and an outer layer (relative to one another; further layers are also possible), the hydrophilic block forming the outer layer and the second hydrophilic block forming the inner layer of the micelle shell.

In specific embodiments, a plurality of any one or more polymer described herein is assembled into a micelle. In specific embodiments, such a micelle is stable in at about neutral pH (e.g., is stable in an aqueous medium at about pH 7.4).

In some embodiments, a micelle described herein comprises any number of polymers described herein, e.g., about 10 to about 100 of the copolymers described herein per micelle, or about 20 to about 60 of the copolymers described herein per micelle.

In one embodiment, a micelle described herein (without an associated therapeutic agent such as a polynucleotide) has a Zeta potential that is between ±6 mV (millivolt). In one preferred embodiment, a micelle described herein (without an associated therapeutic agent such as a polynucleotide) has a Zeta potential that is between ±5 mV. In one preferred embodiment, a micelle described herein (without an associated therapeutic agent such as a polynucleotide) has a Zeta potential that is between ±2 mV.

In general, the micelles described herein may have a critical micelle concentration, CMC, ranging from about 0.2 µg/ml to about 100 µg/ml. For example, in one preferred embodiment, the micelles have a CMC of about 0.2 µg/ml to about 20 µg/ml. In specific embodiments, the micelle has a critical micelle concentration, CMC, ranging from about 0.5 µg/ml to about 10 µg/ml. In certain embodiments, a micelle described herein comprises a plurality of block copolymers described herein, the plurality of block copolymers described herein having a polydispersity index (PDI) of about 1.1 to about 1.7, or about 1.1 to about 1.4. In some embodiments, a micelle comprises a plurality of copolymers described herein wherein the hydrophobic block(s) and any hydrophilic block(s), when present, of the block copolymer have a polydispersity index of not more than 1.5.

In certain embodiments, a micelle described herein comprise a plurality of copolymers, as described herein, wherein at least one or more of the plurality of copolymers is covalently crosslinked to the second polymer, whereby the polymeric micelle is a crosslinked polymeric micelle. In specific embodiments, the second polymer is also a copolymer as described herein. In some embodiments, the block copolymer is covalently crosslinked to the hydrophobic block of the second polymer. In specific embodiments, the hydrophobic blocks of two copolymers described herein are crosslinked to each other. In certain embodiments, the block copolymer comprises a plurality of monomeric residues derived from controlled radical polymerization of an ethylenic monomer, at least one such monomer being a bis-functional crosslinking monomer.

In some embodiments, a micelle provided herein is characterized by one or more of the following: (1) the micelle is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) the micelle is stable to dilution (e.g., down to a polymer concentration of 100 ug/ml, 50 ug/ml, 10 ug/ml, 5 ug/ml or 1 ug/ml, which constitutes the critical stability concentration or the critical micelle concentration (CMC)); (3) the micelle is stable to high ionic strength of the surrounding media (e.g. 0.5M NaCl); and/or (4) the micelle has an increasing instability as the concentration of organic solvent increases, such organic solvents including, but not limited to dimethylformamide (DMF), dimethylsulfoxide (DMSO), and dioxane. In some embodiments, a micelle provided herein is characterized by having at least two of the aforementioned properties. In some embodiments, a micelle provided herein is characterized by having at least three of the aforementioned properties. In some embodiments, a micelle provided herein is characterized by having all of the aforementioned properties.

In some embodiments, a micelle provided herein self-assembles at any suitable concentration. In certain embodiments, a micelle provided herein self-assembles (e.g., has a critical micelle concentration (CMC), or the minimum concentration at which a micelle forms) of about 2 µg/mL, about 5 µg/mL, about 8 µg/mL, about 10 µg/mL, about 20 µg/mL, about 25 µg/mL, about 30 µg/mL, about 40 µg/mL, about 50 µg/mL, about 60 µg/mL, about 70 µg/mL, about 80 µg/mL, about 90 µg/mL, about 100 µg/mL, or greater. In certain embodiments, a micelle provided herein self assembles at least one concentration between about 1 µg/mL and about 100 µg/m L.

In some embodiments, the micelles provided herein are prepared by spontaneous self-assembly of the polymers described herein. In certain embodiments, the polymers described herein assemble into the micelles provided herein upon dilution of a solution of the polymer in water-miscible organic solvent into aqueous media. In some embodiments, the micelles provided herein are formed spontaneously upon dissolution of the polymer directly in aqueous media. In some embodiments, the micelles do not require the presence of a polynucleotide for micelle formation.

In some embodiments, the micelles are stable to dilution in an aqueous solution. In specific embodiments, the micelles are stable to dilution at physiologic pH (including the pH of circulating blood in a human) with a critical stability concentration (e.g., a critical micelle concentration (CMC)) of approximately 50 to approximately 100 µg/mL, or approximately 10 to approximately 50 µg/mL, or less than 10 µg/mL. For example, in a preferred embodiment, the average hydrodynamic particle size for the micelle, as determined by dynamic light scattering techniques, does not change more than approximately 30% within the 5 minute period following dilution from a greater to a lesser concentration in an aqueous solution at a pH of 7.4, preferably at 37° C., the lesser concentration being greater than the midpoint polymer concentration of the transitional change following the concentration at which the micelle forms, as determined by uptake of a hydrophobic probe molecule (for example, the pyrene fluorescence assay).

In some embodiments, a micelle provided herein is stable in an aqueous medium. In certain embodiments, a micelle provided herein is stable in an aqueous medium at a selected pH, e.g., about physiological pH (e.g., the pH of circulating human plasma). In specific embodiments, a micelle provided herein is stable at about a neutral pH (e.g., at a pH of about 7.4) in an aqueous medium. In specific embodiments, the aqueous medium is animal (e.g., human) serum or animal (e.g., human) plasma. In certain embodiments, a micelle provided herein is stable in human serum and/or human plasma. In specific embodiments, the micelle is stable in circulating human plasma. It is to be understood that stability of the micelle is not limited to designated pH, but that it is stable at pH values that include, at a minimum, the designated pH. In specific embodiments, a micelle described herein is substantially less stable at an acidic pH than at a pH that is about neutral. In more specific embodiments, a micelle described herein is substantially less stable at a pH of about 5.8 than at a pH of about 7.4.

In specific embodiments, the micelle is stable at a concentration of about 10 µg/mL, or greater (e.g., at about a neutral pH). In some embodiments, the micelle is stable at a concentration of about 100 µg/mL, or greater (e.g., at about a neutral pH).

In one embodiment, the micelle is a heterogeneous polymeric micelle comprising a polymer of the present invention and at least one additional compositionally distinct polymer. Other compositionally distinct polymers include, for example, other block copolymers comprising a hydrophilic block and a hydrophobic block. Advantageously, the hydrophobic block of the other block copolymer(s) can associate with the hydrophobic block of the polymer of the present invention through hydrophobic interactions to form a hydrophobic core. By way of example, the heterogeneous micelle comprises (i) polymers having a therapeutic agent covalently coupled to a hydrophobic block thereof (the polymer optionally additionally comprising a hydrophilic block) and (ii) a multiblock copolymer comprising hydrophilic block(s) and hydrophobic block(s) but having no therapeutic agent covalently coupled thereto. Preferably, the heterogeneous micelle is stable in aqueous medium at a physiologically relevant pH (e.g., pH 7.4). In some embodiments, the heterogeneous polymeric micelle comprises one or more additional compositionally distinct polymers, such as a third polymer that is compositionally distinct from each of the first polymer and the second polymer. Generally, each block of a block copolymer (e.g., of the first polymer and/or the second polymer) can be a homopolymer or a random copolymer, in each case linear or non linear (e.g., branched), and in each case crosslinked or uncrosslinked, and can generally comprise one or more monomeric residues derived from polymerization of a polymerizable monomer (e.g., using controlled living radical polymerization approaches).

Membrane Destabilization

In some embodiments, a polymer or micelle described herein (including portions, such as polymer subunits, thereof) is membrane-destabilizing at a pH of about 6.5 or lower, preferably at a pH ranging from about 5.0 to about 6.5, or at a pH of about 6.2 or lower, preferably at a pH ranging from about 5.0 to about 6.2, or at a pH of about 6.0 or lower, preferably at a pH ranging from about 5.0 to about 6.0. For example, in one embodiment, the polymer or micelle is membrane-destabilizing at a pH of or less than about 6.2, of or less than about 6.5, of or less than about 6.8, of or less than about 7.0. In certain embodiments, membrane destabilization is of any cellular membrane such as, by way of non-limiting example, an extracellular membrane, an intracellular membrane, a vesicle, an organelle, an endosome, a liposome, or a red blood cell. In some embodiments, membrane destabilizing polymers (e.g., copolymers) or membrane destabilizing block copolymers provided herein are membrane destabilizing (e.g., in an aqueous medium) at an endosomal pH.

In some embodiments, a polymer or micelle described herein (including portions, such as polymer subunits, thereof) is hemolytic at pH of or less than about 6.2, of or less than about 6.5, of or less than about 6.8, of or less than about 7.0. In further or alternative embodiments, the polymer or micelle (including portions, such as polymer subunits, thereof) is substantially non-hemolytic at pH greater than about 7.0. In specific embodiments, a polymer or micelle (including portions, such as polymer subunits, thereof) described herein is hemolytic at given concentration and a pH of about 6.2, and substantially non-hemolytic at the same concentration and at a pH greater than about 7.0. In more specific embodiments, the concentration is between 2 and 18 ug/mL, where there is 50-100% hemolysis at pH 5.8 and little or no significant hemolysis at pH 7.4. In certain embodiments, the hemolytic nature of a polymer or micelle (including portions, such as polymer subunits, thereof) described herein is determined in any suitable manner, e.g., by use of any standard hemolysis assay, such as an in vitro hemolysis assay.

In certain embodiments, a polymer or micelle described herein (including portions, such as polymer subunits, thereof) is endosome disruptive. In some embodiments, a polymer or micelle described herein (including portions, such as polymer subunits, thereof) is endosome disruptive at pH of or less than about 6.2, of or less than about 6.5, of or less than about 6.8, of or less than about 7.0. In certain embodiments, a polymer In certain embodiments, the endosome disruptive nature of a polymer or micelle (including portions, such as polymer subunits, thereof) described herein is determined in any suitable manner, e.g., by use of any standard hemolysis assay, such as an in vitro endosomolysis assay, or an in vivo non-human mammal endosomolysis assay.

Therapeutic Agents

Provided in certain embodiments is a polymer or micelle, as described herein in combination with a therapeutic agent. In specific embodiments, the therapeutic agent is a polynucleotide (e.g., oligonucleotide) or a peptide. The therapeutic agent may be used prophylactically, as a vaccine or to treat a medical condition.

In various embodiments, research reagents, diagnostic agents, and/or therapeutic agents are attached to the block copolymer or a micelle containing the block copolymers in any suitable manner. In specific embodiments, attachment is achieved through covalent bonds, non-covalent interactions, static interactions, hydrophobic interactions, or the like, or combinations thereof. In some embodiments, the research reagents, diagnostic agents, and/or therapeutic agents are attached to an intermediate or second block of block copolymers, or micelles thereof. In certain embodiments, the research reagents, diagnostic agents, or therapeutic agents form the intermediate or second block of a block copolymer, or micelle thereof. In some embodiments, the research reagents, diagnostic agents, or therapeutic agents are in the shell of the micelle.

In some embodiments, provided herein is a micelle comprising a first therapeutic agent in the shell of the micelle and a second therapeutic agent in the core of the micelle. In specific embodiments, the first therapeutic agent is a polynucleotide. And the second therapeutic agent is a hydrophobic drug. In certain embodiments, provided herein is a micelle comprising a hydrophobic drug (e.g., small molecule hydrophobic drug) in the core of the micelle.

In certain embodiments, provided herein is a micelle comprising at least 1-5, 5-250, 5-1000, 250-1000, at least 2, at least 5, at least 10, at least 20, or at least 50 polymers with attached therapeutic agents. In some embodiments, provided herein is a composition comprising a plurality of micelles described herein, wherein the micelles therein comprise, on average, at least 1-5, 5-250, 5-1000, 250-1000, at least 2, at least 5, at least 10, at least 20, or at least 50 polymers with attached therapeutic agents.

In some embodiments, therapeutic agents, diagnostic agents, etc., are selected from, by way of non-limiting example, at least one nucleotide (e.g., a polynucleotide), at least one carbohydrate or at least one amino acid (e.g., a peptide). In specific embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other specific embodiments, the therapeutic agent is an aiRNA (Asymmetric RNA duplexes mediate RNA interference in mammalian cells. Xiangao Sun, Harry A Rogoff, Chiang J Li *Nature Biotechnology* 26, 1379-1382 (2008)). In certain embodiments, the therapeutic agent is a protein, peptide, enzyme, antibody, or antibody fragment. In some embodiments, the therapeutic agent is a carbohydrate, or a small molecule with a molecular weight of greater than about 500 Daltons.

In some embodiments, a polynucleotide associated with a polymer or micelle described herein is an oligonucleotide gene expression modulator. In certain embodiments, the polynucleotide is an oligonucleotide aptamer. In some embodiments, the polynucleotide is an oligonucleotide knockdown agent. In certain embodiments, the polynucleotide is an interfering RNA. In some embodiments, the polynucleotide is an oligonucleotide selected from an siRNA, an antisense oligonucleotide, a dicer substrate, an miRNA, an aiRNA or an shRNA. In specific embodiments, the polynucleotide is a siRNA.

In some embodiments, a therapeutic agent (e.g., oligonucleotide) is chemically conjugated to the polymer or to the micelle and/or to one or more polymer of the micelle by any suitable chemical conjugation technique. In some embodiments, micelles containing an RNAi agent are formed by conjugation of the RNAi agent with an already formed micelle comprising a plurality of polymers (e.g., block copolymers). In other embodiments, micelles containing an RNAi agent are formed by conjugation of the RNAi agent with a polymer (e.g., a membrane destabilizing block copolymer) and subsequently forming the micelle in any suitable manner, e.g., by self assembly of the resulting conjugates into a micelle comprising the RNAi agent. In various embodiments, such a micelle optionally further comprises unconjugated polymers (e.g., block copolymers) that are similar, identical, or different than those conjugated to the RNAi agent. The covalent bond between a polymer and a therapeutic agent of a micelle described herein is, optionally, non-cleavable, or cleavable. In certain embodiments, a precursor of one or more RNAi agent (e.g. a dicer substrate) is attached to the micelle or to the polymeric units of the micelle by a non-cleavable bond. In some embodiments, one or more RNAi agent is attached through a cleavable bond. In certain embodiments, the cleavable bonds utilized in the micelles described herein include, by way of non-limiting example, disulfide bonds (e.g., disulfide bonds that dissociate in the reducing environment of the cytoplasm). In some embodiments, covalent association between a micelle (including the components thereof) and a therapeutic agent (e.g., an oligonucleotide or siRNA) is achieved through any suitable chemical conjugation method, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, *Bioconjugation*, Aslam and Dent, Eds, Macmillan, 1998 and chapters therein).

In specific embodiments, the agent delivered by the means of the polymer or the micelle provided herein is a diagnostic agent. In some embodiments, the diagnostic agent is a diagnostic imaging agent, e.g., an agent useful in imaging the mammalian vascular system which includes but is not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, or their complexes, chelates, adducts and conjugates. In other embodiments, the diagnostic agent is a marker gene that encode proteins that are readily detectable when expressed in a cell (including, but not limited to, β-galactosidase, green fluorescent protein, luciferase, and the like) and labeled nucleic acid probes (e.g., radiolabeled or fluorescently labeled probes). In some embodiments, covalent conjugation of diagnostics agents to the polymers or the micelles provided herein is achieved according to a variety of conjugation processes. In some embodiments, a radiolabeled monomer (e.g., a $^{14}$C-labeled monomer) is incorporated into the polymeric backbone of the micelle. In some embodiments, a polymer or a micelle associated with a diagnostic agent comprises a targeting moiety.

Method for Preparing Micelle Composition

In a preferred embodiment, a micelle comprising a polymer of the present invention may be prepared by in a process comprising the steps of (i) dissolving a polymer having a hydrophobic block in a water miscible solvent, (ii) dissolving a polynucleotide in an aqueous solution and (iii) combining the two to conjugate the polynucleotide to the hydrophobic block of the polymer and form the micelle.

Pharmaceutical Compositions

The compositions comprising a polymer or a polymeric micelle and an agent, such as a biomolecular agent (e.g., a polynucleotide), can be a pharmaceutical composition. Such pharmaceutical composition can comprise, for example, a polymer or a polymeric micelle, a biomolecular agent, such as a polynucleotide, and a pharmaceutically acceptable excipient.

Polymer and micelle compositions provided herein (e.g., those attached to one or more RNAi agent therapeutic agent, such as one or more oligonucleotide) are optionally provided in a composition (e.g., pharmaceutically acceptable composition). In some embodiments, a polymer or micelle composition provided herein is administered to a patient in any suitable manner, e.g., with or without stabilizers, buffers, and the like, to form a pharmaceutical composition. In some embodiments, the polymer or micelle composition provided herein is formulated and used as tablets, capsules or elixirs for oral administration, suppositories for rectal administration, sterile solutions, suspensions or solutions for injectable administration, and any other suitable compositions.

Provided are pharmaceutically acceptable formulations of a polymer or micelle composition comprising at least one RNAi therapeutic agent described herein. These formulations include salts of the above compounds, e.g., acid addition salts, e.g., salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, e.g., oral, transdermal, or by injection. Thus, in specific embodiments wherein the polymer or micelle composition comprises and is delivering a polynucleotide, the formulation is in a form that does not prevent the polymer or micelle composition and, more specifically, the polynucleotide (e.g., oligonucleotide or siRNA) from reaching a target cell with the polynucleotide intact and/or functional. For example, in certain embodiments, pharmacological compositions injected into the blood stream are soluble and/or dispersible. Moreover, pharmaceutical compositions described herein are, preferably, non-toxic. In some embodiments, wherein a polymer or micelle composition provided herein is administered for therapeutic benefit, a therapeutic effective amount of the composition comprising an RNAi therapeutic agent (e.g., a polynucleotide, such as an siRNA) is administered. In an exemplary embodiment, a therapeutically effective amount includes a sufficient amount of a polymer or micelle composition provided herein to provide about 10 mg or less of siRNA per kg of individual.

In some embodiments, pharmaceutical compositions comprising a polymer or micelle composition, which comprise an RNAi therapeutic agent (e.g., a polynucleotide, such as an siRNA), are administered systemically. As used herein, "systemic administration" means in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. In some embodiments, the compositions are administered topically.

In some embodiments, the compositions are prepared for storage or administration and include a pharmaceutically effective amount of the therapeutic agent comprising a polymer or micelle composition provided herein in a pharmaceutically acceptable carrier or diluent. Any acceptable carriers or diluents are optionally utilized herein. Specific carriers and diluents and are described, e.g., in Remington's Pharmaceutical Sciences, Mack Publishing Co., A. R. Gennaro Ed., 1985. For example, preservatives, stabilizers, dyes and flavoring agents are optionally added. These include sodium benzoate, sorbic acid and esters of p-hydroxybenzoic acid. In addition, antioxidants and suspending agents are optionally used. As used herein, the term "pharmaceutically acceptable carrier" means a non-toxic, inert solid, semi-solid or liquid filler, diluent, encapsulating material or formulation auxiliary of any type. Some examples of materials optionally used as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, the pharmaceutical compositions provided herein are administered to humans and/or to animals, orally, rectally, parenterally, intracistemally, intravaginally, intranasally, intraperitoneally, topically (as by powders, creams, ointments, or drops), bucally, or as an oral or nasal spray.

In various embodiments, liquid dosage forms for oral administration include pharmaceutically acceptable emulsions, microemulsions, solutions, suspensions, syrups, and elixirs. In addition to the active ingredients (i.e., micelle-oligonucleotide complexes provided herein), the liquid dosage forms optionally further contain inert diluents or excipients, such as by way of non-limiting example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions optionally also include adjuvants such as wetting agents, emulsifying and suspending agents, sweetening, flavoring, and perfuming agents.

In some embodiments, injectable preparations, for example, sterile injectable aqueous or oleaginous suspensions are formulated according in any suitable manner, e.g., using dispersing agents, wetting agents and/or suspending agents. The sterile injectable preparation is, optionally, a sterile injectable solution, suspension, or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil is optionally employed including synthetic mono- or diglycerides. In additional embodiments, fatty acids such as oleic acid are used in the preparation of injectables. In a specific embodiment, the polymer or micelle composition provided herein is solubilized in a carrier fluid comprising 1% (w/v) sodium carboxymethyl cellulose and 0.1% (v/v) Tween 80.

In some embodiments, the injectable formulations are sterilized, for example, by filtration through a bacteria-retaining filter, or by incorporating sterilizing agents in the form of sterile solid compositions which are optionally dissolved or dispersed in sterile water or other sterile injectable medium prior to use.

In certain embodiments, compositions for rectal or vaginal administration are suppositories. Suppositories are optionally prepared by mixing the therapeutic agent comprising a polymer or micelle composition provided herein with suitable non-irritating excipients or carriers such as cocoa butter, polyethylene glycol, or a suppository wax which are solid at ambient temperature but liquid at body temperature and therefore melt in the rectum or vaginal cavity and release a polymer or micelle composition provided herein.

Suitable solid dosage forms for oral administration include, by way of non-limiting example, capsules, tablets, pills, powders, and granules. In such solid dosage forms, a polymer or micelle composition provided herein comprising an RNAi therapeutic agent (e.g., oligonucleotide) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type are also optionally employed as fillers in soft and hard-filled gelatin capsules using such excipients as lactose or milk sugar as well as high molecular weight polyethylene glycols and the like.

In some embodiments, the solid dosage forms of tablets, dragees, capsules, pills, and granules are prepared with coatings and shells such as enteric coatings and other suitable coatings. They optionally contain opacifying agents. In certain embodiments, they are of a composition that they release the active ingredient(s) only, or preferentially, in a certain part of the intestinal tract, optionally, in a delayed manner. Examples of suitable embedding compositions include, by way of non-limiting example, polymeric substances and waxes.

Solid compositions of a similar type are optionally employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include, by way of non-limiting example, ointments, pastes, creams, lotions, gels, powders, solutions, sprays, inhalants, or patches. In some embodiments, therapeutic agents comprising a polymer or micelle composition provided herein are admixed under sterile conditions with a pharmaceutically acceptable carrier and, optionally, one or more preservative, one or more buffer, or a combination thereof (e.g., as may be required). Ophthalmic formulation, ear drops, and eye drops are also contemplated as being within the scope of this invention.

Ointments, pastes, creams, and gels provided herein optionally contain, in addition to the polymer or micelle composition provided herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays optionally contain, in addition to a polymer or micelle composition provided herein, excipients such as lactose, talc, silicic acid, aluminum hydroxide, calcium silicates, and polyamide powder, or mixtures of these substances. In some embodiments, sprays additionally contain customary propellants such as chlorofluorohydrocarbons.

Transdermal patches have the added advantage of providing controlled delivery of a compound to the body. Such dosage forms are made in any suitable manner, e.g., by dissolving or dispensing the microparticles or nanoparticles in a proper medium. Absorption enhancers are optionally used to increase the flux of the compound across the skin. The rate can be controlled by either providing a rate controlling membrane or by dispersing a polymer or micelle composition provided herein in a polymer matrix or gel.

In some aspects of the invention, a polymer or micelle composition provides some properties (e.g. mechanical, thermal, etc.) that are usually performed by excipients, thus decreasing the amount of such excipients required for the formulation.

Therapeutic Uses

Compositions comprising polymers or polymeric micelles and an agent such as a polynucleotide can be used in various methods.

Generally, such compositions can be used for example in a method for intracellular delivery of an agent such as a polynucleotide. The composition comprising a polymer or a polymeric micelle and an agent (e.g., a polynucleotide) associated therewith can be exposed to and contacted with a with a cell surface (e.g., via directed targeting) in a medium at a first pH. The composition is introduced into an endosomal membrane within the cell, for example, through endocytosis and, in some embodiments, through receptor mediated endocytosis. The endosomal membrane is destabilized (e.g., by a constituent polymer or block thereof, which is a membrane destabilizing polymer), thereby delivering the composition or the agent (e.g., polynucleotide) to the cytosol of the cell. The medium can be an in vitro medium. The medium can be an in vitro medium such as a physiological medium.

Generally, for example, such compositions can be used for modulating the activity of an intracellular target in a cell. The agent, such as a polynucleotide, can be delivered to the cytosol of a cell according to the method described in the immediately preceding paragraph. The agent (e.g., polynucleotide) is allowed to interact with the intracellular target, thereby modulating the activity of the intracellular target.

More specifically, for example, in some embodiments, the compositions comprising polymers or polymeric micelles (e.g., micelles) provided herein are useful in treating a subject at risk for or afflicted with disorders associated with and/or caused by high plasma levels or cholesterol, apolipoprotein b, and/or LDL cholesterol, e.g., hypercholesterolemia. In certain embodiments, the treatment comprises providing a polymeric micelle and a therapeutic agent (e.g., an oligonucleotide agent) associated therewith, wherein the therapeutic agent silences (e.g., by cleavage) a gene, or a gene product that promotes such condition. In some embodiments the therapeutic agent (e.g., an oligonucleotide or RNAi agent) silences proprotein convertase subtilisin/kexin type 9 (PCSK9) gene responsible for regulation of low density lipoprotein (LDLR) levels and function and, thus, polymers or polymeric micelles comprising such therapeutic agents are used to treat a subject having or at risk for a disorder characterized by unwanted PCSK9 expression, e.g., disorders associated with and/or caused by high plasma levels or cholesterol, apolipoprotein b, and/or LDL cholesterol, e.g., hypercholesterolemia. In some embodiments, the polymers or polymeric micelles deliver a PCSK9 silencing polynucleotide agent (e.g., siRNA) to a cell expressing PCSK9. In some embodiments, the cell is a liver cell.

In some embodiments, the polymers or polymeric micelles (e.g., micelles) provided herein are useful in treating a subject at risk for or afflicted with unwanted cell proliferation (e.g., malignant or nonmalignant cell proliferation). The treatment comprises providing a composition comprising a polymer or a polymeric micelle and a therapeutic agent (e.g., an oligonucleotide agent), wherein the therapeutic agent can silence (e.g., by cleavage) a gene or a gene product that promotes unwanted cell proliferation; and administering a therapeutically effective dose of the polymer or polymeric micelle to a subject (e.g., a human subject). In some embodiments, the therapeutic agent is a polynucleotide (e.g., an oligonucleotide) that is homologous to and can silence (e.g., by cleavage) a gene.

In certain embodiments, the gene is, but is not limited to, a growth factor or growth factor receptor gene, a phosphatase, a kinase, e.g., a protein tyrosine, serine, or threonine kinase gene, an adaptor protein gene, a gene encoding a G protein superfamily molecule, or a gene encoding a transcription factor. In some instances, the composition comprises a polymer or a polymeric micelle and a polynucleotide that silences a gene that is expressed in a specific tissue or organ including, but not limited to, lung, pancreas, liver, kidney, ovary, muscle, skin, breast, colon, stomach, and the like.

In some embodiments, the oligonucleotide agent silences one or more of the following genes the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers and chronic leukemia; the MEKK gene, and thus can be used to treat a subject having or at risk for a disorder characterized by unwanted MEKK expression, e.g., squamous cell carcinoma, melanoma, or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA (p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL 2 gene, and thus can be used to treat a subject having or at risk for a disorder characterized by unwanted BCL-2 expression, e.g., lung or prostate cancers or Non Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-1 gene, and thus can be used to treat a subject having or at risk for a disorder characterized by unwanted WNT 1 expression, e.g., basal cell carcinoma; the beta catenin gene, and thus can be used to treat a subject having or at risk for a disorder characterized by unwanted beta catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the Topoisomerase I gene, and thus can be used to treat a subject having or at risk for a disorder characterized by unwanted Topoisomerase I expression, e.g., ovarian and colon cancers; the Topoisomerase II alpha gene, and thus can be used to treat a subject having or at risk for a disorder characterized by unwanted Topoisomerase II expression, e.g., breast and colon cancers.

In other embodiments the oligonucleotide agent silences mutations in one of the following genes: the p73 gene, and thus can be used to treat a subject having or at risk for a disorder characterized by unwanted p73 expression, e.g., colorectal adenocarcinoma; the p21(WAF1/CIP1) gene, and thus can be used to treat a subject having or at risk for a disorder characterized by unwanted p21(WAF1/CIP1) expression, e.g., liver cancer; the p27(KIP1) gene, and thus can be used to treat a subject having or at risk for a disorder characterized by unwanted p27(KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the oligonucleotide agent silences mutations in tumor suppressor genes and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN p63, the pRb tumor suppressor gene, the APC1 tumor suppressor gene, the BRCA1 tumor suppressor gene, the PTEN tumor suppressor gene.

In some embodiments the oligonucleotide agent silences one of the following fusion genes: mLL fusion genes, e.g., mLL AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEL/AML1 fusion gene, and thus can be used to treat a subject having or at risk for a disorder characterized by unwanted TEL/AML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some aspects herein the compositions comprising the polymers or polymeric micelles and an agent, such as a polynucleotide, provide therapeutic agents for treating a subject, e.g., a human, at risk for or afflicted with a disease or disorder that may benefit by angiogenesis inhibition e.g., cancer or retinal degeneration. The treatment comprises providing a polymer or a polymeric micelle comprising an oligonucleotide agent, wherein said oligonucleotide agent is homologous to and/or can silence, e.g., by cleavage, a gene that mediates angiogenesis (e.g., VEGF R1, VEGF R2, or gene encoding signaling proteins for these receptors' pathways); and administering a therapeutically effective dosage of said polymer or polymeric micelle comprising the oligonucleotide agent to a subject, e.g., a human subject.

In some embodiments the oligonucleotide agent silences one of the following genes: the alpha v integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the composition comprising polymers pr polymeric micelles and an oligonucleotide agent relate to a method of treating a subject infected with a virus or at risk for or afflicted with a disorder or disease associated with a viral infection. The method comprises providing a polymer or a polymeric micelle comprising an oligonucleotide agent, wherein said oligonucleotide agent is homologous to and/or can silence, e.g., by cleavage, a viral gene or a cellular gene that mediates viral function, e.g., entry or growth; and administering a therapeutically effective dose of said oligonucleotide agent to a subject, e.g., a human subject.

In some embodiments, the composition comprising polymers or polymeric micelles and an oligonucleotide agent are useful in treatment of subjects infected with the Human Papilloma Virus (HPV) or at risk for or afflicted with a disorder mediated by HPV, e.g., cervical cancer.

In some embodiments, a composition comprising a polymer or a polymeric micelle and an oligonucleotide agent silencing expression of a HPV gene is reduced. In some embodiments, the HPV gene is selected from the group of E2, E6, or E7.

In another embodiment the expression of a human gene that is required for HPV replication is reduced.

In some embodiments, the composition comprises a polymer or a polymeric micelle and an oligonucleotide agent useful in treating patients infected by the Human Immunodeficiency Virus (HIV) or at risk for or afflicted with a disorder mediated by HIV, e.g., Acquired Immune Deficiency Syndrome (AIDS). In some embodiments, the expression of an HIV gene is reduced. In other embodiments, the HIV gene is CCR5, Gag, or Rev. In some embodiments the expression of a human gene that is required for HIV replication is reduced. In some embodiments, the gene is CD4 or Tsg101.

In some embodiments, the composition comprises a polymer or a polymeric micelle and an oligonucleotide agent useful for treating patients infected by the Hepatitis B Virus (HBV) or at risk for or afflicted with a disorder mediated by HBV, e.g., cirrhosis and heptocellular carcinoma. In one embodiment, the expression of a HBV gene is reduced. In another embodiment, the targeted HBV gene encodes one of the groups of the tail region of the HBV core protein, the pre cregious (pre c) region, or the cregious (c) region. In other embodiments, a targeted HBV RNA sequence is comprised of the poly(A) tail. In some embodiments, the expression of a human gene that is required for HBV replication is reduced.

In some embodiments, the composition comprises a polymer or a polymeric micelle and an oligonucleotide agent useful for treating patients infected with or at risk for or afflicted with a disorder mediated by a virus selected from the following viruses: the Hepatitis A Virus (HAV); Hepatitis C Virus (HCV); any of the group of Hepatitis Viral strains comprising Hepatitis D, E, F, G, or H; the Respiratory Syncytial Virus (RSV); the herpes Cytomegalovirus (CMV); the herpes Epstein Barr Virus (EBV); Kaposi's Sarcoma associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick borne encephalitis flavivirus; the Murray Valley encephalitis flavivirus; the dengue flavivirus; the Simian Virus 40 (SV40); the encephalomyocarditis virus (EMCV); the measles virus (MV); the Varicella zoster virus (VZV); an adenovirus (e.g., virus causing a respiratory tract infection); the poliovirus; or a poxvirus (a poxvirus causing smallpox). In some embodiments, the expression of a human gene that is required for the replication of these viruses is reduced.

In some embodiments, the composition comprises a polymer or a polymeric micelle and an oligonucleotide agent useful for treating patients infected by the Herpes Simplex Virus (HSV) or at risk for or afflicted with a disorder mediated by HSV, e.g., genital herpes and cold sores, as well as life threatening or sight impairing disease, e.g., mainly in immunocompromised patients. In some embodiments, the expression of a HSV gene is reduced. In other embodiments, the targeted HSV gene encodes DNA polymerase or the helicase primase. In some embodiments the expression of a human gene that is required for HSV replication is reduced.

In some embodiments, the composition comprises a polymer or a polymeric micelle and an oligonucleotide agent useful for treating patients infected by the West Nile Virusor at risk for or afflicted with a disorder mediated by West Nile Virus. In some embodiments, the expression of a West Nile Virus gene is reduced. In other preferred embodiments, the West Nile Virus gene is selected from the group comprising E, NS3, or NS5. In some embodiments, the expression of a human gene that is required for West Nile Virus replication is reduced.

In some embodiments, the polymer or polymeric micelle comprises an oligonucleotide agent useful for treating patients infected by the Human T Cell Lymphotropic Virus (HTLV) or a disease or disorder associated with this virus, e.g., leukemia or myelopathy. In some embodiments, the expression of a HTLV gene is reduced. In some embodiments, the HTLV1 gene is the Tax transcriptional activator. In some embodiments, the expression of a human gene that is required for HTLV replication is reduced.

In some aspects, the composition comprises a polymer or a polymeric micelle and an oligonucleotide agent useful for treating a subject infected with a pathogen, e.g., a bacterial, amoebic, parasitic, or fungal pathogen. The method of treatment comprises providing a polymer or a polymeric micelle comprising an oligonucleotide agent, wherein said oligonucleotide is homologous to and/or can silence, e.g., by cleavage of a pathogen gene or a gene involved in the pathogen's growth; and administering a therapeutically effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production.

Thus, in some embodiments, the composition comprises a polymer or a polymeric micelle and an oligonucleotide agent useful for of treating patients infected by a plasmodium that causes malaria. In some embodiments, the expression of a plasmodium gene is reduced. In other embodiments, the gene is apical membrane antigen 1 (AMA1). In some embodiments, the expression of a human gene that is required for plasmodium replication is reduced.

In some embodiments, the polymer or polymeric micelle comprises an oligonucleotide agent useful for treating patients infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is reduced.

In some embodiments, the diseases treated by the compositions comprising a polymer or a polymeric micelle and an agent as provided herein may be systemic or present in a specific tissue, e.g., the lung, skin, liver, breast, kidney, pancreas, CNS, or the like. In certain aspects, the oligonucleotide silences a gene that mediates or is involved in a metabolic disease or disorder, e.g., diabetes, obesity, and the like. In certain embodiments, the oligonucleotide silences a gene that mediates or is involved in a pulmonary disease or disorder, e.g., chronic obstructive pulmonary disease (COPD), cystic fibrosis, or lung cancer. In some aspects herein, the polymers or polymeric micelles comprise an oligonucleotide agent useful for and/or related to a method of treating a subject, e.g., a human, at risk for or afflicted with a disease or disorder characterized by an unwanted immune response, e.g., an inflammatory disease or disorder or an autoimmune disease or disorder. The method comprises providing a polymer or a polymeric micelle comprising an oligonucleotide agent, wherein said oligonucleotide agent is homologous to and/or can silence, e.g., by cleavage, a gene that mediates an unwanted immune response; and administering said oligonucleotide agent to a subject, e.g., a human subject. In some embodiments, the disease or disorder is an ischemia or reperfusion injury, e.g., ischemia or reperfusion injury associated with acute myocardial infarction, unstable angina, cardiopulmonary bypass, surgical intervention, e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention, e.g., angioplasty, e.g., percutaneous transluminal coronary angioplasty. In other embodiments, the disease or disorder is Inflammatory Bowel Disease, e.g., Crohn's Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type II diabetes, arthritis, e.g., rheumatoid or psoriatic. In certain embodiments, the oligonucleotide agent silences an integrin or co ligand thereof, e.g., VLA4, VCAM, ICAM. In other embodiments the oligonucleotide agent silences a selectin or co ligand thereof, e.g., P selectin, E selectin (ELAM), I selectin, P selectin glycoprotein 1 (PSGL 1). In certain embodiments, the oligonucleotide agent silences a component of the complement system, e.g., C3, C5, C3aR, C5aR, C3, convertase, and C5 convertase. In some embodiments, the oligonucleotide agent silences a chemokine or receptor thereof, e.g., TNFI, TNFJ, IL 1I, IL 1J, IL 2, IL 2R, IL 4, IL 4R, IL 5, IL 6, IL 8, TNFRI, TNFRII, IgE, SCYA11, and CCR3. In other embodiments the oligonucleotide agent silences GCSF, Gro1, Gro2, Gro3, PF4, MIG, Pro Platelet Basic Protein (PPBP), MIP 1I, MIP 1J, RANTES, MCP 1, MCP 2, MCP 3, CMBKR1, CMBKR2, CMBKR3, CMBKR5, AIF 1, or I 309.

In some aspects, the composition comprises a polymer or a polymeric micelle and an oligonucleotide agent useful for treating a subject, e.g., a human, at risk for or afflicted with a neurological disease or disorder. The method comprises providing a polymer or a polymeric micelle comprising an oligonucleotide agent, wherein said oligonucleotide is homologous to and/or can silence, e.g., by cleavage, a gene that mediates a neurological disease or disorder; and administering a therapeutically effective dose of said oligonucleotide agent to a subject, e.g., a human. In some embodiments, the disease or disorder is Alzheimer Disease or Parkinson Disease. In certain embodiments, the oligonucleotide agent silences an amyloid family gene, e.g., APP; a presenilin gene, e.g., PSEN1 and PSEN2, or I synuclein. In other embodiments, the disease or disorder is a neurodegenerative trinucleotide repeat disorder, e.g., Huntington disease, dentatorubral pallidoluysian atrophy, or a spinocerebellar ataxia, e.g., SCA1, SCA2, SCA3 (Machado Joseph disease), SCA7 or SCA8. In some embodiments, the oligonucleotide agent silences HD, DRPLA, SCA1, SCA2, MJD1, CACNL1A4, SCA7, or SCA8.

In certain aspects the composition comprises a polymer or a polymeric micelle and an oligonucleotide agent capable of cleaving or silencing more than one gene. In these embodiments, the oligonucleotide agent is selected so that it has sufficient homology to a sequence found in more than one gene, e.g., a sequence conserved between these genes. Thus in some embodiments, an oligonucleotide agent targeted to such sequences effectively silences the entire collection of genes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. The following examples provide various illustrative embodiments of the invention as well as synthesis methods and various biological and other activity parameters. The examples, however, provide details concerning only some of the embodiments of the invention and are not intended to be limiting. It is intended that the following claims define the scope of the invention and that methods and structures within the scope of these claims and their equivalents be covered thereby

EXAMPLES

Throughout the description of the present invention, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "HPMA" represents 2-hydroxypropyl methacrylamide or monomeric residue derived therefrom; "HPMAE" represents 2-hydroxypropyl methacrylate or monomeric residue derived therefrom; "MAA" represents methylacrylic acid or monomeric residue derived therefrom; "MAA(NHS)" represents N-hydroxyl-succinimide ester of methacrylic acid or monomeric residue derived therefrom; "PAA" (or the letter "P" as equivalent shorthand notation) represents 2-propylacrylic acid or monomeric residue derived therefrom, "PEGMA" refers to the pegylated methacrylic monomer, $CH_3-O-(CH_2CH_2O)_nC(O)C(CH_3)CH_2$ or monomeric residue derived therefrom (PEGMA$_n$; n=8-9; n=4-5), and PDSMA refers to 2-(2-pyridyldisulfide substituted)ethyl methacrylate. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

| Monomer | Structure |
| --- | --- |
| 1 Propyl acrylic acid, PAA or P | 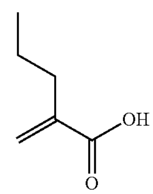 |
| 2 Dimethylaminoethyl methacrylate; DMAEMA or D | 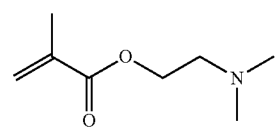 |
| 3 Butyl methacrylate; BMA or B | 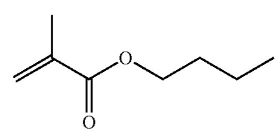 |
| 5 PDSMA | 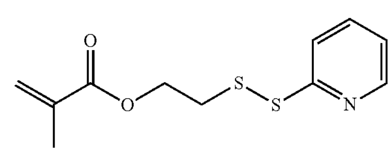 [SMILES: C=C(C)C(=O)OCCSSc1ccccn1] |
| 6 PEGMA$_n$ | 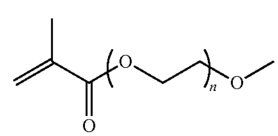 |
| 7 Boc-protected primary amine monomer; BPAM | 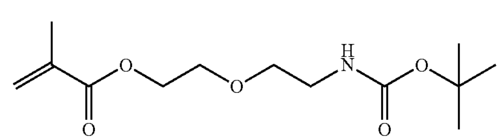 [SMILES: C=C(C)C(=O)OCCOCCNC(=O)OC(C)(C)C] |
| 12 2-hydroxypropyl methacrylate; HPMAE | 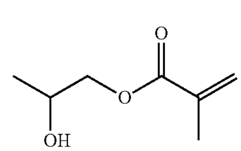 |

| Monomer | Structure |
|---------|-----------|
| 14 FA-PEG$_n$-MA (as a 1:3 mixture of α and γ isomers) | 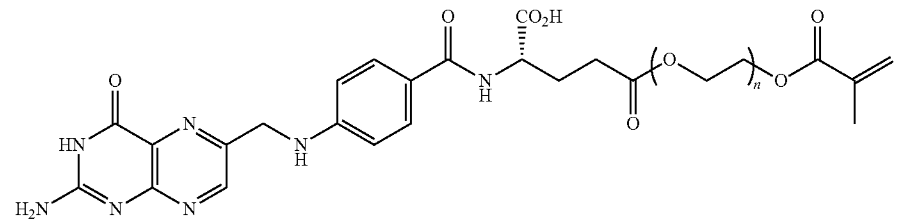 |

<sup>1</sup>H NMR spectra of the monomers and polymers were recorded on Bruker AV301 in deuterated solvents as indicated in each experiment at 25° C. Gel permeation chromatography (GPC) was used to determine molecular weights and polydispersities (PDI, $M_w/M_n$) of the copolymer samples in DMF using a Viscotek GPCmax VE2001 and refractometer VE3580 (Viscotek, Houston, Tex.). HPLC-grade DMF containing 1.0 wt % LiBr was used as the mobile phase. UV/Vis spectroscopy was performed using a NanoDrop UV/Vis spectrometer (path length 0.1 cm). Particle sizes of the polymer and polymer-siRNA conjugate particles were measured by dynamic light scattering using a Malvern Zetasizer Nano ZS. Cyano-4-(ethylsulfanylthiocarbonyl)sulfanylpentanoic acid (ECT) was used as the chain transfer agent (CTA) in the synthesis of MacroCTAs and single-block copolymers, and azobisisobutyronitrile (AIBN) (Wako chemicals) was used as the radical initiator in all polymerization reactions, unless stated otherwise. Monomers were from commercial sources, unless indicated otherwise, and were purified from traces of stabilizing agents prior to their use in polymerization reactions.

Example 1

Synthesis of Folate Monomer FA-PEG$_1$-MA

Example 1-2

Synthesis of FA-PEG$_1$-MA

To a 250 mL one neck round-bottom flask was added folic acid (500 mg, 1.13 mmol) and anhydrous dimethyl sulfoxide (18 mL). This solution was stirred at room temperature under a flow of inert argon gas until all folic acid was completely dissolved (3-4 hours). Then anhydrous pyridine (5.0 mL) was added followed by 2-hydroxethyl methacrylate (2.8 mL, 22.6 mmol) and 4-dimethylaminopyridine (138 mg, 1.13 mmol, DMAP). To this solution, a solution of N,N'-dicyclohexylcarbodiimide (DCC, 233 mg, 1.13 mmol) in anhydrous dimethyl sulfoxide (2.0 mL) was added in one portion. After the DCC reagent was added the reaction was stirred at room temperature for 18 h.

After stirring the reaction for 18 h the reaction mixture was filtered to remove the insoluble urea by-product (DCU). The mother liquor was then precipitated by dropwise addition into a vigorously stirred solution of diethyl ether (150 mL). The precipitate was collected and triturated with acetone (2×100 mL) until DMAP remained only a minor contaminate as determined by <sup>1</sup>H NMR.

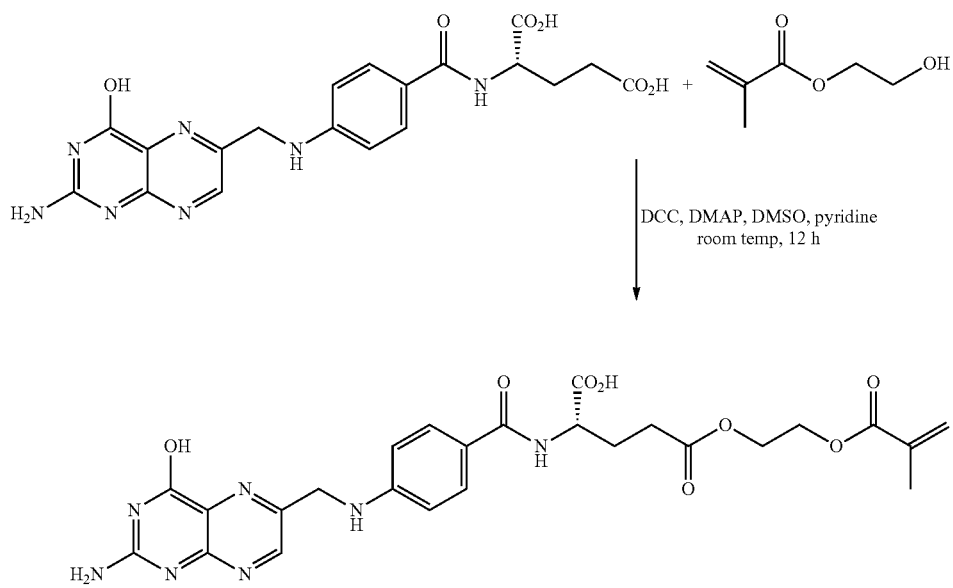

The triturated product was transferred to a 50 mL one-neck round-bottom flask and all solvents were thoroughly removed under reduced pressure via rotary evaporation providing 290 mg (46.3%) of the product as an orange solid. The orange solid was then stored at −80° C. until its use in RAFT polymerization.

The final compound was analyzed by $^1$H NMR using DMSO-$d_6$ with a few drops of $D_2O$. The NMR spectra of the product contained signals attributed to folic acid protons as well the olefin signals at δ 5.98 and 5.63 ppm. No unsubstituted folic acid was present in the final product. The ratio of the α- and γ-substituted products in the final folate material was determined to be 1:3 (by $^1$H NMR). Additionally, the final product contained a small amount (ca. 25 mole % impurity) of DMAP. The two isomeric products can be separated by reverse phase HPLC.

Example 1-2

Synthesis and HPLC purification of FA-PEG$_1$-MA

FA-PEG$_1$-MA was synthesized according to the method of the Example 1-1 using a solution of folic acid (2.5 g, 5.67 mmol) in anhydrous dimethyl sulfoxide (90 mL), anhydrous pyridine (25.0 mL), 2-hydroxyethyl methacrylate (13.8 mL, 113.4 mmol), 4-dimethylaminopyridine (693 mg, 5.67 mmol, DMAP), and a solution of N,N'-dicyclohexylcarbodiimide (DCC, 1.17 mg, 5.67 mmol) in anhydrous dimethyl sulfoxide (10.0 mL).

Purification of the product was carried out as follows. After the removal of DCC byproduct by filtration, the mother liquor was added dropwise into a vigorously stirred diethyl ether (300 mL). The precipitate was collected, resuspended in ether, and separated by centrifugation. After repeating this process twice, the precipitate was collected, triturated with acetone to remove residual DMSO, and dried to yield 1.73 g of crude product as a yellow-orange solid.

The crude product was dissolved in a minimal amount of DMSO and purified by C8 semi-preparative reverse phase HPLC (Phenomenex, Luna C8 AXIA Pack, 250×21.2 mm; isocratic elution with 5% of $CH_3CN$ in 0.01% TFA for 10 minutes, linear gradient from 5% to 50% $CH_3CN$ in 0.01% TFA for 30 min; flow rate 15 mL/min). The peak eluting at 27.1 min was collected, all solvents were thoroughly removed under reduced pressure. The purified product was stored at −80° C. until its use in RAFT polymerization.

The final compound was analyzed by $^1$H NMR using DMSO-$d_6$ with a few drops of $D_2O$. The NMR spectra of the product contained signals attributed to folic acid protons as well the olefin signals at δ 5.98 and 5.63 ppm. No unsubstituted folic acid was present in the final product. The ratio of the α- and γ-substituted products in the final folate material was determined to be 1:3 (by $^1$H NMR).

Example 2

Synthesis of Folate Monomer FA-PEG$_4$-MA

Example 2-1

Synthesis of PEG$_4$-MA Linker

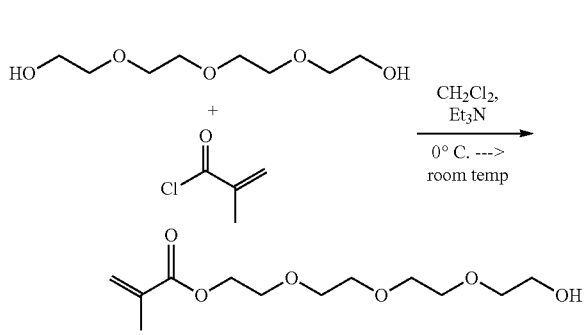

To a 1000 mL one-neck round-bottom flask was added tetraethylene glycol (41.4 mL, 240 mmol) followed by anhydrous $CH_2Cl_2$ (650 mL), and triethylamine (33.5 mL, 240 mmol). This mixture was stirred at 0° C. for 5 min under a flow of argon gas. To a 100 mL addition funnel was added anhydrous $CH_2Cl_2$ (50 mL) and methacryloyl chloride (18.7 mL, 191.4 mmol). The methacryloyl chloride solution was then added drop wise into the cooled reaction mixture over 30 min. After the addition was complete the homogeneous mixture was stirred at 0° C. for 30 min then warmed to room temperature over 30 min. The solution was then stirred at room temperature overnight before being worked-up.

The reaction progress was followed by TLC using $SiO_2$ stationary phase with 100% EtOAc as mobile phase. The desired product had an Rf=0.21. The reaction mixture components were visualized on TLC plates by short wave UV and $KMnO_4$ staining solution.

After stirring at room temperature overnight the mixture was diluted with $CH_2Cl_2$ (100 mL) and washed with a saturated aqueous solution of $NaHCO_3$ (1×150 mL) then washed with $H_2O$ (2×100 mL). The organic layer was separated, dried over $Na_2SO_4$, filtered, and concentrated under reduced pressure to provide the crude product as a colorless oil. The crude product was then dissolved in $CH_2Cl_2$ (25 mL) and purified using column chromatography ($SiO_2$, column size 7.5 cm ID×13.0 cm length, isocratic elution using 100% hexanes for 500 mL, linear gradient to 100% EtOAc over 1000 mL, then isocratic elution with EtOAc and MeOH (19:1, v/v)). The fractions containing only the desired product ($R_f$=0.21) were combined and the solvent thoroughly evaporated providing 18.47 g (37%) of the desired product with good purity (>95%) by $^1$H NMR. The final material cannot be subjected to high vacuum for a significant amount of time. If the product is placed under high vacuum for longer than 1.0 h, it might self polymerize. Accordingly, the product was only rotary evaporated and then directly placed at −80° C. for long term storage.

Example 2-2

Synthesis of FA-PEG$_4$-MA

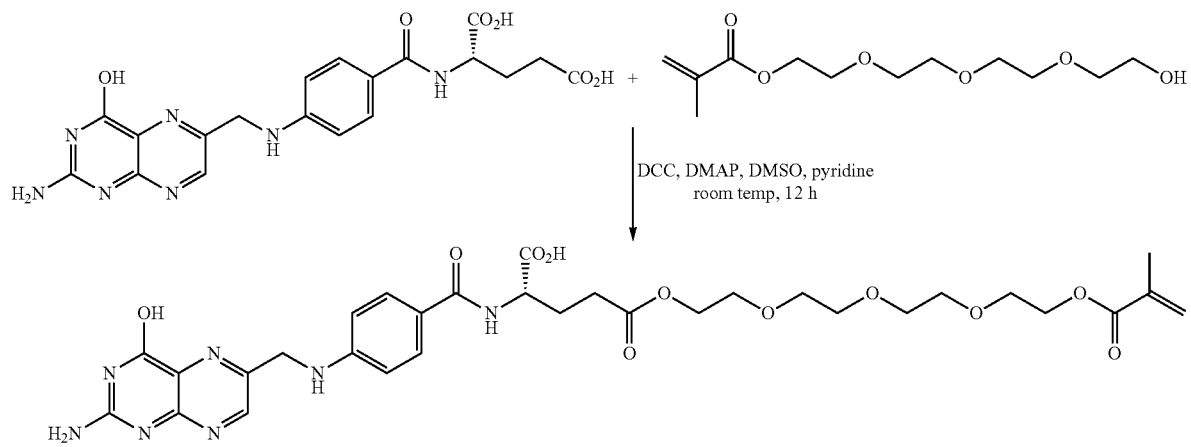

The synthesis of FA-PEG$_4$-MA was performed analogously to the synthesis of FA-PEG$_1$-MA using folic acid (500 mg, 1.13 mmol), pyridine (5 mL), PEG$_4$-MA alcohol (4.2 g, 16 mmol), DCC (233 mg, 1.13 mmol) and DMAP (138 mg, 1.13 mmol) in anhydrous DMSO (20 mL).

Example 3

Synthesis of FA-PEG$_1$-MA Triblock Copolymer

Example 3-1

RAFT Co-Polymerization of PEGMA$_{8-9}$ with FA-PEG$_1$-MA at 68° C.

TABLE 1

| Name | FW (g/mol) | Equiv. | mol | Weight | Actual weight |
| --- | --- | --- | --- | --- | --- |
| PEGMA$_{8-9}$ | 475 | 42.5 | $1.05 \times 10^{-3}$ | 0.500 g | 0.520 g |
| FA-PEG$_1$-MA | 553.2 | 7.5 | $1.85 \times 10^{-4}$ | 0.103 g | 0.100 g |
| ECT | 263.4 | 1 | $2.48 \times 10^{-5}$ | 0.007 g | 0.007 g |
| AIBN | 164.21 | 0.05 | $1.24 \times 10^{-6}$ | 0.203 mg | 0.203 mg |

[PEGMA]:[FAMA] = 85:15, DMSO = 2.0 g; N$_2$ Purging: 22 min; 68° C.; polymerization time = 4 h FA-PEG$_1$-MA monomer (0.100 g), ECT (7 mg), and AIBN (0.203 mg, CTA:AIBN 20:1) and DMSO (2.0 g) were introduced under nitrogen into a sealed vial. The mixture was then degassed by bubbling nitrogen into the mixture for 22 minutes and then was placed in a reaction block (67-68° C.; stirring speed 350 rpm). After 4 hrs, the reaction was stopped by placing the vial in ice and exposing the mixture to air. The purification of the final polymer was done by dialysis against DMSO (0.5 L×6) followed by dialysis against methanol (0.5 L×8) using a MWCO membrane 3.5K. The structure and composition were verified by $^1$H NMR, which also verified the absence of residual vinyl groups from un-incorporated monomers. Purity of the polymer was confirmed by GPC analysis. M$_{n,GPC}$=10,000 g/mol, dn/dc=0.0615, PDI=1.10.

Example 3-2

RAFT Co-Polymerization of PEGMA$_{4-5}$, PDSMA and BPAM in DMF at 68° C. Using p[PEGMA$_{8-9}$-co-FA-PEG$_1$-MA]-macroCTA

TABLE 2

| [PEGMA$_{4-5}$]:[PDSMA]:[BPAM] = 85:7.5:7.5 | | | | | |
| --- | --- | --- | --- | --- | --- |
| Name | FW (g/mol) | Equiv. | mol | Weight | Actual weight |
| PEGMA$_{4-5}$ | 300 | 42.5 | $6.205 \times 10^{-4}$ | 0.1862 g | 0.1997 g |
| PDSMA | 255.36 | 3.75 | $5.475 \times 10^{-5}$ | 0.014 g | 0.0163 g |
| BPAM | 273.33 | 3.75 | $5.475 \times 10^{-5}$ | 0.015 g | 0.1072 g |
| macroCTA | 10000 | 1 | $1.46 \times 10^{-5}$ | 0.146 g | 0.146 g |
| AIBN | 164.21 | 0.1 | $1.46 \times 10^{-6}$ | 0.24 mg | 0.24 mg |

DMF = 0.43 g; N$_2$ Purging: 25 min; temp. = 68° C.; polymerization time = 1 h 40 m Monomers, macroCTA, AIBN and DMF were placed in a 20 mL glass vial. The reaction vial was then degassed by bubbling nitrogen into the mixture for 25 minutes. The polymerization reaction was started by putting the reaction vial to a pre-heated reaction block at 68° C. After 1 h 40 m the reaction was stopped by placing the vial in ice and exposing the mixture to air. The purification of the final polymer was done by dialysis against methanol, and the product was dried under vacuum. The structure and composition were verified by $^1$H NMR, which also verified the absence of residual vinyl groups from un-incorporated monomers. Purity of the polymer was confirmed by GPC analysis. M$_{n,GPC}$=18,000 g/mol, dn/dc=0.0555, PDI=1.19.

Example 3-3

RAFT Synthesis of p[PEGMA$_{8-9}$-co-FA-PEG$_1$-MA]-b-p[PEGMA$_{4-5}$-co-PDSMA-co-BPAM]-b-p[BMA-PAA-DMAEMA] Triblock Co-Polymer

TABLE 3

| Name | FW (g/mol) | Equiv. | mol | Weight | Actual weight |
|---|---|---|---|---|---|
| BMA | 142.20 | 144 | 1.696 × 10$^{-3}$ | 0.2412 g | 0.2476 g |
| PAA | 114.14 | 72 | 8.48 × 10$^{-4}$ | 0.0968 g | 0.1043 g |
| DMAEMA | 157.21 | 72 | 8.48 × 10$^{-4}$ | 0.1333 g | 0.1367 g |
| macroCTA | 18000 | 1 | 1.1778 × 10$^{-5}$ | 0.212 g | 0.212 g |
| AIBN | 164.21 | 0.1 | 1.1778 × 10$^{-6}$ | 0.193 mg | 0.193 mg |

[BMA]:[PAA]:[DMAEMA] = 50:25:25; DMF = 0.94 g; N$_2$ Purging: 22 min; temp. = 68° C. Polymerization time = 9 h;

BMA and DMAEMA were purified by passing through a basic alumina column just before use. MacroCTA was placed in a 20 mL reaction glass vial. Required amount of DMF and AIBN stock solution in DMF were added to the glass vial. When the macroCTA was dissolved, required amount of BMA, PAA and DMAEMA were added to the reaction vial. The reaction mixture was then degassed by bubbling nitrogen into the mixture for 22 minutes. The polymerization reaction was started by putting the reaction vial to a pre-heated reaction block at 68° C. After 9 hr, the reaction was stopped by placing the vial in ice and exposing the mixtures to air. The polymer was precipitated from DMF into hexane/ether 75/25. Then, the polymer was dissolved in acetone and precipitated into hexane/ether 75/25 (two times). The resulting polymer was dried under vacuum for 7 hr. The structure and composition were verified by $^1$H NMR, which also verified the absence of residual vinyl groups from un-incorporated monomers. Purity of the polymer was confirmed by GPC analysis. $M_{n,GPC}$=31,000 g/mol, dn/dc=0.0554, PDI=1.41.

Example 4

Copolymerization of HPMAE (2-hydroxypropyl methacrylate) with FA-PEG$_1$-MA

RAFT polymerization was employed to synthesize poly(HPMAE-co-FA-PEG$_1$-MA) at two different molecular weights using 2,2-azobisisobutyronitrile (AIBN) as the primary radical source and the trithiocarbonate ethyl cyanovaleric acid trithiocarbonate (ECT) as the RAFT chain transfer agent. Polymerization A was designed to yield a polymer of approximately 5,000 g/mol, while polymerization B targeted a polymer of approximately 3,500 g/mol. The HPMAE/FA-PEG$_1$-MA molar feed ratio varied slightly between the polymerizations in order to obtain polymer blocks incorporating ~2 FA-PEG$_1$-MA repeat units per polymer chain. Following polymerization, p[HPMAE-co-FA-PEG$_1$-MA] was purified from residual monomers by extensive dialysis against DMSO (e.g., 1×2 L, 4×1 L, 72 hrs) followed by dialysis against MeOH (e.g., 3×3 L, 24 hrs). All dialysis was performed using Spectrapor dialysis membranes with MWCO=2,000 g/mol. Isolated polymers were obtained by rotary evaporation of the solvent and dried under vacuum. Absolute polymer molecular weight distributions were determined by GPC equipped with laser light scattering and the polymer composition was determined by $^1$H-NMR. The specific polymerization conditions utilized for Polymerization A and B are provided below along with GPC and NMR data.

Example 4-1

Polymerization A

HPMAE, FA-PEG$_1$-MA and ECT were combined in a vial with ~1.3 g DMSO and stirred until all monomers were completely dissolved. The [HPMAE]:[FA-PEG$_1$-MA] feed ratio was 93:7 and the [M$_o$]/[CTA$_o$] ratio was 60:1. A stock solution of AIBN was prepared in DMSO at a concentration of 3.9 mg/mL and the appropriate volume was added to the polymerization vial to achieve a [CTA$_o$]/[I$_o$] ratio of 10:1. The final monomer concentration of the solution was 30 wt % (1.9 M). The reaction vial was purged with N$_2$ and the polymerization was conducted at 68° C. for 3.5 hours under a N$_2$ atmosphere to reach a targeted conversion of 50%. The reaction was stopped by placing the vial in ice and exposing the mixture to air. p[HPMAE-co-FA-PEG$_1$-MA] was isolated and purified as described above. The product is characterized $^1$H-NMR and GPC.

TABLE 4

| Name | FW (g/mol) | Equiv. | Mol | Weight | Actual weight |
|---|---|---|---|---|---|
| HPMAE | 144.2 | 56 | 0.0023 | 0.3357 g | 0.3269 g |
| FA-PEG$_1$-MA* | 553.2 | 4 | 1.663e-4 | 0.0920 g | 0.0944 g |
| ECT | 263.4 | 1 | 4.158e-5 | 11.0 mg | 11.3 mg |
| AIBN | 164.21 | 0.1 | 4.158e-6 | 0.68 mg | from stock soln |

*FA-PEG$_1$-MA, controlling reagent. 275 mg batch split between A and B. AIBN stock solution: 3.9 mg AIBN in 1 mL (1.1066 g) DMSO, for 0.68 mg AIBN add 174 μL AIBN solution; N$_2$ purge = 30 min; T = 68° C., t = 3.5 h.

Example 4-2

Polymerization B

HPMAE, FA-PEG$_1$-MA and ECT were combined in a vial with ~2.1 g DMSO and stirred until all monomers were completely dissolved. The [HPMAE]:[FA-PEG$_1$-MA] feed ratio was 90:10 and the [M$_o$]/[CTA$_o$] ratio was 54:1. A stock solution of AIBN was prepared in DMSO at a concentration of 3.9 mg/mL and the appropriate volume was added to the polymerization vial to achieve a [CTA$_o$]/[I$_o$] ratio of 10:1. The final monomer concentration of the solution was 25 wt % (1.3 M). The reaction vial was purged with N$_2$ and the polymerization was conducted at 68° C. for 3.5 hours under a N$_2$ atmosphere to reach a targeted conversion of 50%. The reaction was stopped by placing the vial in ice and exposing the mixture to air. p[HPMAE-co-FA-PEG$_1$-MA] was isolated and purified as described above. The product is characterized $^1$H-NMR and GPC.

TABLE 5

| Name | FW (g/mol) | Equiv. | Mol | Weight |
|---|---|---|---|---|
| HPMAE | 144.2 | 35 | 0.0029 | 0.4164 g |
| FA-PEG$_1$-MA* | 553.2 | 4 | 3.308e-4 | 0.183 g |

TABLE 5-continued

| Name | FW (g/mol) | Equiv. | Mol | Weight |
|---|---|---|---|---|
| ECT | 263.4 | 1 | 8.23e−5 | 21.7 mg |
| AIBN | 164.21 | 0.1 | 7.917e−6 | 1.3 mg from stock soln |

*FA-PEG$_1$-MA, controlling reagent. 275 mg batch split between SMH01-07 and SMH 01-08. AIBN stock solution: 3.9 mg AIBN in 1 mL (1.1066 g) DMSO, for 1.3 mg AIBN added 333 µL AIBN solution; N$_2$ purge = 30 min; T = 68° C.; t = 3.5 h.

Example 5

Copolymerization of HPMAE (2-hydroxypropyl methacrylate) with FA-PEG$_1$-MA and Conversion of the Resulting MacroCTA to a Triblock Polymer Example 5-1

Copolymerization of HPMAE and FA-PEG$_1$-MA

RAFT polymerization was employed to synthesize poly (HPMAE-co-FA-PEG$_1$-MA) using 2,2-azobisisobutyronitrile (AIBN) as the primary radical source and the trithiocarbonate ethyl cyanovaleric acid trithiocarbonate (ECT) as the RAFT chain transfer agent. The HPMAE/FA-PEG$_1$-MA molar feed ratio was selected to obtain a polymer block incorporating ~2 FA-PEG$_1$-MA repeat units per polymer chain. Following polymerization, p[HPMAE-co-FA-PEG$_1$-MA] was purified from residual monomers by extensive dialysis against DMSO (e.g., 1×2 L, 4×1 L, 72 hrs) followed by dialysis against MeOH (e.g., 3×3 L, 24 hrs). All dialysis was performed using Spectrapor dialysis membranes with MWCO=2,000 g/mol. Isolated polymers were obtained by rotary evaporation of the solvent and dried under vacuum. Absolute polymer molecular weight distributions were determined by GPC equipped with laser light scattering and the polymer composition was determined by $^1$H-NMR.

HPMAE, FA-PEG$_1$-MA and ECT in the amounts shown in Table 6 were combined in a vial with ~1.53 g DMSO and stirred until all monomers were completely dissolved. The [HPMAE]:[FA-PEG$_1$-MA] feed ratio was 80:20 and the [M$_o$]/[CTA$_o$] ratio was 60:1. A stock solution of AIBN was prepared in DMSO at a concentration of 3.2 mg/mL and the appropriate volume was added to the polymerization vial to achieve a [CTA$_o$]/[I$_o$] ratio of 20:1. The final monomer concentration of the solution was 30 wt (1.9 M). The reaction vial was purged with N$_2$ and the polymerization was conducted at 68° C. for 4 hours under a N$_2$ atmosphere to reach a targeted conversion of 50%. The reaction was stopped by placing the vial in ice and exposing the mixture to air. p[HPMAE-co-FA-PEG$_1$-MA] was isolated and purified as described above. The product was characterized $^1$H-NMR and GPC. $^1$H NMR of the polymer showed incorporation of the folate monomer at FA-PEG1-MA at 6%, GPC analysis showed a monodisperse molecular weight distribution with Mn=14,500 and PDI 1.13. The dn/dc of the isolated polymer was determined to be 0.070 with 1% LiBr from variable injection volumes from a single concentration. The line was linear and passed near the origin.

TABLE 6

| Name | FW (g/mol) | Equiv. | Mol | Weight | Actual weight |
|---|---|---|---|---|---|
| HPMAE | 144.2 | 56 | 0.0029 | 0.4176 g | 0.4164 g |
| FA-PEG$_1$-MA* | 553.2 | 9 | 1.808e−4 | 0.1000 g | 0.1047 g |

TABLE 6-continued

| Name | FW (g/mol) | Equiv. | Mol | Weight | Actual weight |
|---|---|---|---|---|---|
| ECT | 263.4 | 1 | 2.005e−5 | 5.28 mg | 5.4 mg |
| AIBN | 164.21 | 0.05 | 1.003e−6 | 0.16 mg | from stock** |

*FA-PEG$_1$-MA, controlling reagent. AIBN stock solution:
**for 0.16 mg AIBN add 554 µL AIBN solution (3.2 mg AIBN in 1 mL (1.1066 g) DMSO); N$_2$ purge = 25 min; T = 68° C., t = 4 h.

Example 5-2

Preparation of Diblock Copolymer [HPMAE-co-FA-PEG1-MA]$_{14.5k}$-b-[HPMAE-co-PDSMA-co-BPAM]

RAFT polymerization was employed to synthesize [HPMAE-co-FA-PEG1-MA]$_{14.5k}$-b-[HPMAE-co-PDSMA-co-BPAM] diblock copolymer starting from [HPMAE-co-FA-PEG1-MA]$_{14.5k}$ MacroCTA-1 (Example 5-1) and using 2,2-azobisisobutylbutyronitrile (AIBN) as the primary radical source. [HPMAE-co-FA-PEG1-MA]$_{14.5k}$ was fully dissolved in DMF, and appropriate amounts of HPMAE, PDSMA, and BPAM (Table 7) were added to the reaction vessel. An aliquote of AIBN stock was used to obtain a [CTA$_o$]/[I$_o$] ratio of 1:0.1. The [M$_o$]/[CTA$_o$] ratio was 62:1. The final monomer concentration of the solution was 16 wt % (1.2 M). The reaction vial was purged with N$_2$, and the polymerization was conducted at 68° C. for 3.5 hours under a N$_2$ atmosphere to reach a targeted conversion of 80%. The reaction was stopped by placing the vial in ice and exposing the mixture to air. The product film at the bottom of the vessel was dissolved in methanol and purified by dialysis against methanol (1 L×18 hr, then 1×3 hr), followed by rotary evaporation and drying under vacuum. GPC analysis of the isolated polymer showed a molecular weight distribution with Mn=18,200 g/mol and PDI 1.16. This corresponded to the added block size of 3700 g/mol. The dn/dc of the isolated polymer was determined as described in Experiment 4-1 and was 0.069. $^1$H NMR analysis showed no residual monomers, and BPAM and PDSMA incorporation was seen by NMR.

TABLE 7

| Name | FW (g/mol) | Equiv. | Mol | Weight | Actual weight |
|---|---|---|---|---|---|
| HPMAE | 144.2 | 52.7 | 2.182e−4 | 0.0310 g | 29.5 mg |
| PDSMA | 255.36 | 3.1 | 1.283e−5 | 0.0033 g | 3.9 mg |
| BPAM | 273.33 | 6.2 | 2.57e−5 | 0.0070 g | 7.2 mg |
| MacroCTA-1 | 14,500 | 1 | 4.14e−6 | 0.0600 g | 57.8 mg |
| AIBN | 164.21 | 0.1 | 4.14e−7 | 0.0001 g | from stock |

Final DMF 0.21 ml. AIBN stock solution: 2.1 mg AIBN in 0.9478 g DMF; 0.0306 mL added to the reaction mixture; N$_2$ purge = 20 min on ice; T = 68° C., t = 3 h 15 min.

Example 5-3

Preparation of Triblock Copolymer [HPMAE-co-FA-PEG1-MA]$_{14.5k}$-b-[HPMAE-co-PDSMA-co-BPAM]$_{3.7k}$-b-[D-co-B-co-P]$_{12.7k}$ RAFT polymerization was employed to synthesize triblock copolymer HPMAE-co-FA-PEG1-MA]$_{14.5k}$-b-[HPMAE-co-PDSMA-co-BPAM]$_{3.7k}$-b-[D-co-B-co-P]$_{12.7k}$. starting from [[HPMAE-co-FA-PEG1-MA]$_{14.5k}$-b-[HPMAE-co-PDSMA-co-BPAM] MacroCTA-2 (Example 5-2) and using 2,2-azobisisobutylbutyronitrile (AIBN) as the primary radical source. The MacroCTA was dissolved in acetone and transferred to an 8 mL reaction vial, then the acetone was removed by rotary evaporation. The residue was fully dissolved in 0.284 g DMF, and the appropriate amounts of DMAEMA, BMA, and PAA (Table 8) were added to the vial. An aliquot of AIBN stock was used to obtain a $[CTA_o]/[I_o]$ ratio of 1:0.1. The $[M_o]/[CTA_o]$ ratio was 360:1. The final monomer concentration of the solution was 30 wt % (3 M). The reaction vial was purged with $N_2$, and the polymerization was conducted at 68° C. for 10 hours under a $N_2$ atmosphere to reach a targeted conversion of 50%. Purified product was obtained by dialysis against acetone (1 L×24 hr, 1×6 hr, 1×4 hr), recovered by rotary evaporation and dried under vacuum. GPC analysis of the isolated polymer showed a monomodal molecular weight distribution with Mn=32,900 g/mol and PDI 1.34. The dn/dc of the isolated polymer was determined as described in Experiment 4-1 and was 0.0499. $^1$H NMR analysis showed no residual monomers and confirmed incorporation of DMAEMA, BMA, and PAA.

TABLE 8

| Name | FW (g/mol) | Equiv. | Mol | Weight | Actual weight |
|---|---|---|---|---|---|
| DMAEMA | 157.22 | 90 | 0.000213 | 0.0335 g | 38.4 mg |
| BMA | 142.2 | 180 | 0.000426 | 0.0606 g | 59.4 mg |
| PAA | 114.14 | 90 | 0.000213 | 0.0243 g | 22.9 mg |
| MacroCTA-2 | 18,200 | 1 | 2.37e−6 | 0.0431 g | 42.6 mg |
| AIBN | 164.21 | 0.1 | 2.37e−7 | 3.89e−5 g | from stock |

Final DMF 0.284 mL. AIBN stock solution: 1.8 mg AIBN in 0.4461 g DMF; 0.0105 mL added to the reaction mixture; $N_2$ purge = 30 min; T = 68° C., t = 10 hr.

Example 6

Synthesis of a RGD Peptide Vinyl Monomer

A number of Arg-Gly-Asp (RGD) containing peptides have been shown to demonstrate $\alpha_v\beta_3$ integrin binding.

Solid phase peptide synthesis can be conducted using standard FMOC chemistry (FMOC Solid Phase Peptide Synthesis: A Practical Approach, Chan, W. C.; White, P. D. eds, Oxford Press, Oxford, 2000). The peptides are prepared using a 2-Chlorotrityl resin or HMPA-AM resin, on an ABI 433A peptide synthesizer (0.1 mM) as detailed in the following examples.

Example 6-1

Part 1

Synthesis of Protected Peptide Fragment. Synthesis of FMOC-CYGGRGDTP-OH (SEQ ID NO:26)

Amino Acids: The following amino acid derivatives are used.
FMOC-C(tBu)-OH
FMOC-Y(tBu)-OH
FMOC-G-OH
FMOC-R(Pmc)-OH
FMOC-D(OtBu)-OH
FMOC-T(tBu)-OH
FMOC-P-OH
2-Chlorotrityl resin is loaded with the first amino acid, FMOC-P-OH, by dissolving the amino acid (1.2 eq relative to the resin loading capacity) and diisopropylethylamine (DIPEA, 4 eq relative to the resin loading capacity) in dichloromethane (DCM) (~10 mL per gram of resin) and DMF (enough to dissolve amino acid). To the resulting solution is added the resin, and the reaction is gently stirred for 2 hr. After 2 hr, the resin is filtered, washed (3×) with DCM/MeOH/DIPEA (17:2:1), washed (3×) DCM, washed (2×) DMF, washed (2×) DCM, and dried in vacuo. The resulting FMOC-P-Chlorotrityl resin is utilized for automated peptide synthesis using standard FMOC chemistry. Following the synthesis, the N-terminal FMOC group is removed by treatment of the resin with piperidine. The resulting peptide in its protected form is removed from the resin by treatment of the resin with dilute TFA. The resin is swelled with DCM (~5 mL). 1% TFA in DCM (~10 mL) is added and the suspension is mixed for 2 min, and filtered. The process is repeated ~5 times, and the resin is further washed with DCM (3×30 mL), MeOH (2×30 mL), and DCM (2×30 mL). The combined filtrates are evaporated under reduced pressure to 5% of the volume. Water (~40 mL) is added and the mixture is placed on an ice bath to precipitate the protected peptide. The peptide is isolated by filtration and washed with water (2×30 mL) and dried in vacuo.

Part 2

Preparation of a RGD—Peptide Vinyl Monomer

Peg-3 monomethacrylate is dissolved in DCM, and succinic anhydride (1 eq) and triethylamine (1 eq) are added. The resulting solution is stirred at ambient temperature for 16 hrs. The resulting solution is partitioned in DCM/0.5 N HCl. The organic layer is extracted again with 0.5 N HCl. The combined organic layer is washed with water (1×), dried ($Na_2SO_4$), filtered and dried under reduced atmosphere, to afford the Peg-3 Acid, methacrylate.

The Peg-3 acid methacrylate is dissolved in DMSO. To the resulting solution is added dicyclohexyl carbodiimide and N-hydroxysuccinimide. The solution is stirred for 4 hrs. To the resulting solution is added the protected peptide fragment (1.1 eq in DMSO), and triethylamine (1.1 eq). The reaction is stirred at ambient temperature for 4 hrs. The solution is filtered, and extracted with water (2×), dried ($Na_2SO_4$), filtered and dried under reduced atmosphere, to afford the Protected Peptide fragment—Peg-3 methacrylate.

Part 3 Polymerization

Co-polymerization of the RGD-Peg3-MA with PEGMA$_{4-5}$ is performed as described above for FA-PEG1-MA. The final polymer is purified by dialysis and characterized by $^1$H NMR and GPC.

Part 4

Deprotection and Cyclization of the RGD-Containing Polymer

The resulting polymer is treated with 85% TFA, 5% thioanisole, 5% phenol, 5% water, 2.5% EDT, 1% TIS. The mixture is stirred for 30 min under $N_2$. After 30 min-4 hr, the deprotected peptide polymer is precipitated with diethyl ether and dried in vacuo. The resulting peptide is dissolved in deaerated ammonium bicarbonate (0.1-1 mg/mL) at a concentration lower than 0.1 M and stirred at ambient temperature. The progress of cyclization is followed by Ellmans assay. After cyclization is complete, the solution is frozen and lyophilized.

Example 6-2

Part 1

Synthesis of Protected Peptide Fragment. Synthesis of FMOC-CYGGRGDTP-OH (SEQ ID NO:26)

Amino Acids: The following amino acid derivatives will be used.

FMOC-C(trt)-OH
FMOC-Y(tBu)-OH
FMOC-G-OH
FMOC-R(Pmc)-OH
FMOC-D(OtBu)-OH
FMOC-T(trt)-OH
FMOC-P-OH 2-Chlorotrityl resin is loaded with the first amino acid, FMOC-P-OH, by dissolving the amino acid (1.2 eq relative to the resin loading capacity) and diisopropylethylamine (DIPEA, 4 eq relative to the resin loading capacity) in dichloromethane (DCM) (~10 mL per gram of resin) and DMF (enough to dissolve amino acid). To the resulting solution is added the resin, and the reaction is gently stirred for 2 hr. After 2 hr, the resin is filtered, washed (3×) with DCM/MeOH/DIPEA (17:2:1), washed (3×) DCM, washed (2×) DMF, washed (2×) DCM, and dried in vacuo. The resulting FMOC-P-Chlorotrityl resin is utilized for automated peptide synthesis using standard FMOC chemistry. Following synthesis, the N-terminal FMOC group is removed by treatment of the resin with piperidine. The resulting peptide is removed from the resin by treatment of the resin with dilute TFA, also resulting in the loss of the trt protecting groups. The resin is swelled with DCM (~5 mL). 1% TFA in DCM (~10 mL) is added and the suspension is mixed for 2 min, and filtered. The process is repeated ~5 times, and the resin is further washed with DCM (3×30 mL), MeOH (2×30 mL), and DCM (2×30 mL). The combined filtrates are evaporated under reduced pressure to 5% of the volume. Water (~40 mL) is added and the mixture is placed on an ice bath to precipitate the protected peptide. The peptide is isolated by filtration and washed with water (2×30 mL) and dried in vacuo.

The resulting protected peptide fragment is cyclized by dissolved in MeOH (1-10 mg/mL). 1 M HCl (0.1 mL/mg) is added, followed immediately by 0.1M $I_2$ in 50% MeOH. The resulting solution is stirred rapidly for 30 min and the $I_2$ quenched with sodium thiosulfate. The MeOH is removed by reduced pressure and the solution cooled to precipitate the cyclic protected peptide. The product is isolated by filtration and washed with water (2×) and dried in vacuo.

Part 2

Preparation of a RGD—Peptide Vinyl Monomer

NHS-Peg 3 vinyl monomer is prepared as in example 1, part 2. The NHS-peg3 vinyl monomer is taken up in DMSO and to the resulting solution is added the protected cyclic peptide fragment (1.1 eq in DMSO), and triethylamine (1.1 eq). The reaction is stirred at ambient temperature for 4 hrs. The solution is filtered, and extracted with water (2×), dried ($Na_2SO_4$), filtered and dried under reduced atmosphere, to afford the Protected Peptide fragment—Peg-3 methacrylate.

Part 3 Polymerization

Co-polymerization of the peptide-Peg3-MA with PEGMA$_{4-5}$ is performed as described above for FA-PEG1-MA. The final polymer is purified by dialysis and characterized by $^1$H NMR and GPC.

Part 4

Deprotection of the RGD Containing Peptide

The resulting polymer is treated with 95% TFA, 2.5% water, 2.5% TIS. The mixture is stirred for 30 min under $N_2$. After 30 min-4 hr, the deprotected peptide polymer is precipitated with diethyl ether and dried in vacuo.

Example 6-3

By similar methods to those detailed in Example 1 and 2, the following RGD vinyl monomers can be prepared and polymerized. In the following examples, the peptide amino terminus is attached to the succinylated peg 3 vinyl monomer, the underlined amino acid residues constitute the cyclic portion if the peptide is a cyclic peptide (Red test indicates second disulfide bonds), the —OH signifies the carboxylic acid on the C-terminus of the peptide fragment.

```
                                          (SEQ ID NO:  1)
CH2C(CH3)CO-Peg3-CO(CH2)2CO-ACRGDMFGCA-OH (SEQ ID NO:  2)
CH2C(CH3)CO-Peg3-CO(CH2)2CO-GRGDSP (SEQ ID NO:  3)
CH2C(CH3)CO-Peg3-CO(CH2)2CO-CDCRGDCFC (SEQ ID NO:  4)
CH2C(CH3)CO-Peg3-CO(CH2)2CO-KRGDY (SEQ ID NO:  5)
CH2C(CH3)CO-Peg3-CO(CH2)2CO-LRGDNLSNIDYILIKAS (SEQ ID NO:  6)
CH2C(CH3)CO-Peg3-CO(CH2)2CO-LRGDNSAKVDAIGLEIV (SEQ ID NO:  7)
CH2C(CH3)CO-Peg3-CO(CH2)2CO-LRGDNDISTKYFQMSLE (SEQ ID NO:  8)
CH2C(CH3)CO-Peg3-CO(CH2)2CO-LRGDNVILQQSAADIAR (SEQ ID NO:  9)
CH2C(CH3)CO-Peg3-CO(CH2)2CO-CDCRGDCFC (SEQ ID NO: 10)
CH2C(CH3)CO-Peg3-CO(CH2)2CO-GRGDNP (SEQ. ID NO: 11)
CH2C(CH3)CO-Peg3-CO(CH2)2CO-ACDCRGDCFCG (SEQ ID NO: 12)
CH2C(CH3)CO-Peg3-CO(CH2)2CO-ACDCRGDCFCG (SEQ ID NO: 13)
CH2C(CH3)CO-Peg3-CO(CH2)2CO-RGDDFK (SEQ ID NO: 14)
CH2C(CH3)CO-Peg3-CO(CH2)2CO-c(RGDfK)

(SEQ ID NO: 15)
CH2C(CH3)CO-Peg3-CO(CH2)2CO-[c(RGDfK)]2
```

```
                                          (SEQ ID NO: 16)
CH2C(CH3)CO-Peg3-CO(CH2)2CO-ICRRARGDNPDDRCT (SEQ ID NO: 17)
CH2C(CH3)CO-Peg3-CO(CH2)2CO-ICRRARGDNPDDRCT
```

Example 6-4

By similar methods to those detailed in Example 1 and 2, the following peptide targeting vinyl monomers (EGF, epidermal growth factor; and LOX-1, lectin-like oxidized LDL receptor) can be prepared and polymerized. In the following examples, the peptide amino terminus is attached to the succinylated peg 3 vinyl monomer, the underlined amino acid residues constitute the cyclic portion if the peptide is a cyclic peptide (Red test indicates second disulfide bonds), the —OH signifies the carboxylic acid on the C-terminus of the peptide fragment.

```
                                          (SEQ ID NO: 18)
CH2C(CH3)CO-Peg3-CO(CH2)2CO-PLAEIDGIELTY (Integrin
binding)

(SEQ ID NO: 19)
CH2C(CH3)CO-Peg3-CO(CH2)2CO-
HSDGTFTSELSRLRDSARLQRLLQGLV (Secretin)

(SEQ ID NO: 20)
CH2C(CH3)CO-Peg3-CO(CH2)2CO-NPVVGYIGERPQYRDL (GE7
(from EGF))

(SEQ ID NO: 21)
CH2C(CH3)CO-Peg3-CO(CH2)2CO-
CTTTHTFVKALTMDGKQAAWRFIRIDTAC (NL4)

(SEQ ID NO: 22)
CH2C(CH3)CO-Peg3-CO(CH2)2CO-ELYENKPRRPYIL
(Neurotensin)

(SEQ ID NO: 23)
CH2C(CH3)CO-Peg3-CO(CH2)2CO-LSIPPKA (LOX-1 binding)

(SEQ ID NO: 24)
CH2C(CH3)CO-Peg3-CO(CH2)2CO-FQTPPQL (LOX-1 binding)

(SEQ ID NO: 25)
CH2C(CH3)CO-Peg3-CO(CH2)2CO-LTPATAI (LOX-1 binding)
```

Example 7

Synthesis of a Biotin Targeting Monomer

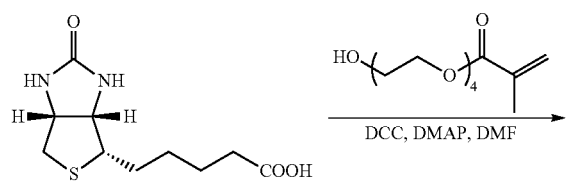

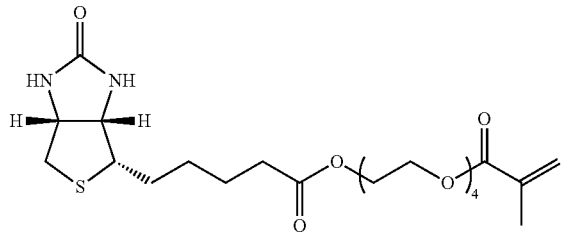

To a solution of biotin (1 equivalent), DMAP (catalytic amounts), and PEG4-MA alcohol (1 equiv.) in DMF is added a solution of DCC (1.05 equiv.) in DMF. The reaction mixture is stirred at room temperature for 18 hr. DCU precipitate is filtered off, and the filtrate is evaporated under vacuum to yield the crude product which is purified by chromatography and characterized by $^1$H NMR.

Example 8

Synthesis of DUPA-PEG$_4$-MA, a PSMA Inhibitor-Targeted Monomer

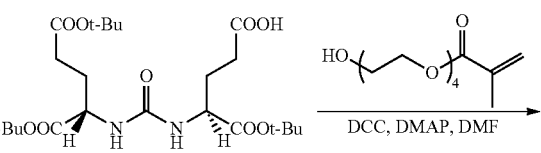

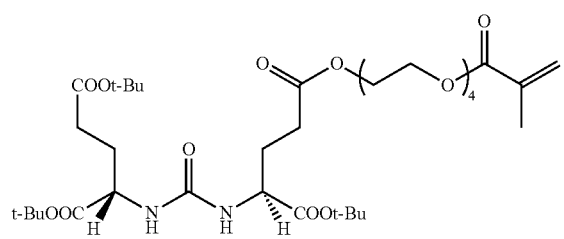

The synthesis is performed analogously to the synthesis of the biotin-targeted monomer described in the Experiment 6 staring with tri-t-Bu ester of 2-[3-(1,3-dicarboxypropyl)-ureido]pentadioic acid (DUPA, Prostate-Specific Membrane Antigen Targeted Imaging and Therapy of Prostate Cancer Using a PSMA Inhibitor as a Homing Ligand. S. A. Kularatne, K. Wang, H-K. R. Santhapuram, P. S. Low, Molecular Pharmaceutics 1999, Vol. 6, No. 3, p. 780-789.) The product is purified by chromatography and characterized by $^1$H NMR. The monomer is used in its t-Bu protected form in the synthesis of block copolymers as described above. The t-Bu protecting groups are removed from the final polymer product by treatment with TFA in dichloromethane.

Example 9

Synthesis of Bisphosphonate MA Monomer

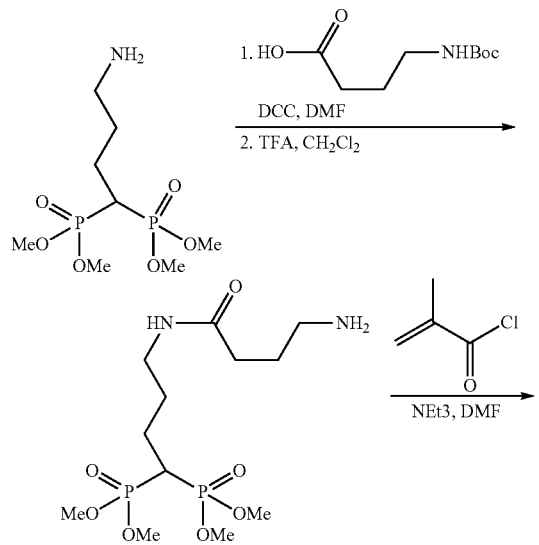

Tetramethyl 4-aminobutyl-1,1-bisphosphonate is acylated with 1 equivalent of Boc-protected 4-aminobutyric acid using DCC (1 eq.) in DMF. The resulting Boc-protected derivative is deprotected with TFA/CH$_2$Cl$_2$, and the resulting amine is acylated with 1.1 eq. of methacryloyl chloride in the presence of 1.1 eq. of NEt$_3$ in DMF at 0° C. The product is purified by chromatography and characterized by $^1$H NMR. The monomer can be used in the synthesis of copolymers as described above. Removal of the methyl protecting groups from the bisphosphonate pendant groups in the final polymer is achieved by treatment of the polymer with TMSBr or TMSI in DMF for 8-16 hr at room temperature.

---

What is claimed is:

1. A monomer of Formula M1

Formula M1

$$\underset{M^1\phantom{XX}M^3}{M^2}\!\!\diagup\!\!=\!\!\diagdown\!\!\underset{\phantom{XX}}{M^4}$$

wherein $M^1$ and $M^2$ are independently selected from the group consisting of hydrogen, hydrocarbyl, substituted hydrocarbyl, heterocyclo, and substituted carbonyl, provided, however, $M^1$ and $M^2$ are not each selected from the group consisting of aryl, heteroaryl, and heterosubstituted carbonyl;

$M^3$ is hydrogen, hydrocarbyl, substituted hydrocarbyl, heterocyclo, or substituted carbonyl, and $M^4$ is —C(O)O$M^{40}$, —C(O)S$M^{40}$, —C(O)N$M^{40}M^{41}$, —Ar-$M^{40}$ or -Het-$M^{40}$, Ar is arylene, Het is heteroarylene, $M^{41}$ is hydrogen, hydrocarbyl, substituted hydrocarbyl, heterohydrocarbyl, substituted heterohydrocarbyl, or heterocyclo, and $M^{40}$ contains, as a terminal moiety, a targeting moiety selected from the group consisting of folate and folate analogs, provided $M^3$ and $M^4$ are not each selected from the group consisting of optionally substituted aryl, optionally substituted heteroaryl, and heterosubstituted carbonyl.

2. The monomer of claim 1 wherein $M^3$ is hydrogen, methyl, ethyl, or propyl.

3. The monomer of claim 1 wherein $M^{40}$ is a substituted hydrocarbyl or a substituted heterohydrocarbyl containing the terminal targeting moiety.

4. The monomer of claim 1 wherein $M^3$ is hydrogen, methyl, ethyl, or propyl; and $M^{40}$ is a substituted hydrocarbyl or a substituted heterohydrocarbyl containing the terminal targeting moiety.

5. The monomer of claim 1 wherein $M^3$ is hydrogen, methyl, ethyl, or propyl; and $M^4$ is —C(O)O$M^{40}$, —C(O)S$M^{40}$, or —C(O)N$M^{40}M^{41}$.

6. The monomer of claim 1 wherein $M^{40}$ contains, as the terminal targeting moiety, a moiety having the formula

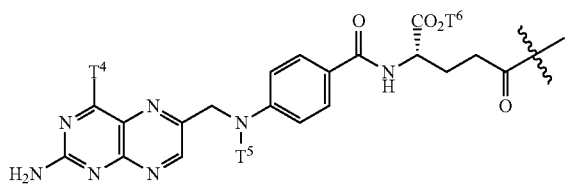

wherein the symbol, ⌇, designates the point of attachment of the targeting moiety to the remainder of $M^{40}$, $T^4$ is hydroxy, optionally substituted alkoxy, or amino, $T^5$ is hydrogen or alkyl, and $T^6$ is hydrogen or optionally substituted alkyl.

7. A monomer of Formula M10

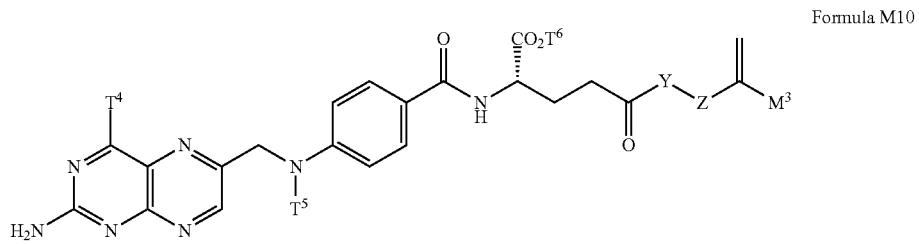

Formula M10 wherein M³ is hydrogen, hydrocarbyl, substituted hydrocarbyl, heterocyclo, or substituted carbonyl; Y is a bond or a linking group selected from the group consisting of hydrocarbylene, substituted hydrocarbylene, heterohydrocarbyl, and substituted heterohydrocarbyl; T⁴ is hydroxy, optionally substituted alkoxy, or amino; T⁵ is hydrogen or alkyl, T⁶ is hydrogen, alkyl, substituted alkyl, heterohydrocarbyl, or substituted heterohydrocarbyl; Z is —C(O)O—, —C(O)S—, —C(O)N(M⁴¹)-, —Ar-M⁴⁹- or Het-M⁴⁹-; Ar is arylene; Het is heteroarylene; M⁴¹ is hydrogen, hydrocarbyl, substituted hydrocarbyl, heterohydrocarbyl, substituted heterohydrocarbyl, or heterocyclo; M⁴⁹ is oxygen, sulfur, or —N(M⁵⁰)-; and M⁵⁰ is hydrogen, hydrocarbyl or substituted hydrocarbyl.

8. The monomer of claim 7 wherein M³ is hydrogen, methyl, ethyl, or propyl, T⁴ is hydroxy, and T⁵ and T⁶ are hydrogen.

9. The monomer of claim 7 wherein M³ and T⁶ are independently hydrogen, methyl, ethyl, or propyl; Z is —C(O)O—, —C(O)S—, or —C(O)N(M⁴¹)-; and M⁴¹ is hydrogen, hydrocarbyl, substituted hydrocarbyl, heterohydrocarbyl, substituted heterohydrocarbyl, or heterocyclo.

10. The monomer of claim 7 wherein Y is alkylene or (poly)alkylene oxide.

11. The monomer of claim 7 wherein M³ and T⁶ are independently hydrogen, methyl, ethyl, or propyl, Z is —C(O)O—, —C(O)S—, or —C(O)N(M⁴¹)-; Y is alkylene or (poly)alkylene oxide; and M⁴¹ is hydrogen, hydrocarbyl, substituted hydrocarbyl, heterohydrocarbyl, substituted heterohydrocarbyl, or heterocyclo.

12. The monomer of claim 7 wherein Z is —C(O)O— or —C(O)S— and the is of Formula M11 or M12

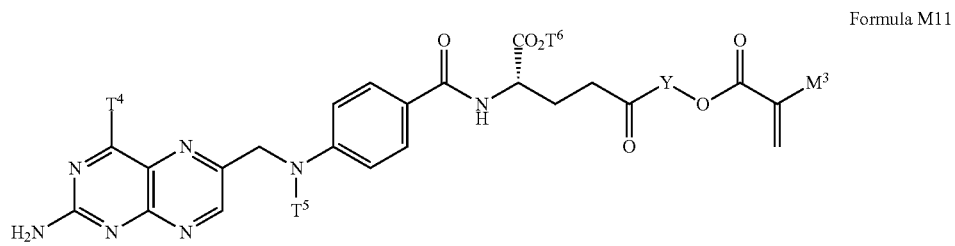

Formula M11

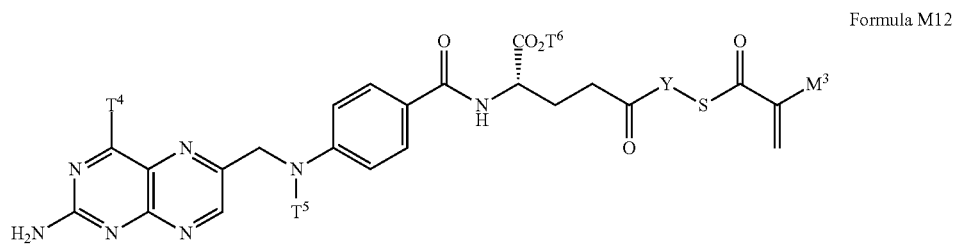

Formula M12 wherein $M^3$ is hydrogen, methyl, ethyl, or propyl, Y is a linking group selected from the group consisting of hydrocarbylene, substituted hydrocarbylene, heterohydrocarbyl, and substituted heterohydrocarbyl; $T^4$ is hydroxy, optionally substituted alkoxy, or amino; $T^5$ is hydrogen or alkyl, and $T^6$ is hydrogen, alkyl or substituted alkyl.

13. The monomer of claim 5, wherein $M^{40}$ is a substituted hydrocarbyl or a substituted heterohydrocarbyl containing the terminal targeting moiety.

* * * * *

```
                    SEQUENCE LISTING

<160> NUMBER OF SEQ ID NOS: 26

<210> SEQ ID NO 1
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified A

<400> SEQUENCE: 1

Xaa Cys Arg Gly Asp Met Phe Gly Cys Ala
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified G

<400> SEQUENCE: 2

Xaa Arg Gly Asp Ser Pro
1               5

<210> SEQ ID NO 3
<211> LENGTH: 9
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified C

<400> SEQUENCE: 3

Xaa Asp Cys Arg Gly Asp Cys Phe Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified K

<400> SEQUENCE: 4

Xaa Arg Gly Asp Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified L

<400> SEQUENCE: 5

Xaa Arg Gly Asp Asn Leu Ser Asn Ile Asp Tyr Ile Leu Ile Lys Ala
1               5                   10                  15

Ser

<210> SEQ ID NO 6
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified L

<400> SEQUENCE: 6

Xaa Arg Gly Asp Asn Ser Ala Lys Val Asp Ala Ile Gly Leu Glu Ile
1               5                   10                  15

Val

<210> SEQ ID NO 7
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: X at position 1 is CH2C(CH3)CO-Peg3-CO(CH2)2CO
      modified L

<400> SEQUENCE: 7

Xaa Arg Gly Asp Asn Asp Ile Ser Thr Lys Tyr Phe Gln Met Ser Leu
1               5                   10                  15

Glu

<210> SEQ ID NO 8
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified L

<400> SEQUENCE: 8

Xaa Arg Gly Asp Asn Val Ile Leu Gln Gln Ser Ala Ala Asp Ile Ala
1               5                   10                  15

Arg

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified C

<400> SEQUENCE: 9

Xaa Asp Cys Arg Gly Asp Cys Phe Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified G

<400> SEQUENCE: 10

Xaa Arg Gly Asp Asn Pro
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified A
```

<400> SEQUENCE: 11

Xaa Cys Asp Cys Arg Gly Asp Cys Phe Cys Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified A

<400> SEQUENCE: 12

Xaa Cys Asp Cys Arg Gly Asp Cys Phe Cys Gly
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified R

<400> SEQUENCE: 13

Xaa Gly Asp Asp Phe Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified R

<400> SEQUENCE: 14

Xaa Gly Asp Phe Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified R

<400> SEQUENCE: 15

Xaa Gly Asp Phe Lys
1               5

```
<210> SEQ ID NO 16
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified I

<400> SEQUENCE: 16

Xaa Cys Arg Arg Ala Arg Gly Asp Asn Pro Asp Asp Arg Cys Thr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified I

<400> SEQUENCE: 17

Xaa Cys Arg Arg Ala Arg Gly Asp Asn Pro Asp Asp Arg Cys Thr
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified P

<400> SEQUENCE: 18

Xaa Leu Ala Glu Ile Asp Gly Ile Glu Leu Thr Tyr
1               5                   10

<210> SEQ ID NO 19
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified H

<400> SEQUENCE: 19

Xaa Ser Asp Gly Thr Phe Thr Ser Glu Leu Ser Arg Leu Arg Asp Ser
1               5                   10                  15

Ala Arg Leu Gln Arg Leu Leu Gln Gly Leu Val
            20                  25

<210> SEQ ID NO 20
<211> LENGTH: 16
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified N

<400> SEQUENCE: 20

Xaa Pro Val Val Gly Tyr Ile Gly Glu Arg Pro Gln Tyr Arg Asp Leu
1               5                   10                  15

<210> SEQ ID NO 21
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified C

<400> SEQUENCE: 21

Xaa Thr Thr Thr His Thr Phe Val Lys Ala Leu Thr Met Asp Gly Lys
1               5                   10                  15

Gln Ala Ala Trp Arg Phe Ile Arg Ile Asp Thr Ala Cys
            20                  25

<210> SEQ ID NO 22
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified E

<400> SEQUENCE: 22

Xaa Leu Tyr Glu Asn Lys Pro Arg Arg Pro Tyr Ile Leu
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified L

<400> SEQUENCE: 23

Xaa Ser Ile Pro Pro Lys Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: X at position 1 is CH2C(CH3)CO-Peg3-CO(CH2)2CO
      modified F

<400> SEQUENCE: 24

Xaa Gln Thr Pro Pro Gln Leu
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is CH2C(CH3)CO-Peg3-CO(CH2)2CO
      modified L

<400> SEQUENCE: 25

Xaa Thr Pro Ala Thr Ala Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at position 1 is FMOC-Cysteine

<400> SEQUENCE: 26

Xaa Tyr Gly Gly Arg Gly Asp Thr Pro
1               5
```